(12) United States Patent
Davenport Huyer et al.

(10) Patent No.: US 11,666,598 B2
(45) Date of Patent: Jun. 6, 2023

(54) BIOMATERIAL COMPRISING POLY-(ITACONATE- CO-CITRATE-CO-OCTANEDIOL)

(71) Applicants: Locke Davenport Huyer, Toronto (CA); Miles Montgomery, East Gwillimbury (CA); Milica Radisic, Toronto (CA)

(72) Inventors: Locke Davenport Huyer, Toronto (CA); Miles Montgomery, East Gwillimbury (CA); Milica Radisic, Toronto (CA)

( * ) Notice: Subject to any disclaimer, the term of this patent is extended or adjusted under 35 U.S.C. 154(b) by 329 days.

(21) Appl. No.: 16/927,576

(22) Filed: Jul. 13, 2020

(65) Prior Publication Data

US 2021/0008100 A1 Jan. 14, 2021

Related U.S. Application Data

(60) Provisional application No. 62/872,878, filed on Jul. 11, 2019.

(51) Int. Cl.
| | | |
|---|---|---|
| *A61K 31/765* | (2006.01) | |
| *C08L 67/02* | (2006.01) | |
| *A61L 27/38* | (2006.01) | |
| *A61K 9/00* | (2006.01) | |
| *A61P 29/00* | (2006.01) | |
| *A61P 31/04* | (2006.01) | |
| *A61K 31/047* | (2006.01) | |

(52) U.S. Cl.
CPC .......... *A61K 31/765* (2013.01); *A61K 9/0024* (2013.01); *A61K 31/047* (2013.01); *A61L 27/3839* (2013.01); *A61P 29/00* (2018.01); *A61P 31/04* (2018.01); *C08L 67/02* (2013.01); *A61K 2123/00* (2013.01); *C08L 2312/06* (2013.01)

(58) Field of Classification Search
CPC . A61K 31/765; A61K 9/0024; A61L 27/3839; A61P 29/00; C08L 67/02
See application file for complete search history.

(56) References Cited

U.S. PATENT DOCUMENTS 10,172,974 B2 * 1/2019 Yang ..................... A61L 26/008

OTHER PUBLICATIONS

Wang et al, Engineering Multifunctional Bioactive Citrate-Based Biomaterials for Tissue Engineering Bioactive Materials, 19, pp. 511-537. (Year: 2023).*
Winkler, M., Lacerda, T. M., Mack, F. & Meier, M. A. R. Renewable Polymers from Itaconic Acid by Polycondensation and Ring-Opening-Metathesis Polymerization. Macromolecules 48, 1398-1403, doi:10.1021/acs.macromol.5b00052 (2015).

(Continued)

*Primary Examiner* — Carlos A Azpuru
(74) *Attorney, Agent, or Firm* — Ridout & Maybee LLP

(57) ABSTRACT

A method of treating infection and/or inflammation in a subject includes steps of providing a polyester biomaterial comprising diol monomers and at least first carboxylate monomers, wherein the first carboxylate monomers are itaconate; and administering the polyester biomaterial to the subject. The polyester biomaterial can be in the form of a biomimetic, and characterized by hydrolytic degradability. The polyester biomaterial may further include second carboxylate monomers. The biomaterial can be poly(itaconate-co-citrate-co-octanediol).

14 Claims, 25 Drawing Sheets

(56) References Cited

OTHER PUBLICATIONS

Wang, Y., Ameer, G. A., Sheppard, B. J. & Langer, R. A tough biodegradable elastomer. Nat Biotech 20, 602-606, doi:0.1038/nbt0602-602 (2002).

Yang, J., Webb, A. R., Pickerill, S. J., Hageman, G. & Ameer, G. A. Synthesis and evaluation of poly(diol citrate) biodegradable elastomers. Biomaterials 27, 1889-1898, doi:10.1016/j.biomaterials.2005.05.106 (2006).

Nijst, C. L. E. et al. Synthesis and Characterization of Photocurable Elastomers from Poly(glycerol-co-sebacate). Biomacromolecules 8, 3067-3073, doi:10.1021/bm070423u (2007).

Ifkovits, J. L., Padera, R. F. & Burdick, J. A. Biodegradable and radically polymerized elastomers with enhanced processing capabilities. Biomedical materials 3, 034104, doi:10.1088/1748-6041/3/3/034104 (2008).

Wang, Y., Kibbe, M. R. & Ameer, G. A. Photo-crosslinked Biodegradable Elastomers for Controlled Nitric Oxide Delivery. Biomater Sci 1, 625-632, doi:10.1039/C3BM00169E (2013).

Amsden, B. G., Misra, G., Gu, F. & Younes, H. M. Synthesis and characterization of a photo-cross-linked biodegradable elastomer Biomacromolecules 5, 2479-2486 (2004).

Timbart, L. & Amsden, B. G. Functionalizable biodegradable photocrosslinked elastomers based on 2-oxepane-1,5-dione. Journal of Polymer Science Part A: Polymer Chemistry 46, 8191-8199, doi:10.1002/pola.23117 (2008).

Tran, R. T. et al. Synthesis and characterization of a biodegradable elastomer featuring a dual crosslinking mechanism. Soft matter 6, 2449-2461, doi:10.1039/C001605E (2010).

Davenport Huyer, L. et al. Highly Elastic and Moldable Polyester Biomaterial for Cardiac Tissue Engineering Applications. ACS Biomaterials Science & Engineering, doi:10.1021/acsbiomaterials.5b00525 (2016).

Gyawali, D., Tran, R. T., Guleserian, K. J., Tang, L. & Yang, J. Citric-acid-derived photo-cross-linked biodegradable elastomers. Journal of biomaterials science. Polymer edition 21, 1761-1782, Joi:10.1163/092050609X12567178204169 (2010).

Zhao, H. & Ameer, G. A. Modulating the mechanical properties of poly(diol citrates) via the incorporation of a second type of crosslink network. Journal of Applied Polymer Science 114, 1464-1470, doi:10.1002/app.30735 (2009).

Brännström, S., Finnveden, M., Johansson, M., Martinelle, M. & Malmström, E. Itaconate Based Polyesters: Selectivity and Performance of Esterification Catalysts. European Polymer Journal, doi:10.1016/j.eurpolymj.2018.04.017 (2018).

Yang, J., Webb, A. R. & Ameer, G. A. Novel Citric Acid-Based Biodegradable Elastomers for Tissue Engineering. Advanced Materials 16, 511-516, doi:10.1002/adma.200306264 (2004).

Lang, N. et al. A Blood-Resistant Surgical Glue for Minimally Invasive Repair of Vessels and Heart Defects. Science translational medicine 6, 218ra216, doi:10.1126/scitranslmed.3006557 (2014).

Lv, A., Li, Z.-L., Du, F.-S. & Li, Z.-C. Synthesis, Functionalization, and Controlled Degradation of High Molecular Weight Polyester from Itaconic Acid via ADMET Polymerization. Macromolecules 47, 7707-7716, doi:10.1021/ma5020066 (2014).

\* cited by examiner

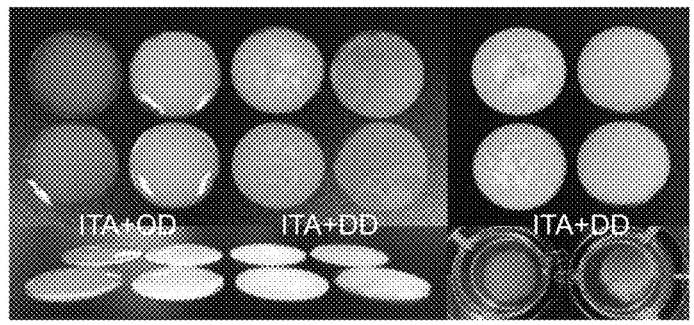
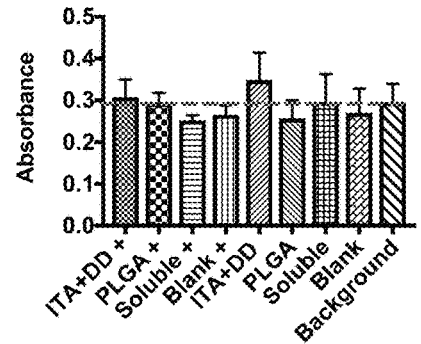
FIG.7A  FIG.7B
FIG.7C
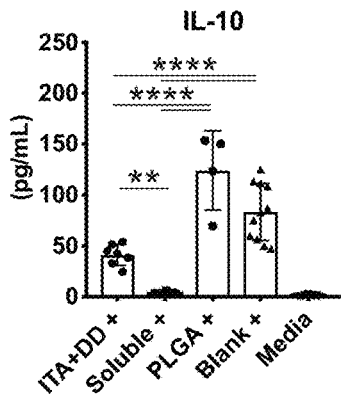
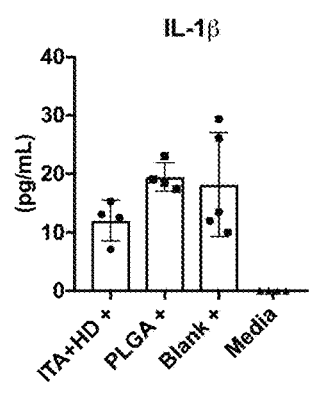
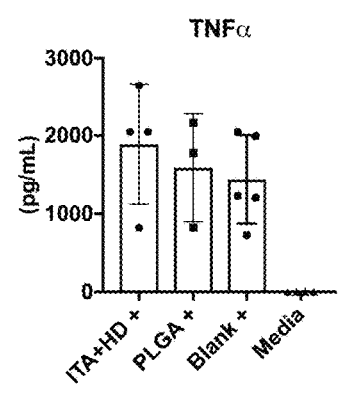
FIG.7D  FIG.7E  FIG.7F
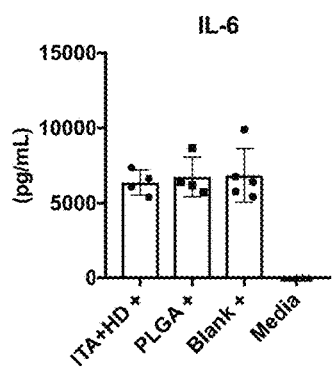
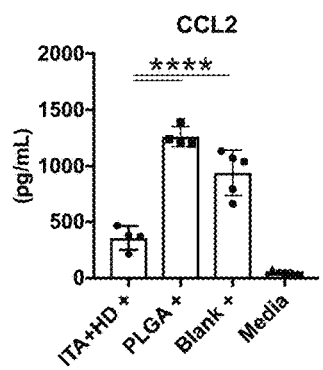
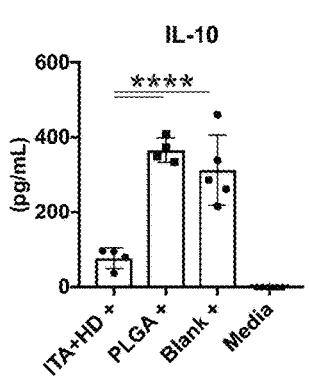
FIG.7G  FIG.7H  FIG.7I

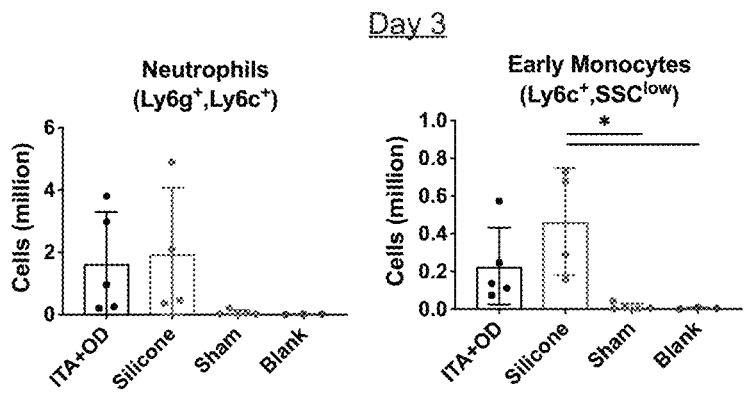
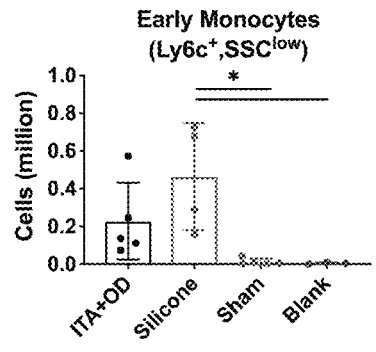
FIG.9C  FIG.9D
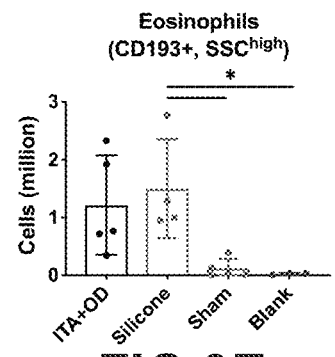
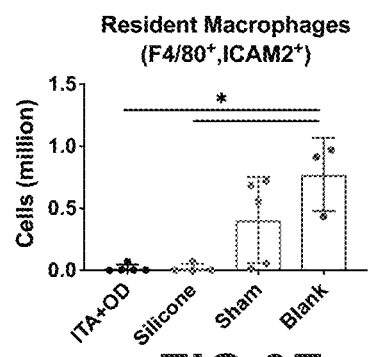
FIG.9E  FIG.9F
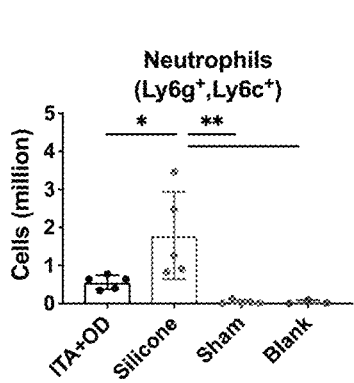
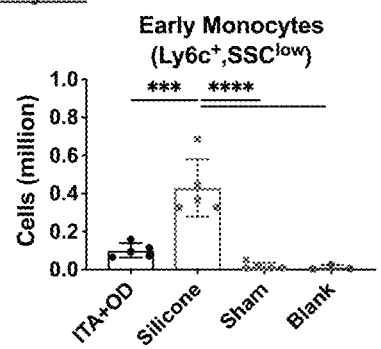
FIG.9G  FIG.9H
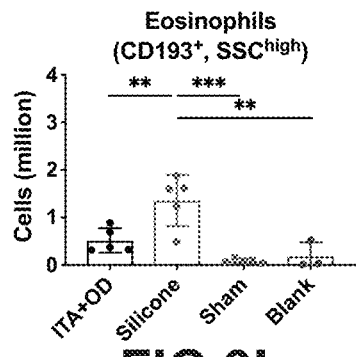
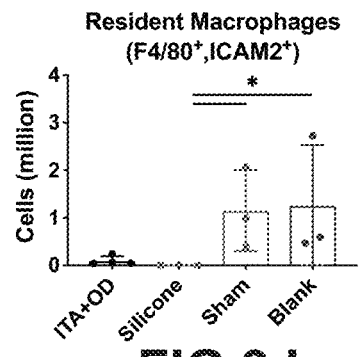
FIG.9I  FIG.9J

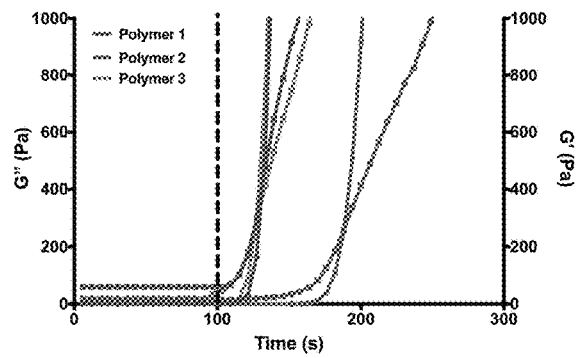
FIG.15A
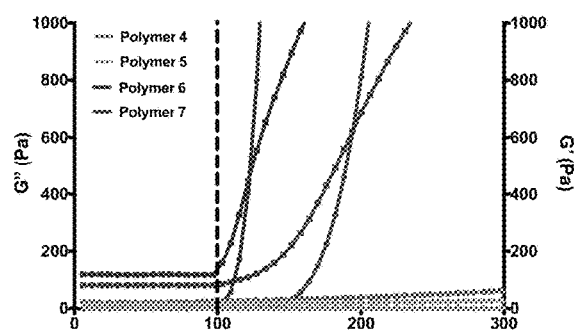
FIG.15B
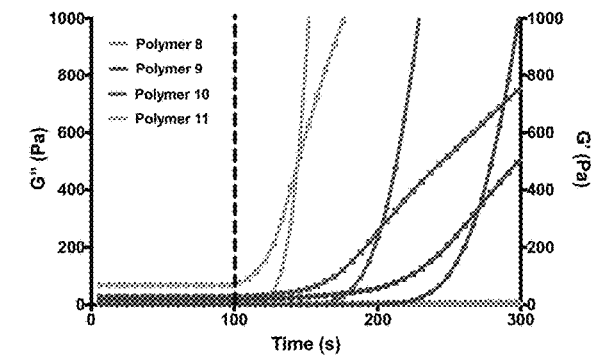
FIG.15C
| Polymer | Feed Ratio DMI:TEC:OD (mol:mol) | Gelation Time (s) |
|---|---|---|
| 1 | 1:1:2 High ITA | 34 |
| 2 | | 88 |
| 3 | | 27 |
| 4 | 1:2:3 Low ITA | No gelation |
| 5 | | No gelation |
| 6 | | 22 |
| 7 | | 94 |
| 8 | 3:4:7 Moderate ITA | No gelation |
| 9 | | 173 |
| 10 | | 102 |
| 11 | | 45 |
FIG.15D

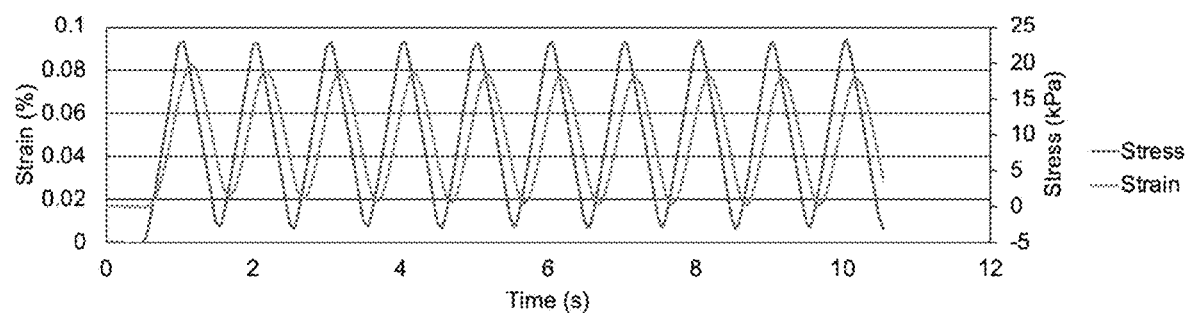
FIG.17A
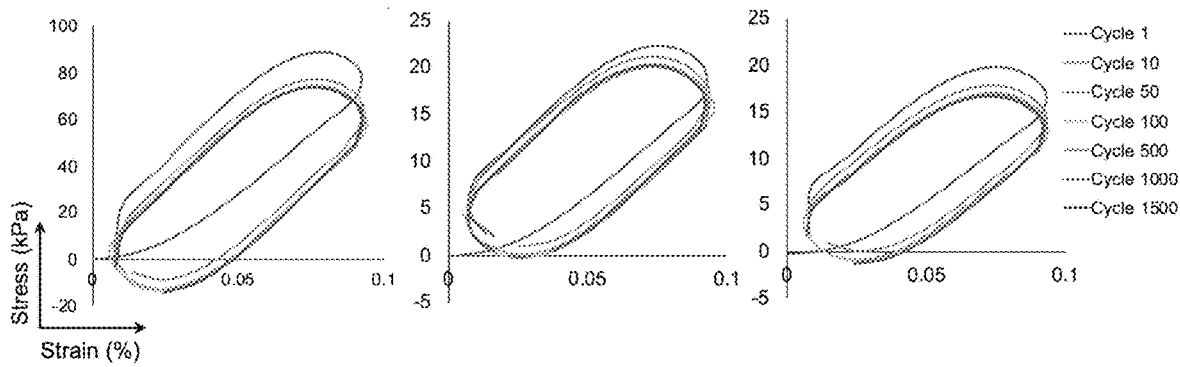
FIG.17B  FIG.17C  FIG.17D

BIOMATERIAL COMPRISING POLY(ITACONATE-CO-CITRATE-CO-OCTANEDIOL)

FIELD

The present disclosure relates to a polymer biomaterial. In particular, the disclosure relates to a polyester biomaterial containing itaconate, and a method of treating infection and/or inflammation by administering the polyester biomaterial containing itaconate to a subject.

BACKGROUND

The use of polymer-based biomaterial implants in healthcare has been extensively reported[1]. Many of these devices are subject to limited efficacy due to poor interaction with host immunity[2], development of surgical site infection[3], or cell toxicity. Technological development of materials with inherent bioactivity to combat these limitations has been notable, but the complexity of the cell-material microenvironment often leads to beneficial outcomes in a single functionality with detrimental impact on others[3, 4]. Biomaterials designed in a biomimetic approach to support implant integration, minimize local infection, and remain non-toxic to the body would be ideal.

Under glucose deprived conditions, ITA is a potent inhibitor of isocitrate lyase (ICL)[10, 11], a key enzyme in the microorganism glyoxylate shunt that is often attributed to the resistivity of organisms[12]. ITA enables the innate immunity to control bacterial presence and modulate local inflammation without exerting damage to the surrounding tissue, roles which represent exact design criteria for the biomaterial of the present disclosure.

Growth inhibition has been observed on a number of bacterial strains in the presence of ITA, including *Mycobacterium tuberculosis*[13], methicillin resistant *Staphylococcus aureus* (MRSA)[14] and multidrug resistant *Acinetobacter baumannii*[14]. Initially considered primarily as an antibacterial response in innate immunity, ITA has emerged recently as a mechanistic regulator of macrophage inflammation[15]. Similar to its antibacterial properties, ITA is an enzyme inhibitor of succinate dehydrogenase (SDH) in macrophages[16], with demonstrated attenuation of inflammation through reduction of succinate oxidation based reactive oxygen species generation[17]. The mechanism of anti-inflammatory characteristics has been shown to be multi-factorial; ITA derivatives are demonstrated activators of erythroid 2-related factor 2 (NRF2)[18, 19], a suggested critical controller of injury[20], and as a molecular regulator of electrophilic stress along the IκBζ-AFT3 axis[19].

The multimodal behavior of ITA presents opportunity for its role as a therapeutic and inspires synthesis of a polymer that would facilitate multiple roles in a similar manner that cells do.

SUMMARY

In the present disclosure, the inventors were inspired by a small molecule, itaconate (ITA), that is evolutionarily preserved in the innate immunity[5]. Produced in activated macrophages through immune responsive gene 1 (IRG1)-itaconate axis[6-8], recent findings have indicated the role of this molecule as an antibacterial and anti-inflammatory metabolite[9].

In this disclosure, the present inventors harness the duality of ITA to both modulate infection and inflammation in a biomimetic strategy of polymer design. The present inventors hypothesized that such biomaterial could offer both improved material integration and reduced bacterial colonization at the cell-material interface. To do so, the present inventors present the scalable incorporation of ITA into a family of polyester material backbones and utilize hydrolytically driven degradation for the quantified sustained depot release from material surfaces. With quantified release from multiple material formulations, the present inventors demonstrate the ability to attenuate bacterial growth and macrophage inflammation in the local environment of ITA polymer materials in vitro and in vivo.

Thus there is disclosed herein a method of treating infection and/or inflammation in a subject, said method comprises steps of:

providing a polyester biomaterial comprising diol monomers and at least first carboxylate monomers, wherein the first carboxylate monomers are itaconate; and administering the polyester biomaterial to the subject.

The polyester biomaterial is in the form of a biomimetic.

The polyester biomaterial is characterized by hydrolytic degradability.

The polyester biomaterial is formed by polycondensation of the diol monomers with the itaconate monomers in the presence of a radical inhibitor.

The polyester biomaterial may be formed by polycondensation at 120° C. to 130° C. at atmospheric pressure.

The polyester biomaterial may be formed by additional polycondensation at vacuum pressure.

The itaconate monomers comprise methylated itaconate.

The diol monomers are any one or a combination of 1,6-hexanediol, 1,8-octanediol and 1,10-decanediol.

The administering step may comprise intraperitoneal injection.

The polyester biomaterial may further comprise second carboxylate monomers. The polyester biomaterial may be formed by forming a polyester backbone including the diol and the second carboxylate monomers, and reacting with the polyester backbone with the itaconate monomers.

The polyester biomaterial may be formed at atmospheric pressure at about 120° C.

The second carboxylate monomers may comprise citrate.

The polyester biomaterial may be poly(itaconate-co-citrate-co-octanediol).

The method may further comprise a step of moulding the polyester biomaterial into a scaffold for a tissue patch before the administrating step. The tissue patch may be a cardiac patch.

The present disclosure provides a biomaterial comprising poly(itaconate-co-citrate-co-octanediol). The biomaterial exhibits or has hydrolytic degradability. The biomaterial may have a tunable elasticity from about 0.05 to about 1.7 MPa The biomaterial has ability to crosslink under ultraviolet light with radical polymerization.

The biomaterial may be in a form of a scaffold for a tissue patch. The tissue patch may be a cardiac patch.

BRIEF DESCRIPTION OF THE DRAWINGS

Embodiments will now be described, by way of example only, with reference to the drawings, in which:

FIG. 1A shows general synthesis scheme for an ITA containing polyester using dimethyl itaconate with alcohols under with a radical inhibitor and tin based catalyst and FIG.

1B shows images of synthesized ITA polyesters with (I) 1,6-hexanediol (II) 1,8-octanediol (OD), or (III) 1,10-decanediol (DD).

Figure 2A:
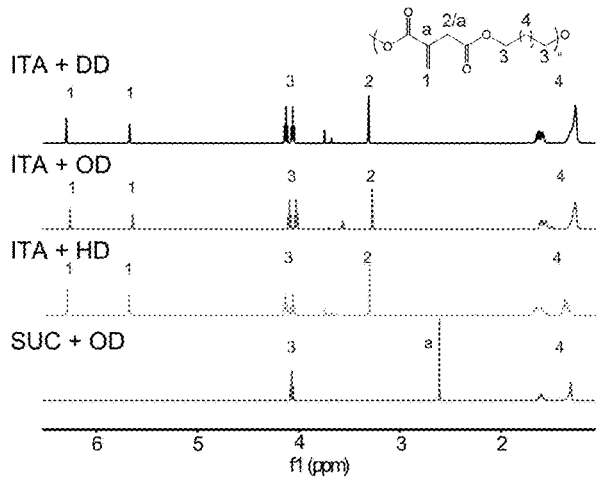
Figure 2B:
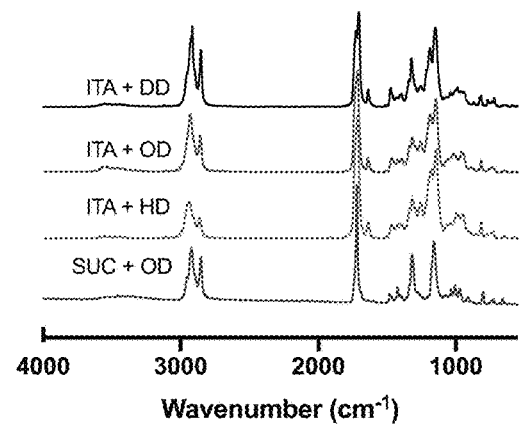
Figure 2C:
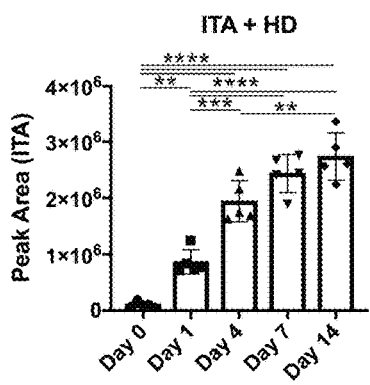
Figure 2D:
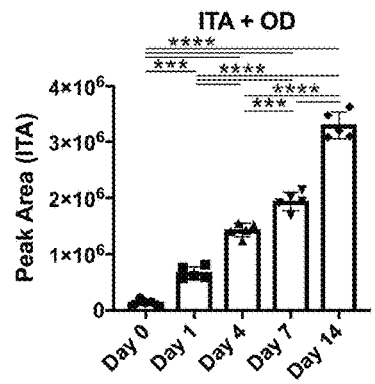
Figure 2E:
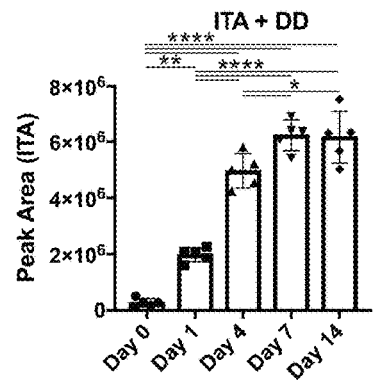
Figure 2F:
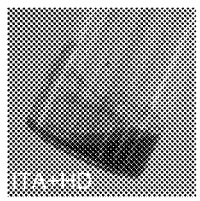
Figure 2G:
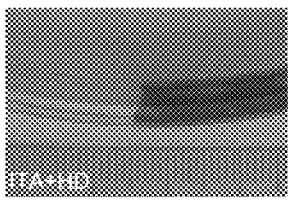
Figure 2H:
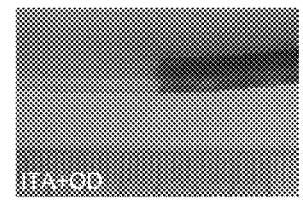
Figure 2K:
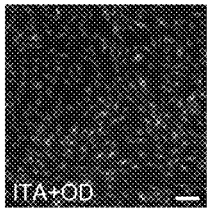
Figure 2I:
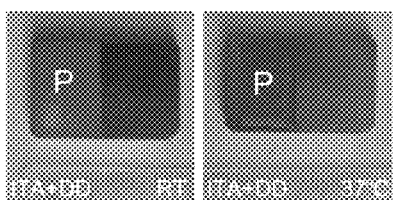
Figure 2J:
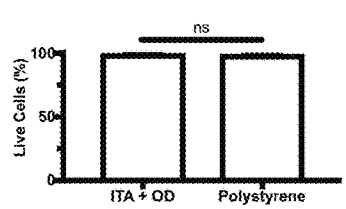
Figure 2L:
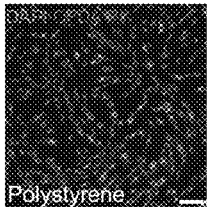

FIG. 2A to FIG. 2L show characterization of itaconate containing polyester materials with demonstrated molecular release, in which: FIG. 2A to FIG. 2B shows characterization of polymer purity and structure. Representative (FIG. 2A) $^1$HNMR and (FIG. 2B) FTIR spectra for ITA+DD, ITA+OD, ITA+HD and SUC+OD polyester, FIG. 2C to FIG. 2E demonstrate hydrolytic release of ITA from material backbones. Integrated peak area of mass spectrometry assessment for ITA presence in hydrolytic degradation supernatant extracts for (FIG. 2C) ITA+HD, (FIG. 2D) ITA+OD, and (FIG. 2E) ITA+DD. Data is mean±SD, n=4. One way ANOVA followed by pairwise comparison with Tukey's multiple comparisons test, FIG. 2F to FIG. 2I demonstrate ITA containing material coating onto common medical devices surfaces. FIG. 2F shows ITA+HD was visualized with solubilized Sudan Red, and the (FIG. 2G) ITA+HD and (FIG. 2H) similarly prepared ITA+OD were coated onto PVC tubing (ID: ⅛", OD: ¼" (FIG. 2G), OD: ³⁄₁₆" (FIG. 2H)). (FIG. 2I) ITA+DD was solvent cast onto the surface of medical grade titanium alloy as a solid (room temperature), becoming gel form at physiologically relevant temperature (37° C.). Scale: 1 mm per notch, P indicates polymer coating. FIG. 2J to FIG. 2L show culture of dermal fibroblasts on ITA+OD presents similar cellular behaviour to polystyrene controls. FIG. 2J shows quantified percent of viable dermal fibroblasts 2 days post seeding. Data is mean±SD, n=6. Student t-test. Representative fluorescent images of dermal fibroblasts attachment on (FIG. 2K) ITA+OD polymer-coated well (2 d post-seeding) and (FIG. 2L) tissue culture polystyrene control 2 d post-seeding. Green: CFSA-SE (Live Cells), Red: PI (dead cells), Blue: DAPI (cell nuclei). Scale bars: 150 µm. Statistical significance is indicated as *p<0.05  p<0.01, * p<0.001, **** p<0.0001, ns=non-significant.

Figure 3A:
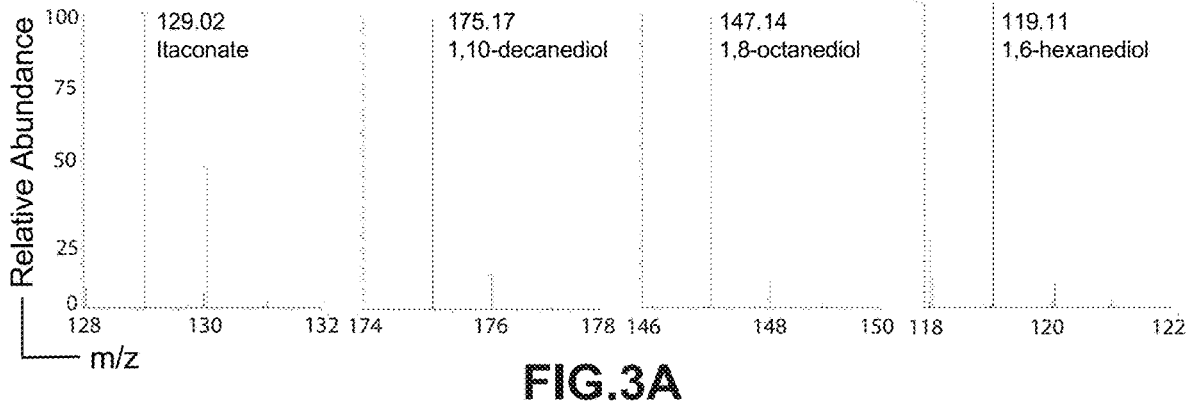
Figure 3B:
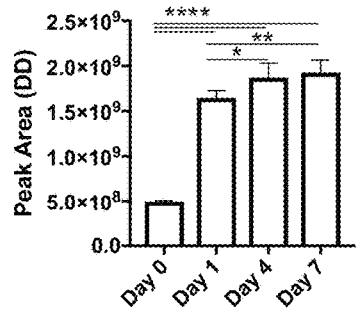
Figure 3C:
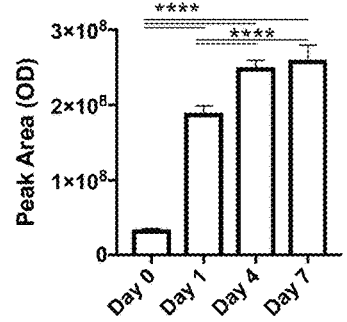
Figure 3D:
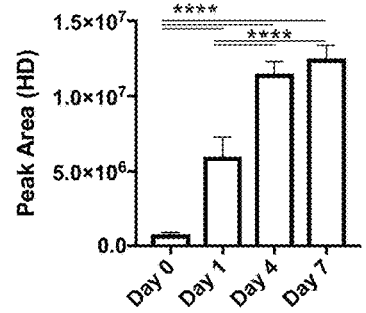
Figure 3E:
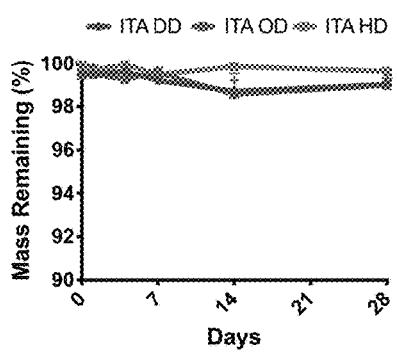
Figure 3F:
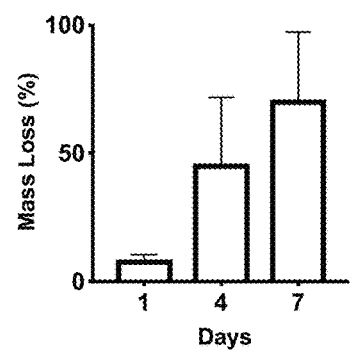
Figure 3G:
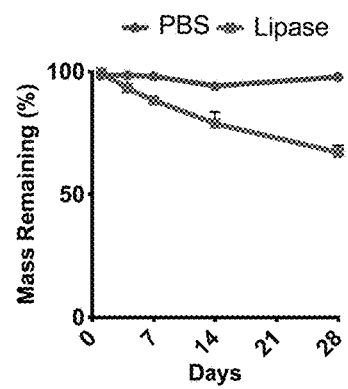

FIG. 3A to FIG. 3G show degradation behavior of itaconate containing materials in which: FIG. 3A shows representative peak identification of ITA, HD, OD, and DD in mass spectroscopy (m/z) spectra, FIG. 3B, FIG. 3C and FIG. 3D show integrated peak area for (FIG. 3B) HD, (FIG. 3C) OD, and (FIG. 3D) DD in hydrolytic degradation supernatant extracts for ITA+HD, ITA+OD, and ITA+DD respectively. Data is mean±SD, n=4. One way ANOVA followed by pairwise comparison with Tukey's multiple comparisons test. Statistical significance is indicated as *p<0.05  p<0.01, * p<0.001, **** p<0.0001. FIG. 3E shows hydrolytic degradation of ITA containing polyesters in DPBS over 28 days, FIG. 3F and FIG. 3G show accelerated degradation of: FIG. 3F ITA+OD under basic conditions (1M) and FIG. 3G ITA+DD in the presence of lipase.

Figure 4A:
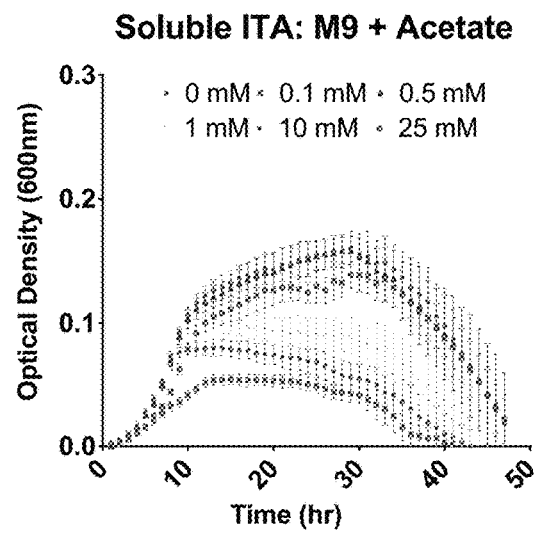
Figure 4B:
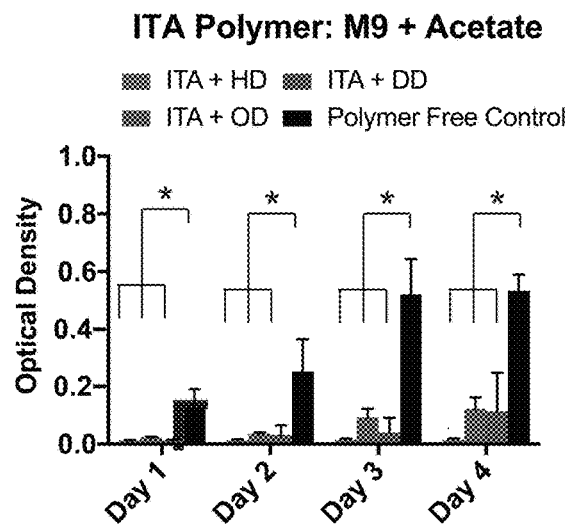
Figure 4C:
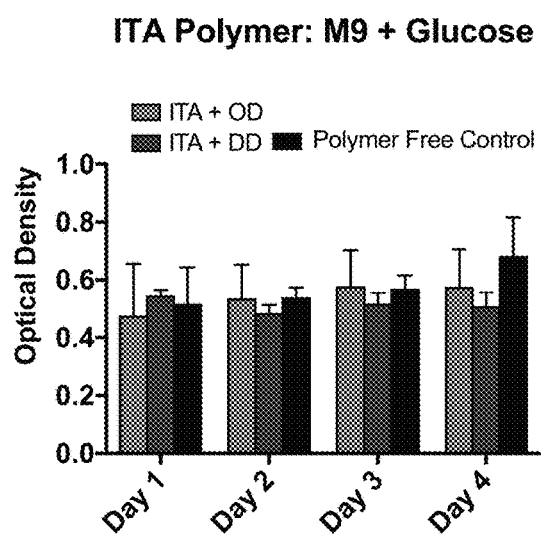
Figure 4D:
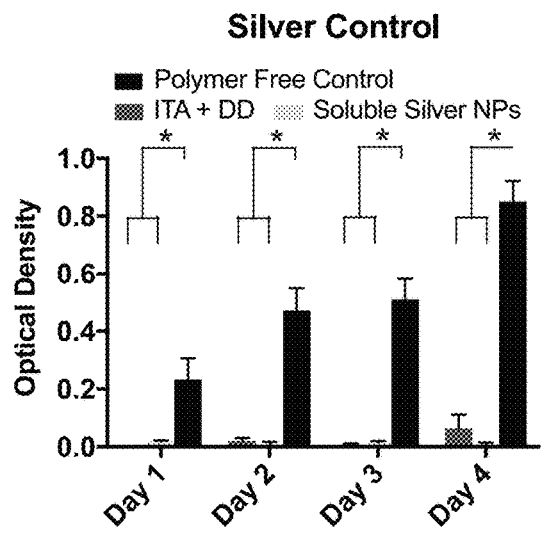
Figure 4G:
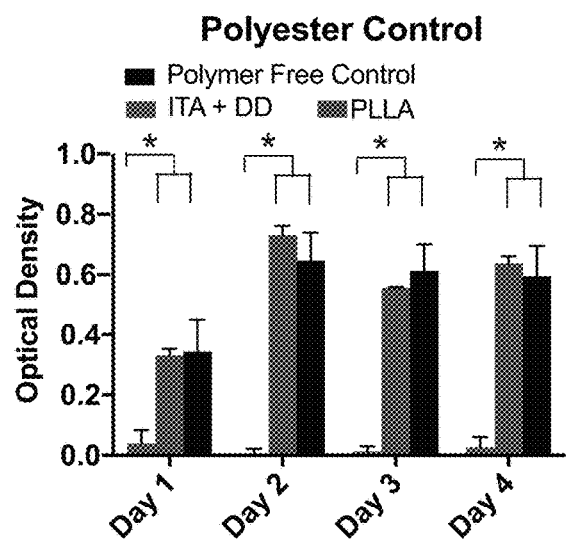
Figure 4G:
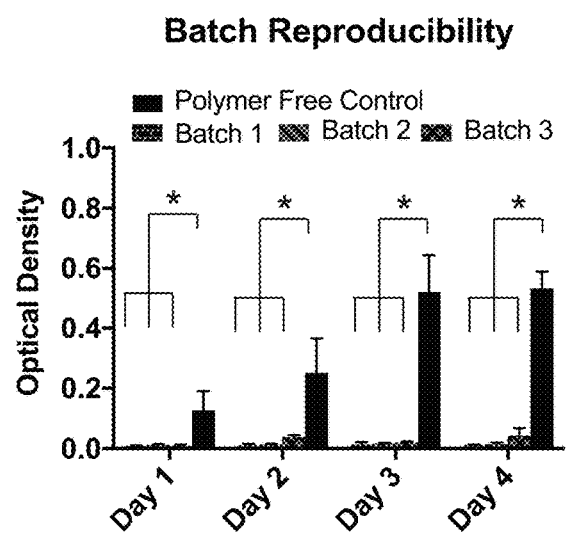
Figure 4G:
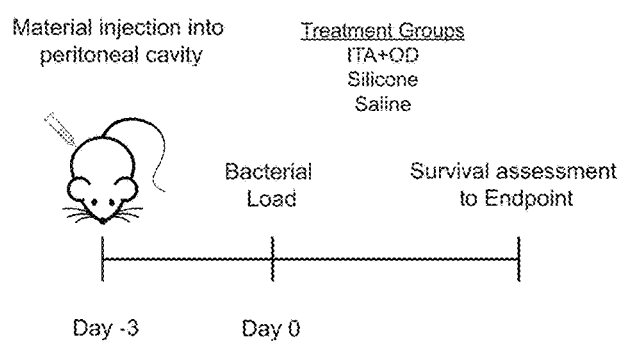
Figure 4G:
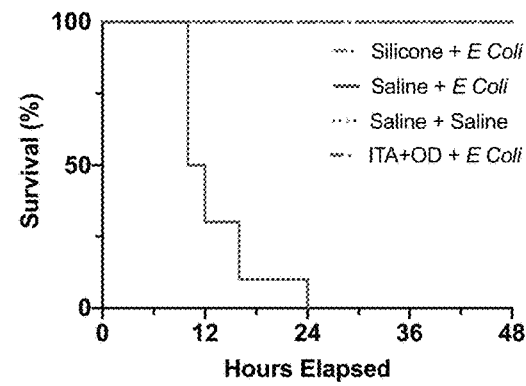

FIG. 4A to FIG. 4G show itaconic acid (ITA) based polyesters inhibit bacterial growth, in which FIG. 4A shows soluble ITA inhibition of E. coli growth below 1 mM concentration with an acetate carbon source, FIG. 4B to FIG. 4F show liquid culture growth inhibition of E. coli cultured with ITA polymer materials (*p<0.05). FIG. 4B shows ITA+HD, ITA+OD, and ITA+DD growth inhibition on acetate in comparison to a polymer-free growth control, whereas FIG. 4C shows growth on a glucose source indicated no appreciable inhibition, FIG. 4D shows ITA+DD performed similar inhibition to silver nanoparticles and FIG. 4E provided improved inhibition compared to a PLLA degradable polyester analogue (acetate source), FIG. 4F shows inhibition results remained consistent across multiple synthesis batches of ITA+HD, suggesting the reproducibility of antimicrobial efficacy. Data is mean±SD, n≥3. One way ANOVA followed by pairwise comparison with Tukey's multiple comparisons test. Statistical significance is indicated as *p<0.05. FIG. 4G presents ITA containing polyester gel prevent infection-based lethality. Mice injected with ITA+OD, silicone or saline (n=10) three days prior to E. coli bacterial loading present differential survival characteristics. Saline+saline control (n=5) received saline three days prior and saline at time of infection loading.

Figure 5A:
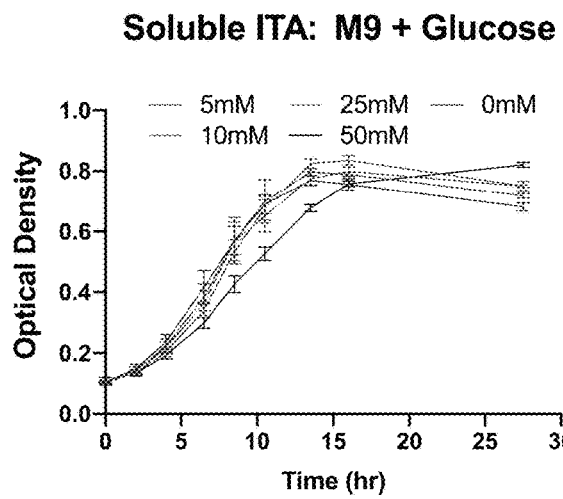
Figure 5B:
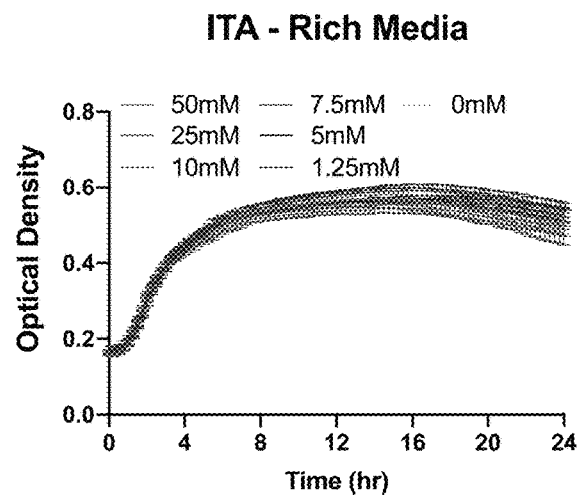
Figure 5C:
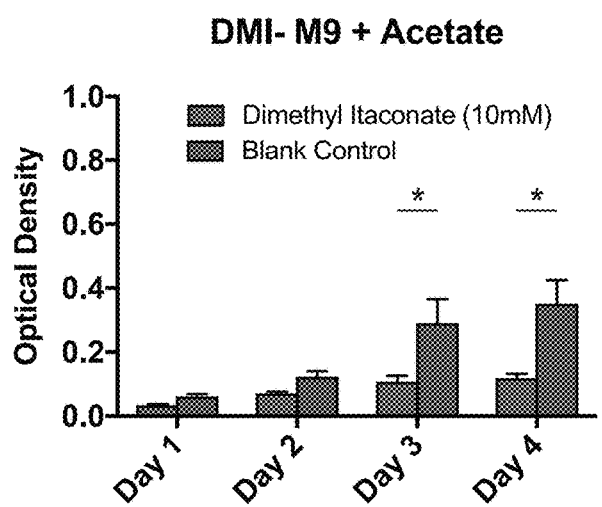
Figure 5D:
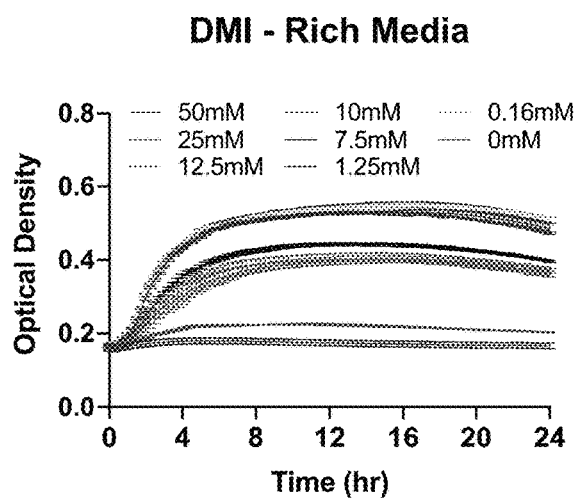
Figure 5E:
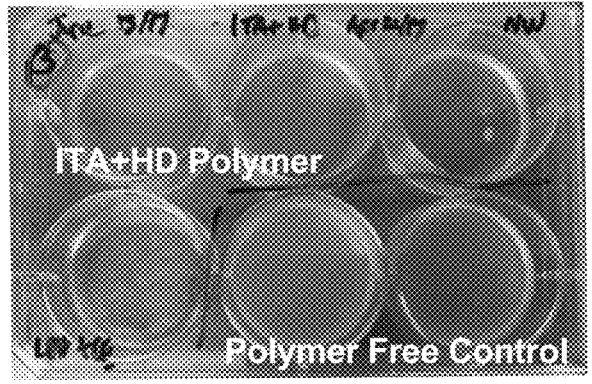
Figure 5F:
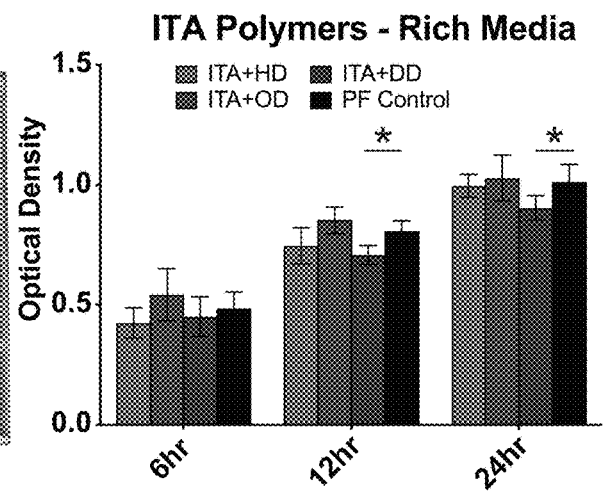
Figure 5G:
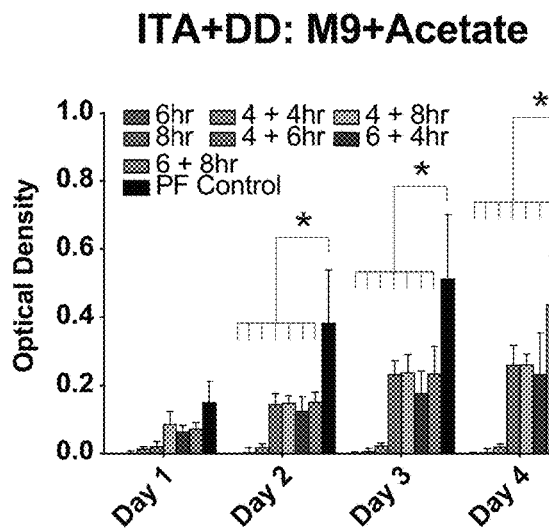
Figure 5H:
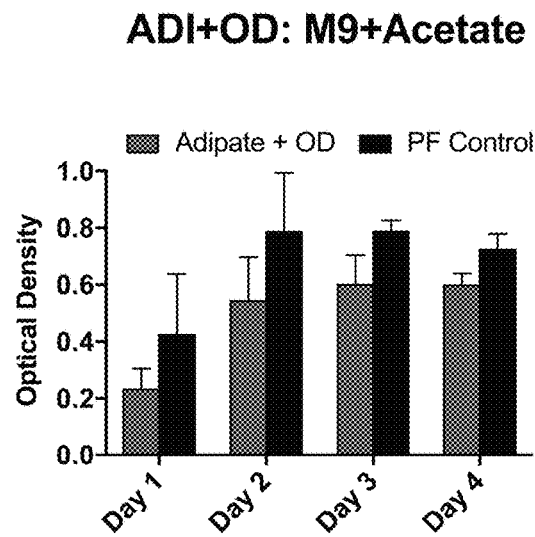

FIG. 5A to FIG. 5H show itaconate polymers present growth specific E. coli inhibition, in which: FIG. 5A to FIG. 5D show soluble itaconate inhibition under different media conditions. Solubilized itaconate (up to 50 mM) did not impact growth; FIG. 5A shows no change of growth with minimal M9 media with a glucose carbon source or and FIG. 5B shows no change in growth on LB Broth. FIG. 5C to FIG. 5D show dimethyl itaconate exhibited more pronounced inhibition, FIG. 5C demonstrates inhibition with growth on LB broth (above 7.5 mM) and FIG. 5D presents inhibition comparable to solubilized itaconate under acetate growth conditions in M9 media. FIG. 5E shows an image of experimental setup used for inhibition assessment. FIG. 5F shows a culture of ITA containing materials in LB broth did not exhibit appreciable growth inhibition. FIG. 5G shows inhibition was demonstrated across a range of ITA+DD synthesis times (x+y hr indicates x: time at 1 atm, y: time at vacuum pressure), with more pronounced inhibition with lower reaction time (acetate growth substrate). FIG. 5H shows inhibition was not observed with substitution of itaconate with adipate in the synthesis method. Data is mean±SD, n≥3. One way ANOVA followed by pairwise comparison with Tukey's multiple comparisons test. Statistical significance is indicated as *p<0.05.

Figure 6A:
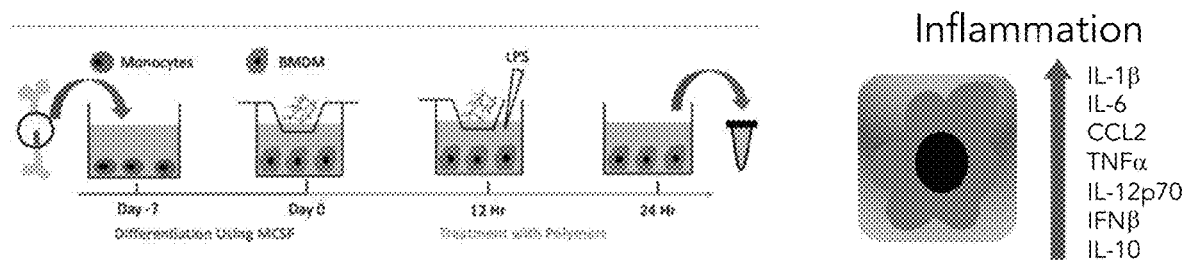
Figure 6B:
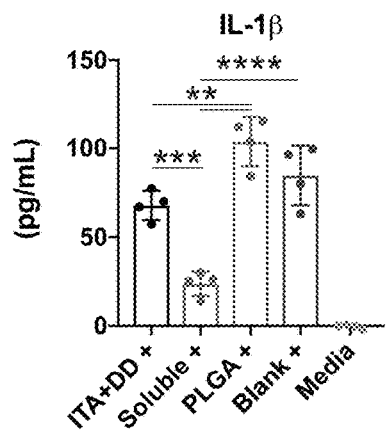
Figure 6C:
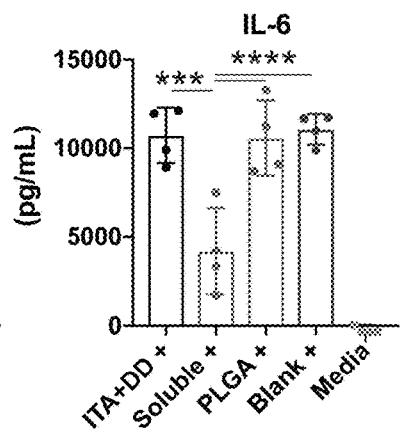
Figure 6D:
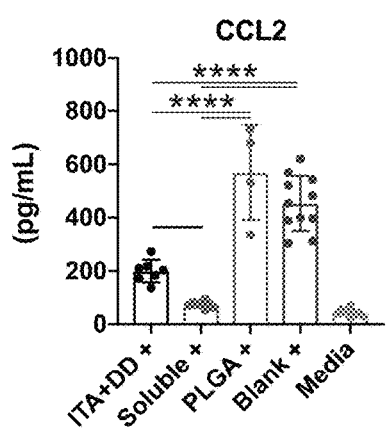
Figure 6E:
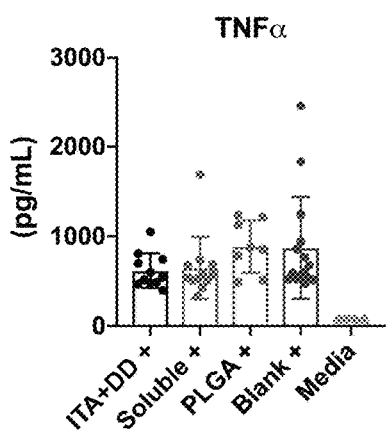
Figure 6F:
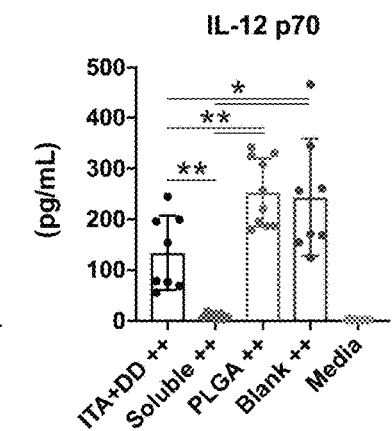
Figure 6G:
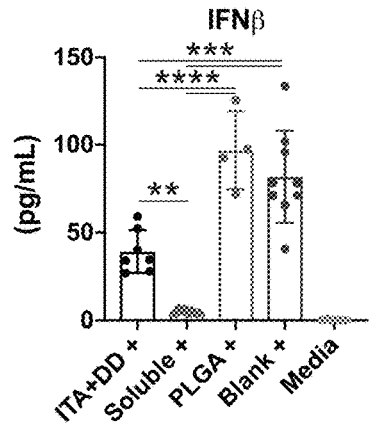
Figure 6H:
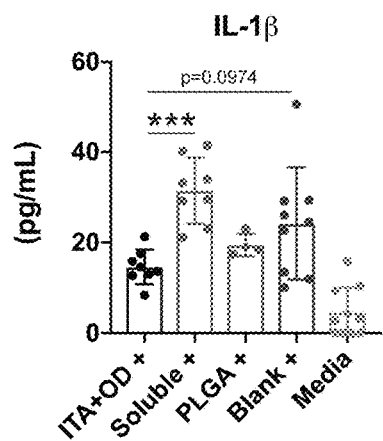
Figure 6I:
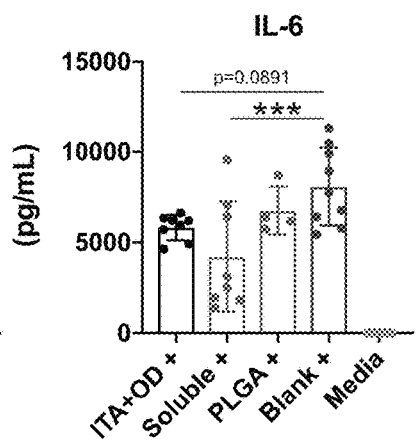
Figure 6J:
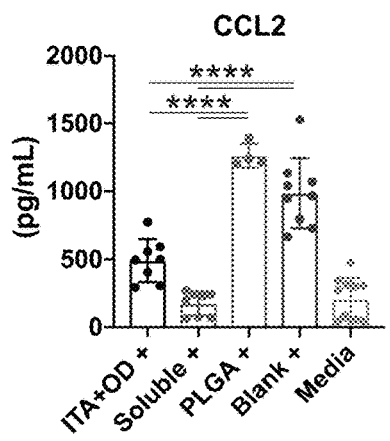
Figure 6K:
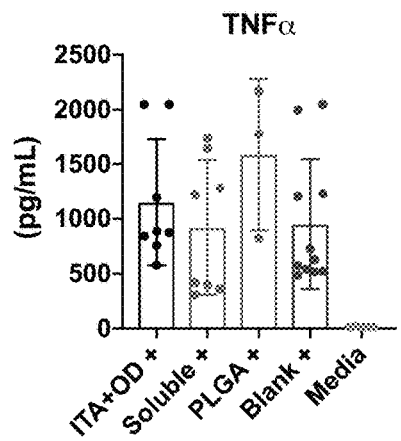
Figure 6L:
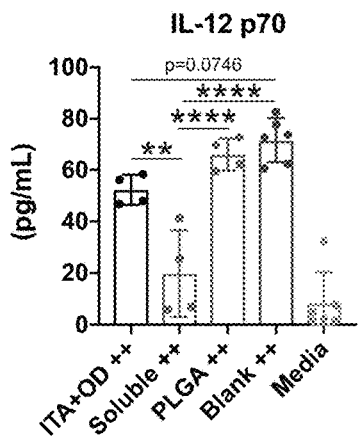
Figure 6M:
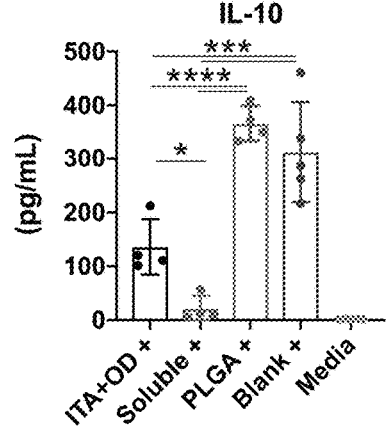

FIG. 6A to FIG. 6M show itaconate containing materials modulate macrophage cytokine inflammatory response, in which: FIG. 6A shows a schematic of experimental protocol for the generation and assessment of polymer immunomodulation behavior with murine bone marrow derived macrophages in vitro, FIG. 6B to FIG. 6M shows inflammatory cytokine quantification for key markers in innate immunity. Culture with ITA+DD (FIG. 6B to FIG. 6G) and ITA+OD (FIG. 6H to FIG. 6M) material with soluble DMI comparison demonstrated a downregulation of IL-1β (FIG. 6B, FIG. 6H), IL-6 (FIG. 6C, FIG. 6I), CCL2 (FIG. 6D, FIG. 6J), IL-12p70 (FIG. 6F, FIG. 6L), IFNβ (FIG. 6G), and IL-10 (FIG. 6M) with maintenance of TNFα expression (FIG. 6E, FIG. 6K) when compared to PLGA inserts and insert free controls. + indicates stimulation with LPS (100 ng/mL), ++ indicates stimulation with LPS (100 ng/mL) and IFNγ (50 ng/mL). Data is mean±SD, n≥4. One way ANOVA followed by pairwise comparison with Tukey's multiple comparisons test. Statistical significance is indicated as *p<0.05  p<0.01, * p<0.001, **** p<0.0001.

FIG. 7A to FIG. 7I show in vitro culture of itaconate materials with bone marrow derived macrophages presents repeatable immune modulation, in which: FIG. 7A shows images of experimental setup, polymer was coated on 18 mm glass coverslips and submerged in media wells (6 well culture plate) using transwell inserts, FIG. 7B shows the quantification of lactate dehydrogenase release from BMDM cultured with the conditions assessed in inflammatory experiments, FIG. 7C shows bright field images of stimulated BMDM cells (LPS: 100 ng/mL) cultured with ITA+DD compared to a PLGA and insert free (Blank) control. Scale bar: 100 µm. FIG. 7D to FIG. 7I show inflammatory cytokine quantification for key markers in innate immunity when pretreated with itaconate containing materials (12 hr) followed by stimulation with LPS (100 ng/mL) compared to PLGA inserts and insert free controls. FIG. 7D shows pretreatment of BMDM with ITA+DD presents a downregulation of IL-10. FIG. 7E to FIG. 7I show pretreatment of ITA+HD presents a trend of downregulation in IL-1β (FIG. 7E), CCL2 (FIG. 7H), and IL-10 (FIG. 7I), without observed trend in IL-6 (FIG. 7G) or TNFα (FIG. 7F) expression. + indicates stimulation with LPS (100 ng/mL). Data is mean±SD, n≥3. One way ANOVA followed by pairwise comparison with Tukey's multiple comparisons test. Statistical significance is indicated as *p<0.05  p<0.01, * p<0.001, **** p<0.0001.

Figure 8A:
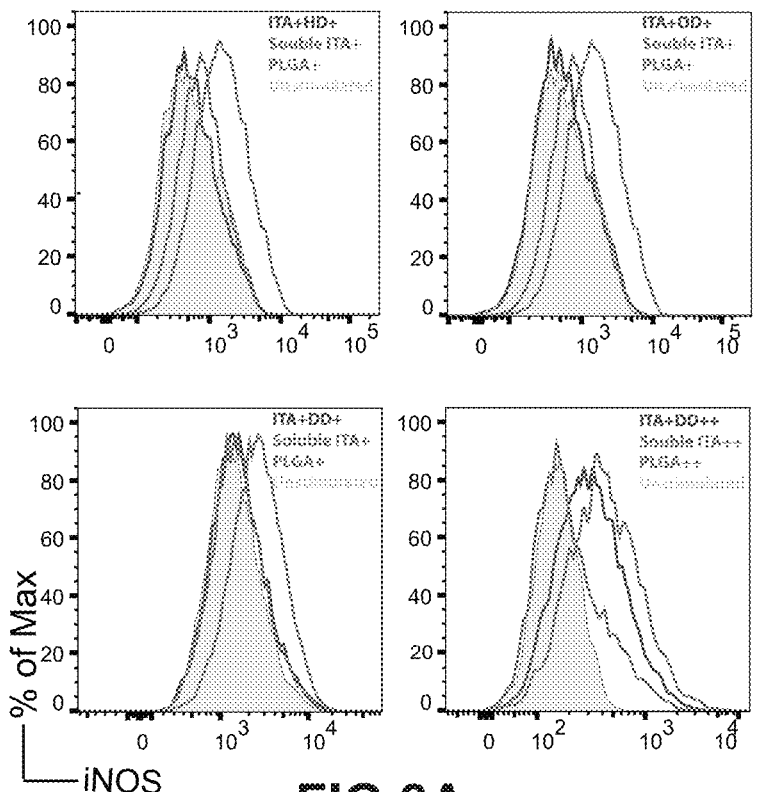
Figure 8B:
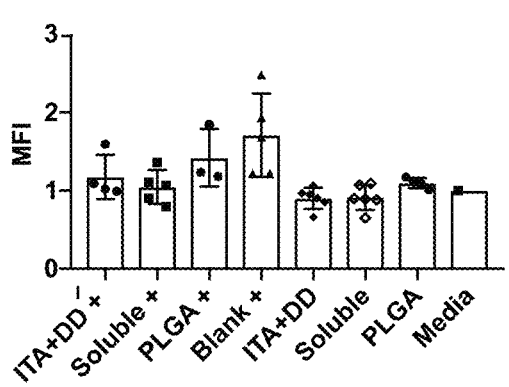
Figure 8C:
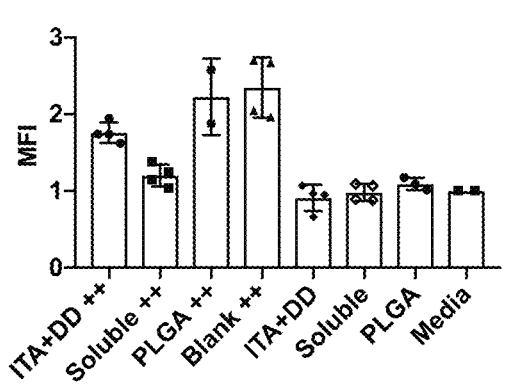
Figure 8D:
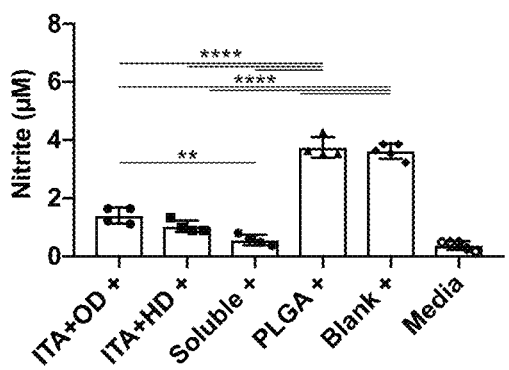
Figure 8E:
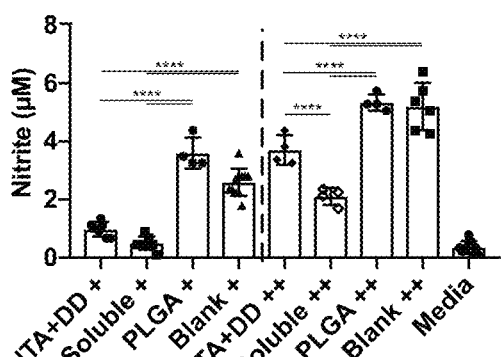

FIG. 8A to FIG. 8E show itaconate containing materials induce reduction in phenotypic inflammation, in which: FIG. 8A shows a representative histogram of fluorescence indicating expression of nitrate oxide synthase (NOS2) in response to stimulation (LPS or LPS/IFNγ) in cells pretreated with ITA+HD, ITA+OD, ITA+DD, soluble DMI, PLGA or insert free controls with an unstimulated reference, FIG. 8B to FIG. 8C show quantified median fluorescence intensity for NOS2 expression for cells pretreated (12 hr) with ITA+DD materials and stimulated with (FIG. 8B) LPS (100 ng/mL) or (FIG. 8C) LPS (100 ng/mL) and IFNγ (50 ng/ml) for 12(hr), FIG. 8D to FIG. 8E show supernatant nitrite content for (FIG. 8D) gel materials (ITA+HD, ITA+OD) stimulated with LPS and (FIG. 8E) ITA+DD stimulated with LPS (left) or LPS and IFNγ (right). + indicates stimulation with LPS (100 ng/mL), ++ indicates stimulation with LPS (100 ng/mL) and IFNγ (50 ng/mL). Data is (FIG. 8B-FIG. 8C) median±SD, n≥3, (FIG. 8D to FIG. 8E) mean±SD, n≥4. One way ANOVA followed by pairwise comparison with Tukey's multiple comparisons test. Statistical significance is indicated as *p<0.05  p<0.01, * p<0.001, **** p<0.0001.

Figure 9A:
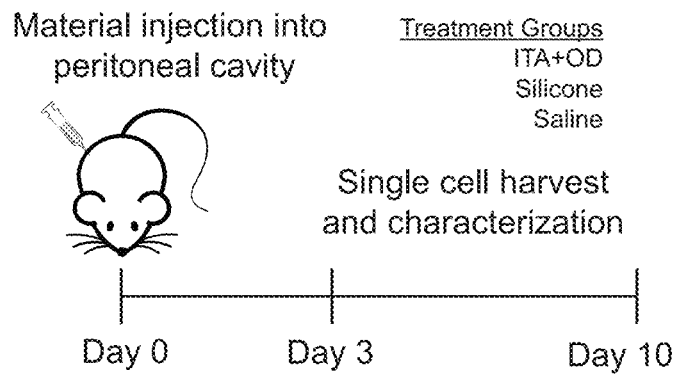
Figure 9B:
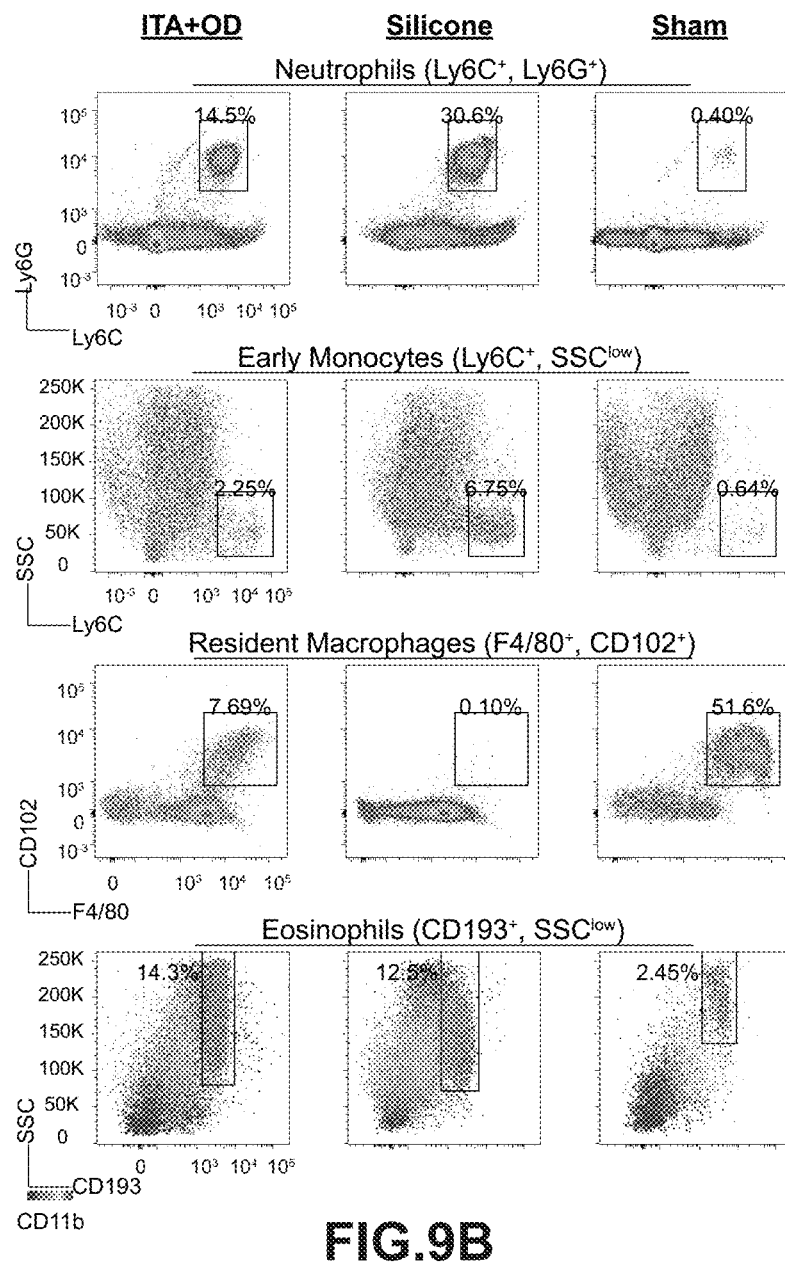

FIG. 9A to FIG. 9J show injectable itaconate gel material reduces biomaterial host response in a peritoneal infiltration model, in which: FIG. 9A shows an experimental schematic for peritoneal biomaterial associated immune cell infiltration model, FIG. 9B to FIG. 9J show, using flow cytometry assessment, quantified immune cell infiltration into the peritoneum following injection of ITA+OD (50 µL), hydroxy terminated polydimethylsiloxane (50 µL), or saline (Sham), with a comparable untreated group (Blank), FIG. 9B shows representative flow cytometry plots for ITA+OD (left), silicone (centre), and saline sham (right) ten days post injection, for which quantified cell populations were determined (FIG. 9E to FIG. 9F) three and (FIG. 9G to FIG. 9J) ten days post injection; at each timepoint, we quantified (FIG. 9C, FIG. 9G) neutrophil, (FIG. 9D, FIG. 9H) early monocyte, (FIG. 9E, FIG. 9I) eosinophil and (FIG. 9F, FIG. 9J) resident macrophage populations. Data is mean±SD, n≥3. One way ANOVA followed by pairwise comparison with Tukey's multiple comparisons test. Statistical significance is indicated as *p<0.05  p<0.01, * p<0.001, **** p<0.0001.

Figure 10:
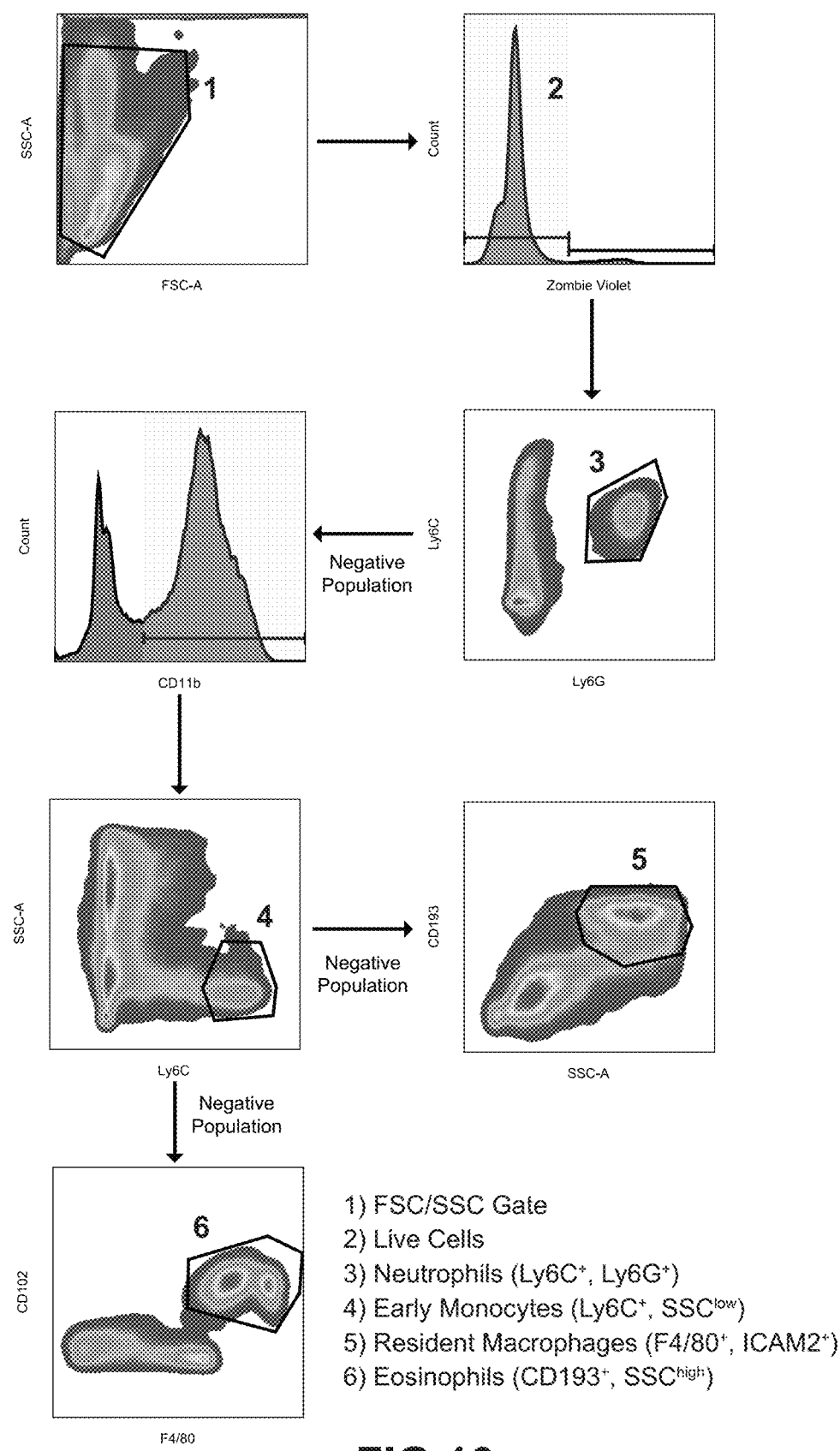

FIG. 10 shows gating strategy for single cell assessment of peritoneal immune cell infiltration.

Figure 11A:
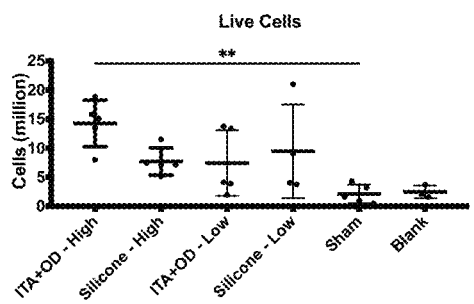
Figure 11B:
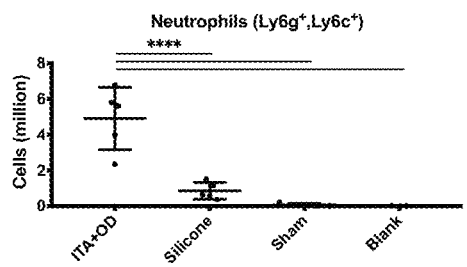
Figure 11C:
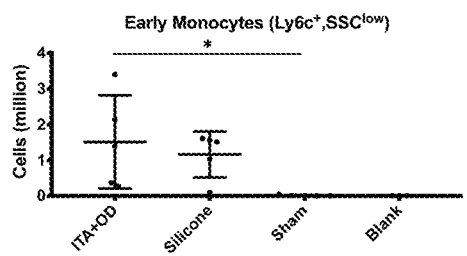
Figure 11D:
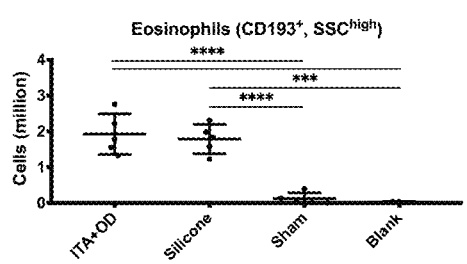
Figure 11E:
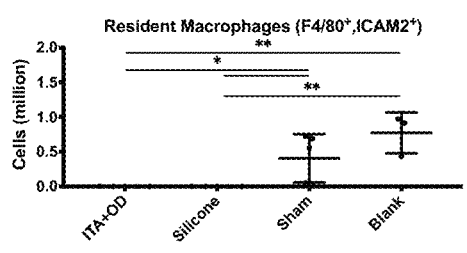
Figure 11F:
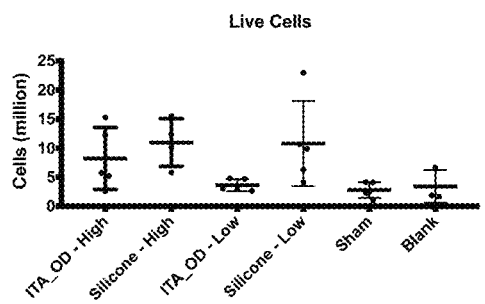
Figure 11G:
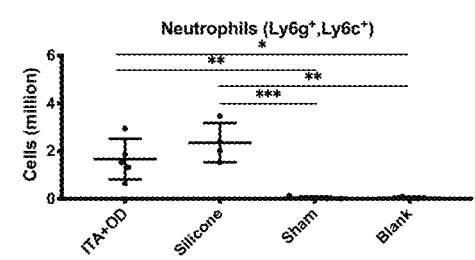
Figure 11H:
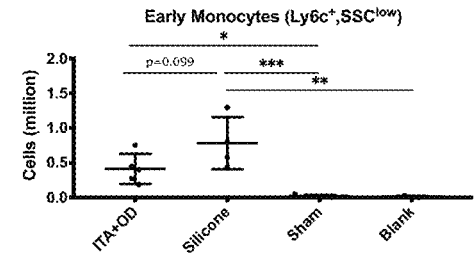
Figure 11I:
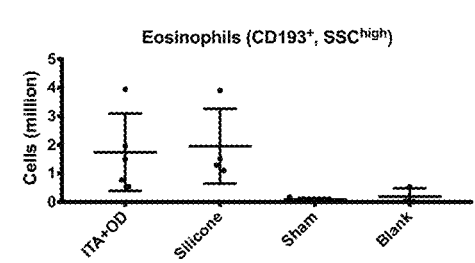
Figure 11J:
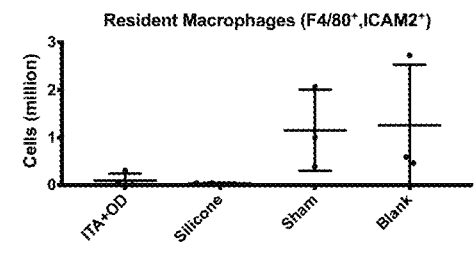

FIG. 11A to FIG. 11J show injectable itaconate gel exhibits a dose dependent biomaterial host response in a peritoneal infiltration model, in which: FIG. 11A to FIG. 11J show quantified assessment of single cell distribution, (FIG. 11A to FIG. 11E) three and (FIG. 11F to FIG. 11J) ten days post injection of ITA+OD or hydroxy terminated polydimethylsiloxane (High Dose: 150 µL, Low Dose: 50 µL), compared to saline sham (150 µL) and untreated controls (Blank), FIG. 11A, FIG. 11F show total live cell number post injection, FIG. 11B to FIG. 11E, FIG. 11G to FIG. 11J show quantified infiltration of (FIG. 11A, FIG. 11E) neutrophil, (FIG. 11B, FIG. 11F) early monocyte, (FIG. 11C, FIG. 11G) eosinophil and (FIG. 11D, FIG. 11H) resident macrophage populations with injection of a 150 µL dosage of biomaterial groups. Data is mean±SD, n≥3. One way ANOVA followed by pairwise comparison with Tukey's multiple comparisons test. Statistical significance is indicated as *p<0.05  p<0.01, * p<0.001, **** p<0.0001.

Figure 12:
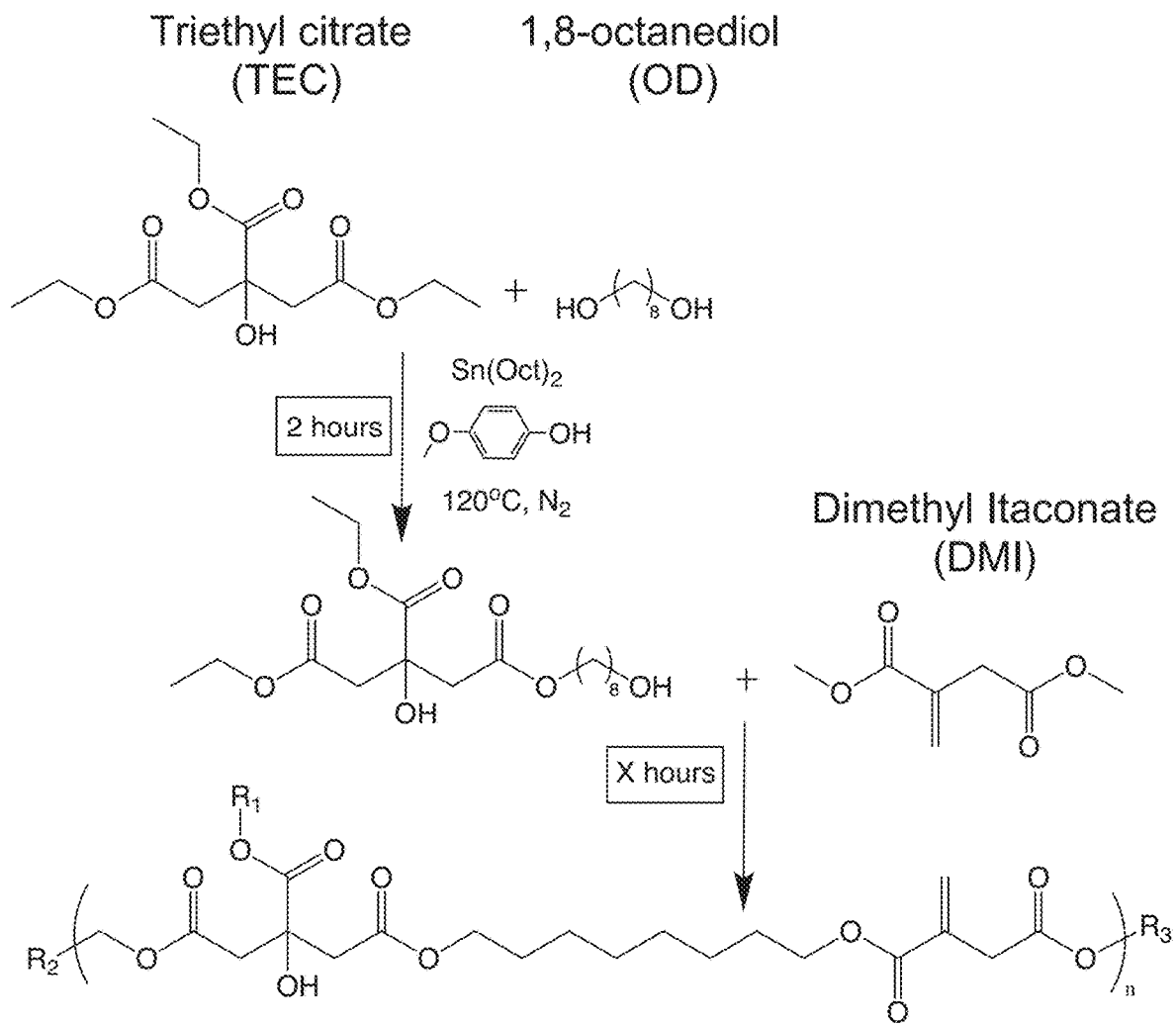

FIG. 12 shows general polycondensation synthesis scheme of PICO polymer materials.

Figure 13A:
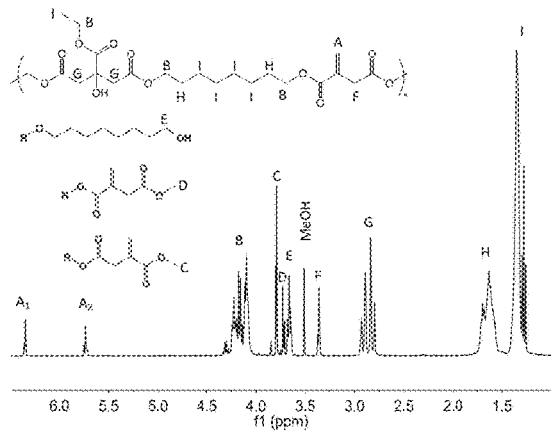
Figure 13B:
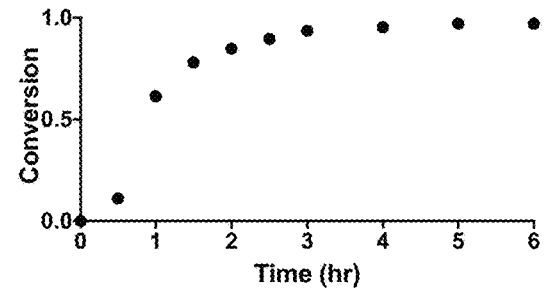
Figure 13C:
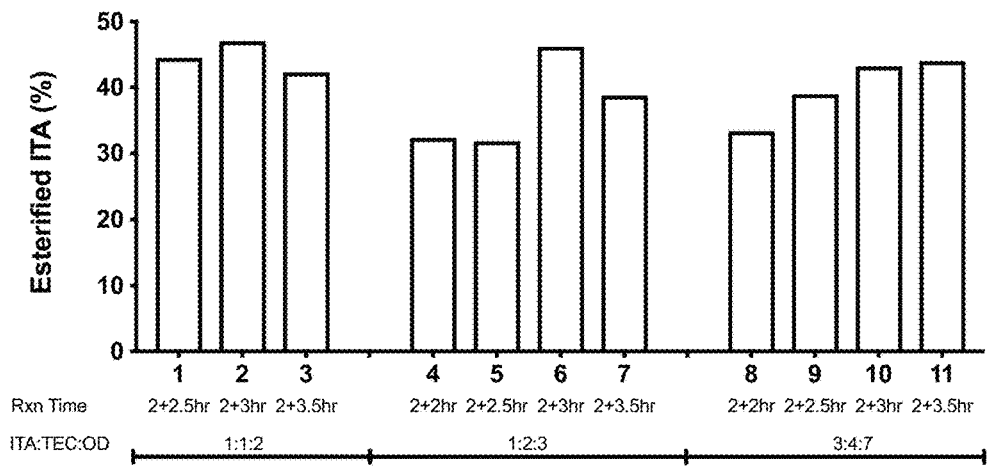
Figure 13D:
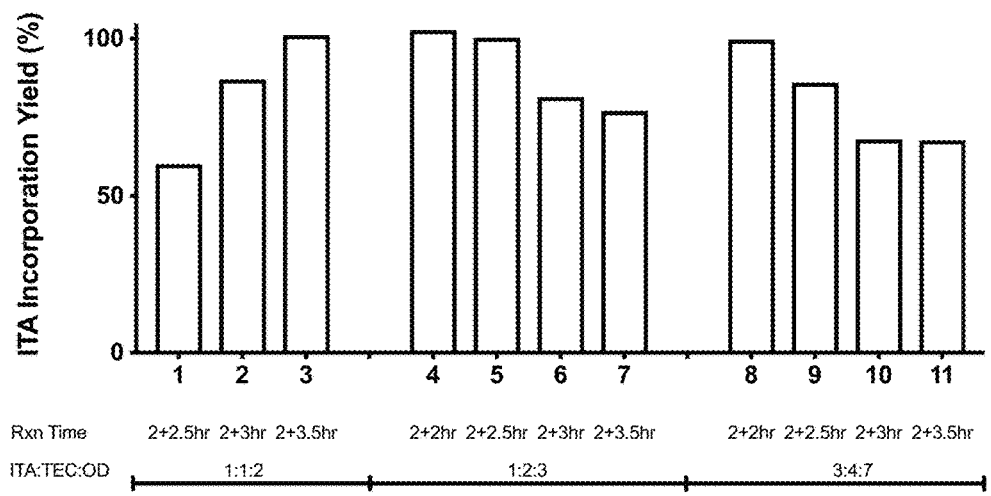

FIG. 13A to FIG. 13D show polymer composition and differential conversion, in which: FIG. 13A shows representative $^1$H-NMR spectra with labelled peaks according to molecules in the polymer backbone and monomer specific end groups, FIG. 13B shows conversion of OD into a TEC-OD (1:1 mol:mol) material over course of a 6 hour reaction, FIG. 13C to FIG. 13D show ITA incorporation into polymer materials in which FIG. 13C shows percentage of incorporated groups that are converted into ester bond, and FIG. 13D shows yield of expected ITA incorporation relative to OD basis.

Figure 14A:
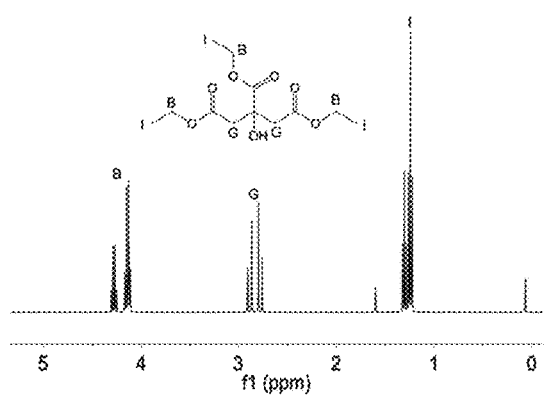
Figure 14B:
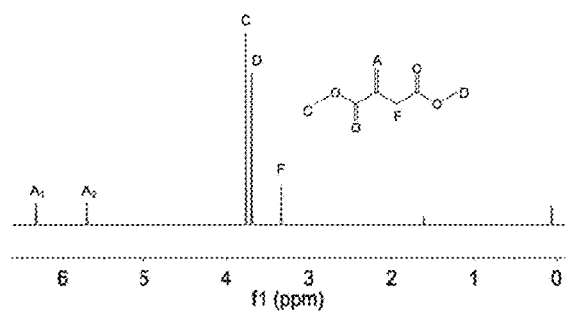
Figure 14C:
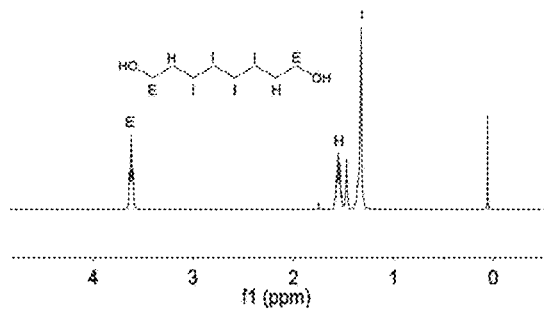
Figure 14D:
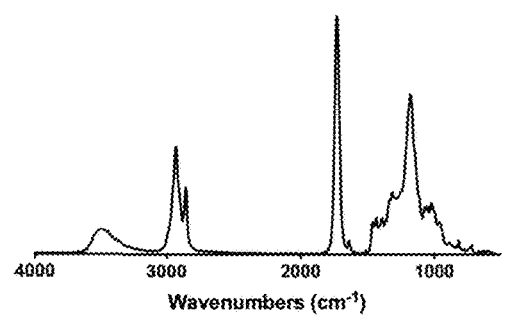

FIG. 14A to FIG. 14D show PICO materials prepolymer composition, in which: FIG. 14A to FIG. 14C show representative $^1$H NMR spectrum PICO monomers: (FIG. 14A) triethyl citrate (FIG. 14B) dimethyl itaconate, and (FIG. 14C) 1,8-octanediol, and 14D shows representative FTIR spectra of PICO gel prepolymer.

FIG. 15A to FIG. 15D show gelation time is tunable according to polymer composition, in which: FIG. 15A to FIG. 15C shows time sweep measurement of storage (G') (●) and loss (G") (■) modulus with exposure to UV light (illuminated at t=100 s, indicated by the vertical dashed line) to present gelation characteristics. PICO with (FIG. 15A) high, (FIG. 15B) low, and (FIG. 15C) moderate DMI monomer feed (ITA content) presented a modulation in gelation with differentiating polymerization time, FIG. 15D shows summarized time to gelation post UV light illumination, defined as the crossover point of storage and loss modulus. No evident gelation was observed in Polymers 4, 5, and 8.

Figure 16A:
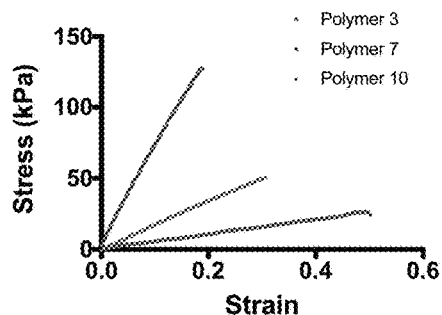

FIG. 16A to FIG. 16E show mechanical property characteristics of crosslinked polymer samples in which: FIG. 16A shows representative stress-strain curves of polymers with differing feed ratios, FIG. 16B to FIG. 16E shows comparative material properties of polymer groups exposed to 800 mJ of UV energy including (FIG. 16B) Young's Modulus (FIG. 16C) swelling in water (FIG. 16D) elongation at break, and (FIG. 16E) ultimate tensile strength (n=3). Statistics from two-way ANOVA are indicated in the tables (ns: non-significant difference). Significant differences between samples within the same feed ratio are defined as *p<0.05, p<0.001, *p<0.0001.

FIG. 17A to FIG. 17D show cyclic loading properties of PICO elastomers, in which: FIG. 17A shows representative cyclic tensile loading for polymer 10 over the first 10 cycles, FIG. 17B to FIG. 17D show stress-strain curves for cyclic tensile test at increasing cycles up to 1500 cycles for crosslinked samples of Polymer 2 (FIG. 17B), 6 (FIG. 17C), and 10 (FIG. 17D).

Figure 18A:
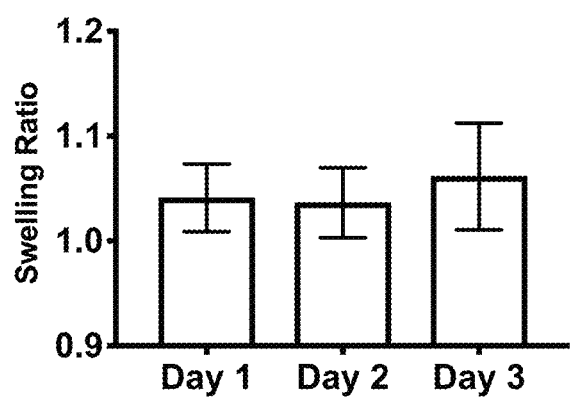
Figure 18B:
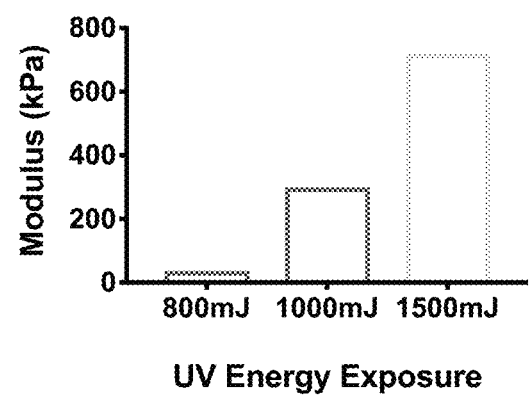

FIG. 18A and FIG. 18B show mechanical property characteristics of crosslinked polymer samples with variation in time, in which: FIG. 18A shows swelling of Polymer 10 crosslinked samples in water over three days. Assessment with One Way ANOVA indicated no significant differences. FIG. 18B shows modulation of Polymer 9 elasticity according to exposure energy.

Figure 19A:
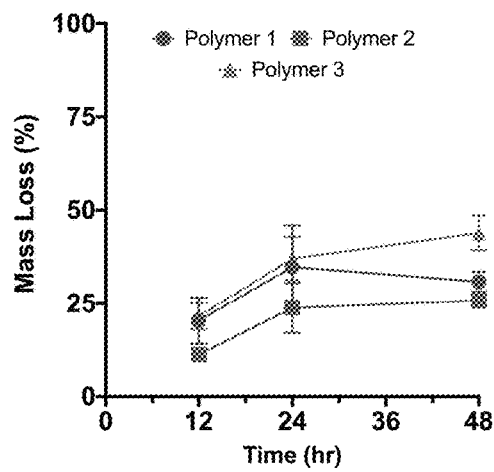
Figure 19B:
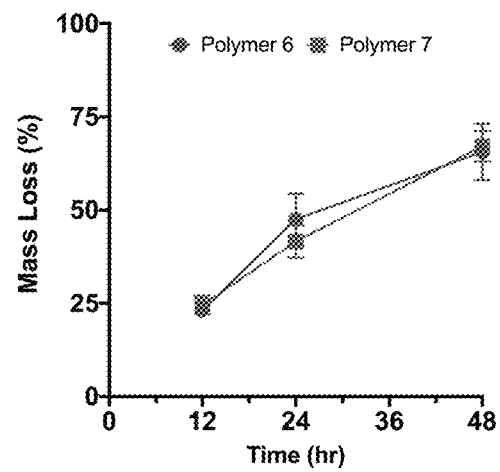
Figure 19C:
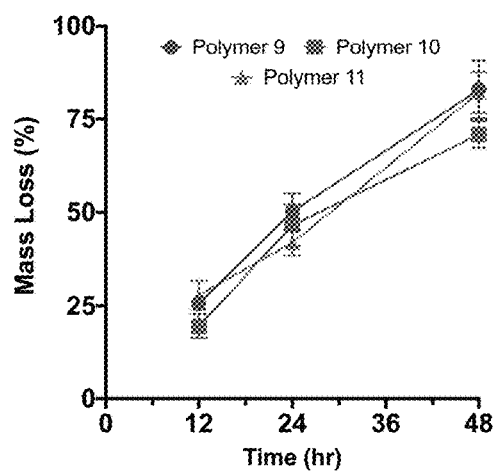

FIG. 19A to FIG. 19D show crosslinked polymer samples present differential degradation, in which: FIG. 19A to FIG.

Figure 19D:
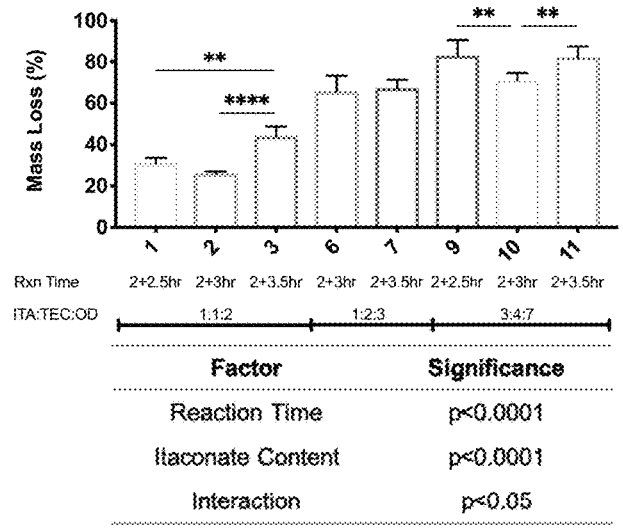

19C show accelerated (0.25M NaOH) degradation of UV crosslinked PICO materials with (FIG. 19A) high (FIG. 19B) low and (FIG. 19C) moderate DMI monomer feed (ITA content). FIG. 19D shows a comparison of mass loss of material groups with 48 hours of degradation. Two Way ANOVA presents significance of reaction time and ITA content on hydrolytic degradation of crosslinked materials. Statistics from two-way ANOVA are indicated in the tables (ns: non-significant difference). Data are presented as mean±SD, n=4. Significant differences between samples within the same monomeric feed ratio are defined as *p<0.05, p<0.001, *p<0.0001.

Figure 20A:
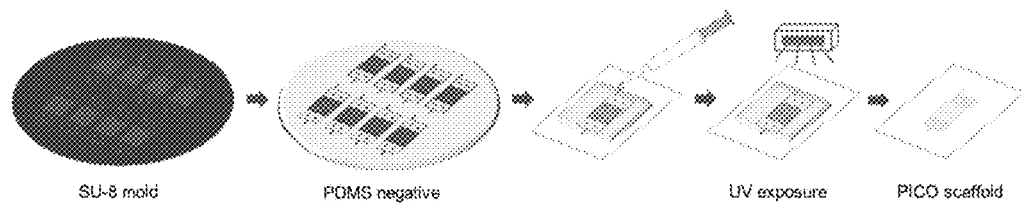
Figure 20B:
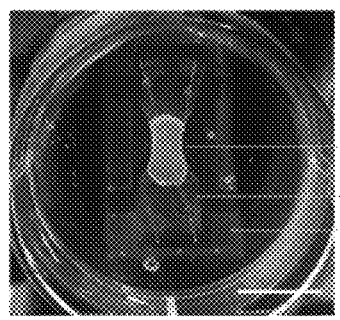
Figure 20D:
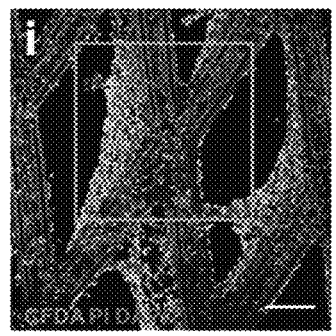
Figure 20E:
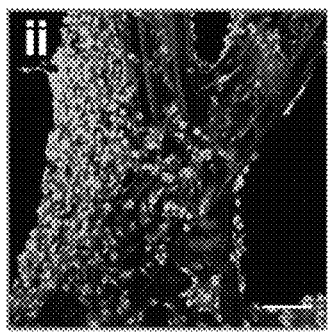
Figure 20C:
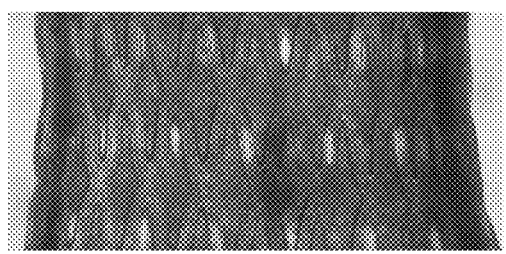
Figure 20F:
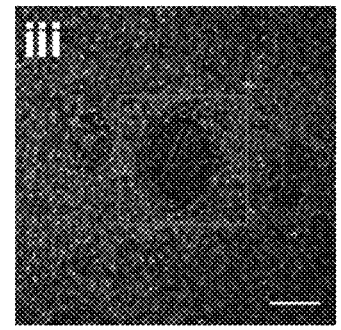
Figure 20G:
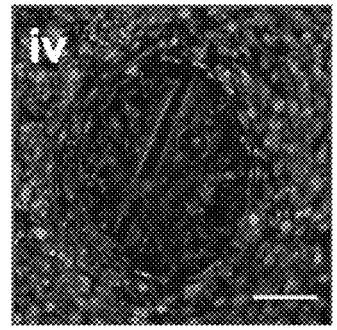
Figure 20H:
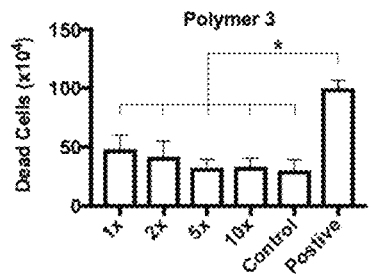
Figure 20H:
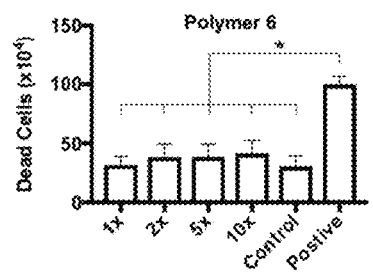
Figure 20H:
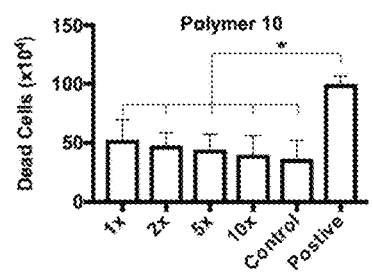

FIG. 20A to FIG. 20H show PICO polymer scaffold as cardiac patches in which: FIG. 20A shows a schematic representation of PICO scaffolds fabricated using microfabrication technology, FIG. 20B shows cardiac tissue cultured on PICO scaffolds affixed on holders in a tissue culture dish (Scale bar: 1 cm), FIG. 20C shows cardiac tissue compaction around PICO scaffolding in hydrogel ECM (Scale Bar: 500 µm), FIG. 20D to FIG. 20G shows fluorescence images of live (CFDA-SE: green) and dead (PI: red) rat neonatal CMs on PICO scaffolds. Low (FIG. 20D, FIG. 20E) and high (FIG. 20F, FIG. 20G) density constructs were visualized. Cell nuclei were also stained with DAPI (blue), and the scaffold exhibits autofluorescence in this channel. (Scale bars: FIG. 20D, FIG. 20F=200 µm, FIG. 20E, FIG. 20G=100 µm), FIG. 20H shows quantified cell death of cardiac fibroblasts cultured for 24 hours in dilutions of conditioned culture media treated with Polymers 3, 6, and 10 compared to the untreated culture media (Control) and a positive control media containing 10% Triton-X (Positive). Data are presented as mean±SD, n≥4. *p<0.05, One-way ANOVA followed by Dunnett's multiple comparisons test.

Figure 21A:
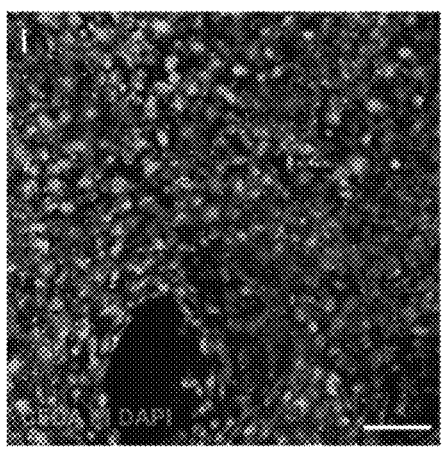
Figure 21B:
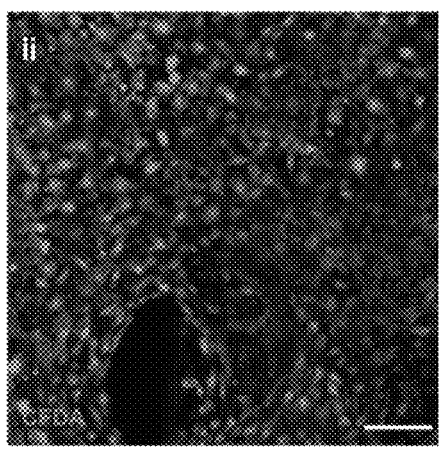
Figure 21C:
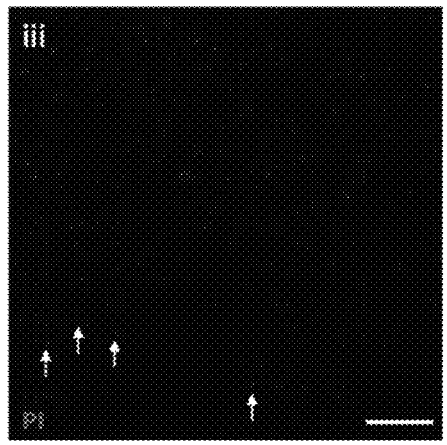
Figure 21D:
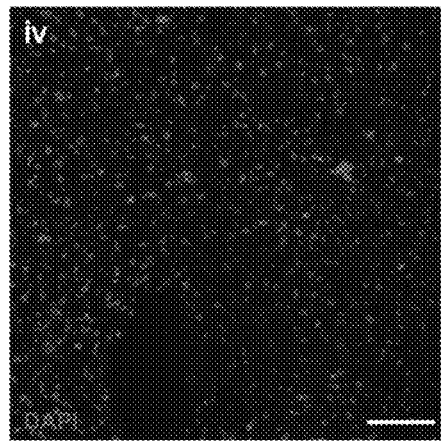

FIG. 21A to FIG. 21D show fluorescence images of high CM density PICO scaffold construct. FIG. 21A shows composite image of live (CFDA-SE: green) and dead (PI: red) stain of rat neonatal CMs. Cell nuclei were also stained with DAPI (blue), and the scaffold exhibits autofluorescence in this channel. FIG. 21B to FIG. 21D show single channel fluorescence images of the (FIG. 21B) green (CFDA), (FIG. 21C) red (PI), (FIG. 21D) and blue (DAPI) channels. Scale bars: 100 µm.

DETAILED DESCRIPTION OF THE EMBODIMENTS

Without limitation, the majority of the systems described herein are directed to a polyester biomaterial containing itaconate, and a method of treating infection and/or inflammation by administering the polyester biomaterial containing itaconate to a subject. As required, embodiments of the present invention are disclosed herein. However, the disclosed embodiments are merely exemplary, and it should be understood that the invention may be embodied in many various and alternative forms.

The accompanying figures, which are not necessarily drawn to scale, and which are incorporated into and form a part of the instant specification, illustrate several aspects and embodiments of the present disclosure and, together with the description therein, serve to explain the principles of the simulation apparatus. The drawings are provided only for the purpose of illustrating select embodiments of the apparatus and as an aid to understanding and are not to be construed as a definition of the limits of the present disclosure.

As used herein, the term "about", when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region. For example, in embodiments of the present invention dimensions, composition, and characteristics of components of a neck simulator may be given but it will be understood that these are not meant to be limiting.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Although successes are notable, the use of synthetic biomaterials have been limited by poor integration, fibrosis, bacterial colonization of implants and limited biocompatibility. Through a biomimetic approach, the present inventors have developed a library of polyester materials that incorporate a powerhouse innate mammalian cell immunity, itaconic acid (ITA), into polymer backbones for establishment of inherent antibacterial and anti-inflammatory characteristics. Using a one pot polycondensation reaction, the inventors optimized an adaptable synthesis method to combine ITA with different length alcohol monomers, yielding materials of high purity (1HNMR, FTIR) in gel (1,6-hexanediol, 1,8-octanediol), and solid form (1,10-decanediol). These constructs demonstrated quantifiable ITA release in a hydrolytic environment.

Multiple ITA containing material combinations demonstrated a decrease in *Escherichia coli* growth (p<0.05) when compared to a polystyrene and poly(L-lactic acid) (PLLA) groups, with comparable inhibition to commonly utilized silver nanoparticles. Pre-treatment of murine bone marrow derived macrophages (BMDMs) with ITA containing materials prior to pro-inflammatory stimulation (LPS, LPS/IFNγ) presented a significant down-regulation in a number of pro-inflammatory cytokines (IL-1β, IL-6, IL-10, IL-12p70, CCL2, IFNβ) and phenotypic nitric oxide production (NOS2 expression, nitrile secretion) when compared to poly(lactic-co-glycolic acid) (PLGA), suggesting release mediated anti-inflammatory characteristics.

Specificity of material cell functionality was verified by demonstrated non-toxic behaviour with human dermal fibroblasts. Upon peritoneal material injection, ITA containing gel material presented reduced biomaterial associated inflammation (neutrophils, monocytes, eosinophils; p<0.05) when compared to silicone ten days post-implant. The inventors have demonstrated a novel biomimetic approach where the inventors harness the advantages of the innate immunity, using a biomaterial design to incorporate bioactivity into polymer backbones, achieving localized antibacterial and anti-inflammatory material properties. These outcomes indicate the potential of ITA based material design as a platform of active material microenvironments with dual functionality for improvement of material adoption.

Results

Synthesis and Molecular Release from Itaconate Containing Polyesters

Figure 1A:
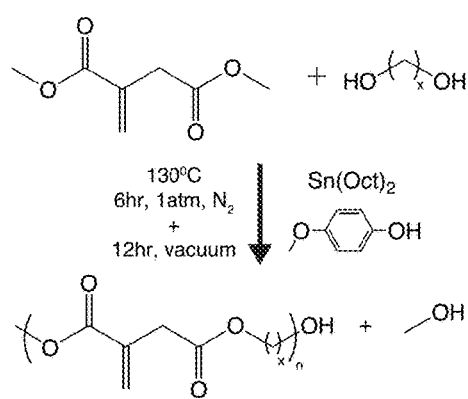
FIG. 1A and FIG. 1B show development of bioactive polyester materials that harness the power of itaconate innate immunity through small molecule degradation release.
Figure 1B:
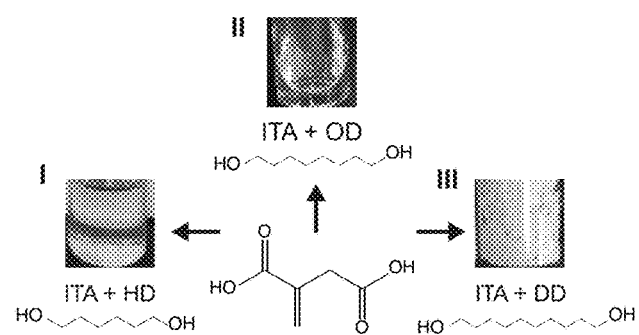

To create a biomaterial that can mimic some functions of the innate immunity and facilitate long-term delivery of ITA to the local cell microenvironment, we used polyester polymer synthesis techniques to incorporate the bioactive molecule into a hydrolytically degradable material. Given the reactivity of the pendant acrylate group on ITA, we employed a one-pot polycondensation with methylated carboxylate monomers (dimethyl itaconate, DMI) in the presence of a radical inhibitor (4-methoxyphenol, MEHQ) as descried previously[21] (FIG. 1A). Using this method, we have successfully synthesized new polyesters incorporating ITA into the polymer backbone, where we have coupled diols with ITA to generate long chain polyester materials. By varying the di-alcohol reacted with ITA, we have generated macroscopic gels, (poly[(itaconate)-co-(1,6-hexanediol)] (ITA+HD) and poly[(itaconate)-co-(1,8-octanediol)] (ITA+OD)), and solid ((poly[(itaconate)-co-(1,10-decanediol)] (ITA+DD)) materials (FIG. 1B).

Chemical structure assessment using proton nuclear magnetic resonance spectroscopy ($^1$HNMR) (FIG. 2A) and Fourier transform infrared spectroscopy (FTIR) (FIG. 2B) confirms polymer backbone structure and the presence of the ITA acrylate content when compared to succinate containing materials. Succinate, which lacks the acrylate group, was chosen as a representative control to synthesis efficacy given its similarity in backbone structure (i.e. four carbon carboxylate). Maintenance of this acrylate group is essential for polymer degradability and bioactivity, and the success of our synthesis method at accomplishing this was further confirmed by homogenous material appearance and solubility (soluble in non-polar solvent including chloroform and ethyl acetate). ITA+DD materials were solid at room temperature with a melting point of 30-32° C., much lower than polymers containing succinate, which were solid in appearance with high melting temperatures (data not shown), suggesting the alkene group on ITA impacts polymer chain molecular organization.

Hydrolytic degradation of ITA polyesters was evaluated to determine the release profile of ITA from material backbones. ITA was identified in the m/z spectrum of liquid chromatography-mass spectrometry (LC-MS) assessment of the degradation supernatant of ITA+HD, ITA+OD, and ITA+DD (FIG. 3A). Integration of peak area presents an increase in itaconate release over 14 days in all materials (FIG. 2C-E), with greater observed release in ITA+DD material (FIG. 2E). Corresponding diol release was increased over time proportionally to ITA, suggesting degradation release from the polymer backbones (FIG. 3B-FIG. 3D). Gross bulk mass loss was stable under hydrolytic conditions (1× PBS; <2% over 28 d) (FIG. 3E) but was accelerated under basic conditions (ITA+OD, 1M NaOH) (FIG. 3F) and in the presence of lipase (ITA+DD) (FIG. 3G), suggesting material susceptibility to hydrolytic and enzymatic degradation.

Specificity and Application of Material Constructs

As described, the one-pot synthesis method employed here allows for incorporation of ITA with various alcohols for generation of different material properties. Herein, we focused on linear materials for simplicity of assessment of material functionality. In application, gel materials (mixed with Sudan Red for visualization); ITA+HD (FIG. 2F, FIG. 2G) and ITA+OD (FIG. 2H) can surface coat commonly used medical tubing. ITA+DD was solvent cast onto medical grade metal implants at room temperature, presenting stability for storage, and becomes a gel when heated to body temperature (37° C.) (FIG. 2I). The modulatory behavior of released ITA did not provide a demonstrated impact on cell viability of human dermal fibroblasts, after two days of culture, quantified by immunostaining (live: CFDA-SE, dead: PI; FIG. 2J). Representative images of cells seeded on ITA+OD (FIG. 2K) and stained for viability markers present no marked difference from tissue culture polystyrene controls (FIG. 2L). This suggests that ITA release is non-impacting on general mammalian cell behavior and supports the specificity of biomaterial activity on immune modulation and infection prevention in potential applications.

Inhibitory Behavior of Itaconate Materials on *Escherichia coli* Growth

With the establishment of degradable ITA polyester materials, we assessed the translation of biomimetic antimicrobial efficacy of ITA containing polymers in vitro. It has been shown previously that ITA is a potent inhibitor of ICL, a key enzyme in the glyoxylate shunt that is necessary for bacterial growth on complex 2-carbon substrates (i.e. acetate)[10, 11]. Therefore, we considered the benchmark for in vitro material efficacy to be specific growth inhibition in minimal media (M9) with an acetate carbon source (1% m/v). Culture of *Escherichia coli* with solubilized ITA under these conditions yielded growth inhibition as low as 1 mM concentration (measured by OD: 600 nm) (FIG. 4A). This inhibition was not observed with a glucose carbon source (0.4% m/v) (FIG. 5A), or on rich media (LB broth) (FIG. 5B), consistent with previously observed inhibition specificity[22]. Culture with solubilized DMI, a polymer mimic (methylated ITA), presented similar effects on bacterial growth in complex conditions (FIG. 5C) with addition of some sensitivity (>7.5 mM) on rich media (FIG. 5D).

Assessment of growth inhibition from polymer degradation release was conducted in well plates with polymer films compared to polymer-free controls with optical density assessment (FIG. 5E). Here, ITA+HD, ITA+OD and ITA+DD demonstrated a profound bacterial growth reduction compared to the polymer-free controls (FIG. 4B). Culture of ITA+OD and ITA+DD in the media conditions with a glucose carbon source did not present any appreciable inhibition (FIG. 4C), and only slight inhibition for ITA+DD on LB broth (FIG. 5F) suggesting the specificity of inhibition to acetate conditions. Remarkably, when compared to commercially available silver nanoparticles, a current gold standard in antimicrobial materials, ITA+DD exhibited similar bacterial growth inhibition (no significance between silver and polymer groups) (FIG. 4D). In contrast, degradable PLLA did not exhibit bacterial growth inhibition, nor did poly (adipate-co-octanediol) (ADI+OD), synthesized using the same approach as with ITA polymers (FIG. 5G), suggesting the itaconate content in ITA+DD polymers was responsible for inhibition (FIG. 4E). These results were reproducible across three independent synthesis batches of ITA+HD (FIG. 4F). With ITA+DD materials, the inhibition was tunable according to polymer reaction times, suggesting the potential for material optimization for the desired application (FIG. 5H).

Translation of in vitro inhibitory characteristics was assessed with an in vivo survival model. Mice injected with ITA+OD or silicone (150 µL, intraperitoneally) three days prior to infection loading (1×10$^9$ CFU *E. coli* per mouse), presented with complete survival (48 hr, n=10) when compared to those injected with a saline sham (FIG. 4G). No evident differences were observed in biomaterial treated groups.

Anti-Inflammatory Characteristics

To understand the anti-inflammatory properties of ITA containing polyesters, we differentiated primary murine bone marrow derived macrophages (BMDM), and assessed the impact of polymer treatment on their inflammatory response (FIG. 6A). Given our interest in the degradation release of ITA into the local environment, we coated materials on glass coverslips (18 mm) and used transwell inserts to facilitate ITA release into the culture media without direct cellular contact (FIG. 7A). Similar to previous studies with ITA, we maintained quantified cell viability (FIG. 7B) and monolayer phenotype (FIG. 7C) with treatment and stimulation. Cells were pretreated for 12 hr with ITA containing materials, solubilized DMI (0.125 uM), PLGA, or media (insert free), then stimulated with LPS (100 ng/mL, noted as +) or LPS (100 ng/mL) and IFNγ (50 ng/mL) (noted as ++) for 12 hr and finally assessed for cytokine expression and phenotypic response.

Cytokine assessment of pro-inflammatory markers with ELISA demonstrates a significant reduction in inflammation response by cells in a soluble environment with ITA containing materials (FIG. 6B-FIG. 6M). Impact on pro-inflammation signaling compared to PLGA and insert free (Blank) controls with similar trend to solubilized DMI (Soluble) was observed following treatment with ITA+DD (FIG. 6B-FIG. 6G, FIG. 7D), ITA+OD (FIG. 6H-FIG. 6M) and ITA+HD (FIG. 7E-FIG. 7I). Notably, there was a significant reduction in IL-1β (FIG. 6B, FIG. 6H; FIG. 7E) IL-12p70 (FIG. 6F, FIG. 6L) and IFNβ (FIG. 6G) without noticeable reduction in TNFα expression (FIG. 6E, FIG. 6K; FIG. 7F), similar to the mechanistic specificity of ITA described elsewhere[17-19]. Observed reduction in IL-6 (FIG. 6C, FIG. 6I; FIG. 7G) was marked for soluble DMI but limited in material pre-treatment, suggesting a dose-dependency to mechanistic regulation as shown elsewhere[17, 18]. Additional assessment of pro-inflammation markers presented reduction in CCL2 (FIG. 6D, FIG. 6J; FIG. 7H) and IL-10 (FIG. 6M; FIG. 7D, FIG. 7I), further suggesting shift to an anti-inflammatory phenotype with ITA treatment. These outcomes align with the mechanistic behavior of soluble ITA that has been published elsewhere.

Anti-inflammatory characteristics were prevalent in the phenotypic response of BMDMs with ITA containing polymer pretreatment. Marked reduction in NOS2 expression was observed with LPS stimulation following pretreatment with ITA+HD, ITA+OD and ITA+DD, as well as LPS+IFNγ stimulation following ITA+DD treatment, with similar expression as soluble DMI (FIG. 8A). Mean fluorescence intensity (MFI) of NOS2 expression for ITA+DD pretreated cells presents a quantified reduction in expression when compared to PLGA treated and insert free controls under LPS (FIG. 8B) and LPS+IFNγ (FIG. 8C) conditions. Observed expression corresponds with reduced nitrite production following treatment with gel (ITA+HD, ITA+OD) (FIG. 8D) and solid (ITA+DD) (FIG. 8E) material. Coupled with cytokine assessment, these outcomes suggest the anti-inflammatory behavior with the degradation release of ITA in vitro.

Reduction of Immune Cell Infiltration in a Peritoneal Injection Model

A murine peritoneal injection model was employed to assess immune cell recruitment upon injection of ITA+OD (viscosity: 42.59±0.43 Pa·s), compared to liquid silicone (viscosity: 13.99±0.15 Pa·s) and saline controls (FIG. 9A). The peritoneal cavity has a limited resident immune cell population, making it a good location to evaluate infiltration through single cell analysis[23]. Silicone was selected to give material comparison of similar properties (i.e: synthetic, inert, injectable). Due to the known complexity of the host response, we used single cell extraction and assessment with multi-color flow cytometry to identify and quantify populations of neutrophils (Ly6G+, Ly6C+), early monocytes (Ly6C+), eosinophils (CD193+), and resident macrophages (CD102+, F4/80+) (FIG. 10).

Materials were delivered in high (150 μL) (FIG. 11) and low (50 μL) (FIG. 9) doses, which were selected according to typical injection volumes into the mouse peritoneum. Representative flow cytometry plots of low dose ten days post-injection present decreased immune cell populations in ITA+OD groups in comparison to silicone controls (FIG. 9B). Material implants were quantified for immune cell populations three (FIG. 9C-FIG. 9F, FIG. 11A-FIG. 11E) and ten (FIG. 9G-FIG. 9J, FIG. 11F-FIG. 11J) days post-implantation. Total viable cell number decreased from three (FIG. 11A) to ten (FIG. 11F) days post implantation. Acute response (day 3, low dose) to ITA+OD and silicone was comparable across cell types and material groups (FIG. 9C-FIG. 9F), with demonstrated significant differences from saline (Sham) control.

Cell populations ten days post injection (low dose) present a significant reduction in recruited neutrophil (FIG. 9G), early monocyte (FIG. 9H), and eosinophil (FIG. 9I) populations in ITA+OD groups compared to silicone controls, which remained unchanged from day three assessment. Although limited, ITA+OD recovers a small resident macrophage population which was not present in the silicone groups (FIG. 9B). The impact on implantation of ITA+OD appears dose dependent, with significantly more acute neutrophil recruitment (FIG. 11B) and a reduced trend of infiltrate response compared to silicone ten days post injection.

Discussion

Typically, synthetic biomaterials have been designed to provide robust mechanical properties while minimizing interaction with the local cell microenvironment[24]. However, there is opportunity in material design to harness biomimetic strategies to develop polymers that interact with the cell microenvironment, fulfilling some of the roles of immune cells. Here, we have demonstrated a platform technology that relies on the degradation capacity of polyester linkages to provide the stable release of ITA using a novel approach of backbone integration.

The bulk mass stability of ITA containing materials over one month here was notable considering the observed ITA-specific efficacy through molecular degradation. Widely studied polyester materials, such as PLLA, PLGA[25, 26], and poly(glycerol sebacate)[27], exhibit similar bulk degradation properties. Optimization of ITA release rate through modification of synthesis techniques could amplify observed cellular activity. In applications, ITA containing materials appear to accomplish a duality in efficacy, supporting device integration with host immunity while simultaneously supporting infection prevention and allowing for interaction with other cell types of the microenvironment. The synthesis method used here is scalable across other material compositions, inviting the opportunity for co-polymerization with other ester-compatible molecules to broaden the range of mechanical properties.

Assessment of inflammatory regulation of stimulated BMDMs treated with the molecular release of ITA containing materials presented a holistic downregulation of key pro-inflammatory markers. Importantly, the trends observed were comparable to the suggested mechanistic activity of ITA published elsewhere[17-19], and followed similar trends to the soluble controls in this study. Comparison of inflammatory regulation ITA polyesters to degradable PLGA, which degrades at similar rates and yields similar acid byproducts, delineated the potential that bioactive efficacy could be derived from material properties (i.e. localized acidity, protein adsorption) that have been reported elsewhere[28].

Previous work has suggested that key cytokine marker downregulation for ITA include IL-6, IL-1β, and IL-12p70, with a maintenance of TNFα[17]. A concentration dependency to efficacy was shown with DMI treatment[17], which may explain why ITA materials differentially regulate some cytokine markers from the soluble controls. Importantly, all materials present evident functional down regulation in nitrile production and NOS expression, hallmarks of inflammatory behavior. Intriguingly, we were able to replicate the feedback loop identified between ITA, IFNβ, and IRG1 with ITA+DD pre-treatment[18].

In the context of biomaterial integration with in vivo host environment, we see an observable downregulation in the key players in inflammatory infiltration in acute biomaterial inflammation[29]. Given that material properties and surface properties have been demonstrated to have an impact on immune response elsewhere[30], we assessed a comparable silicone material on this basis. There is the potential that differences could be further delineated when considering different material characteristics and microenvironments.

When considering the antibacterial efficacy of ITA material, we saw a stark efficacy of infection prevention with E. coli loading in vivo. Surprisingly, there was a similar efficacy observed in the silicone controls. When considered in parallel with the experimental outcomes of the single cell immune cell infiltrate, there may be a level of interplay between the biomaterial host response and infection fighting mechanisms. The increased immune presence observed in the peritoneum three days post implantation, in conjunction with the specific antibacterial efficacy of ITA containing materials may explain the impact on preventing infection, regardless of the inability to prevent E. coli growth on rich media in vitro. This should be considered further in future works with strains of higher clinical risk, wherein the antibacterial characteristics of ITA materials may differentiate them from material controls. In complex in vivo environments, bacterial often grow under substrate limited conditions, further providing basis to ITA effectiveness despite the lack of inhibition on investigated rich substrates.

Further, the role of ITA in pathogenic prevention may not be completely understood, given that multiple strains have identified degradation pathways for the molecule[31]. Importantly, we do not see ITA releasing materials as a replacement to antibiotic therapy, but rather as a method to promote the minimization of infection post implantation. In fact, it has been suggested that the role of ITA in innate immunity may be able to work synergistically with immune cells to restrict persistent growth on substrates such as acetate[15]. Importantly, ICL has been shown to be valuable in persistent virulence, which may indicate a greater value of ITA based materials in biomaterial application[32-35].

Mechanistically, degradation products from ITA based materials lend themselves to a range of proposed immune regulatory mechanisms. As an SDH enzyme inhibitor, one could expect membrane permeability of the small molecule ITA and potential short chain oligomers, as is observed for endogenous itaconate mimics, and through the active transport carrier, dicarboxylate[18]. Work by E I Azzouny et al. suggests the potential for an itaconate extracellular membrane receptor, further lending to the application of itaconate at the material surface[36]. Here, we quantified the release of ITA, but expect that oligomers are also released into the local solution and contribute to polymer efficacy. These may present differential permeability and electrophilic properties, an important aspect in the proposed regulation of the IκBζ-AFT3 axis[19]. Exploration of the role of ITA in activated macrophages, and other immune cells, is still in its infancy[9]. It is possible we are just scratching surface of ITA efficacy, promising potential future opportunity for regulatory ITA based biomaterial therapeutic depots.

Long-term release characteristics of ITA, and the corresponding impact on material properties, should be investigated in future studies. The in vivo results we have demonstrated here ten days post implantation are promising, as we show significant reduction in infiltrated immune cells when compared to a relatively bio-inert control. Coupled with outcomes of E. coli survival model, this presents value in application, preventing infection at the surgical site in the short term with support for material integration that minimizes the typical formation of a fibrotic capsule and frustrated response. Furthermore, the mechanistic value of ITA provides a baseline to assessment in specific therapeutic needs beyond general biomaterial adoption that necessitate anti-inflammatory and infection prevention, such as rheumatoid arthritis which involves excessive innate immunity activation[37]. The oral delivery of ITA to rats presented rapid removal within 24 hours, suggesting the need for a sustained delivery strategy[38]. This opens opportunity for biomaterial-based delivery in future studies.

In summary, a family of biomimetic polyester materials based on itaconate was developed to achieve bioactive constructs with antibacterial, anti-inflammatory and non-toxic behavior. Uniquely, this approach allows for sustained delivery of a multifunctional bioactive molecule for modulation of the local cell microenvironment. As biomaterial applications in medicine continue to grow, the basis of a biomimetic technology will facilitate standard and effective innovation with implantation.

Methods

Materials

Dimethyl itaconate (DMI), 1,6-hexanediol (HD), 1,8-octanediol (OD), 1,10-decanediol (DD), tin (II) ethylhexanoate, 4-methoxyphenol (MEHQ), chloroform-d ($CDCl_3$), poly(L-lactic acid) (PLLA), poly(lactic-co-glycolic acid) (PLGA), diethyl succinate, diethyl adipate, LB (Lennox) broth, silver nanoparticles, Lipase from *Thermomyces lanuginosus*, and lipopolysaccharide (LPS) were purchased from Sigma Aldrich (St. Louis, Mo.). Methanol (MeOH) and sodium hydroxide (NaOH) were purchased from BioShop Canada (Burlington, ON).

Dulbecco's modified Eagle's medium, RPMI 1640 with L-glutamine, fetal bovine serum (FBS), penicillin-streptomycin, N-2-hydroxyethylpiperazine-N-2-ethane sulfonic acid (HEPES), GlutaMax supplement, Dulbecco's phosphate buffered saline (DPBS), (5-(and-6)-Carboxyfluorescein Diacetate, Succinimidyl Ester) (CFDA-SE), propidium iodide (PI), 4',6-diamidino-2-phenylindole (DAPI) Ultra-Comp eBeads, ArC Amine Reactive Compensation Bead Kit, ACK lysis buffer and formaldehyde were purchased from ThermoFisher Scientific (Waltham, Mass.). Mouse recombinant macrophage colony stimulating factor (MCSF) and mouse recombinant interferon gamma (IFNγ) were purchased from Miltenyi Biotec (Bergisch Gladbach, Germany). Greiss reagent kit was purchased from Cell Signalling Technology (Danvers, Mass.). Stains used in flow cytometry were purchased from Biolegend (San Diego, Calif.) unless otherwise noted. All materials were used as received unless otherwise described.

Polymer Synthesis

Polyester materials containing itaconate were prepared using DMI in combination with long chain di-alcohols (i.e. 1,6-hexanediol, 1,8-octanediol, 1,10-decanediol). Monomers were added to a 250 mL triple-neck flask in equimolar amounts with MEHQ (0.5 wt %) as an inhibitor of radical polymerization and tin (II) ethylhexanoate (2 mol %) as a catalyst. The mixture was heated to 130° C. to generate a bulk melt polymerization solution. The reaction solution was stirred at 200 rpm for 6 hours under nitrogen purge followed by a slow reduction of pressure to vacuum and a further 12 hours of reaction, or for times as indicated. Polymers were purified through precipitation in cold methanol (−80° C.) followed by solution decanting and drying of the polymer material. Materials containing other dicarboxylic acids (dimethyl succinate, diethyl adipate) were prepared as described with substitution of DMI with the appropriate carboxylate monomer.

Polymer Characterization

Polymer structure was confirmed using $^1$H NMR on an Agilent DD2 600 MHz spectrometer. Polymer samples were dissolved in $CDCl_3$. Chemical shifts were tested against the resonance of protons in internal tetramethylsilane (TMS). Peak assessment and integration was conducted using MNova software to validate material structure and determine limitation of undesired radical polymerization. Samples were also characterized by ATR-FTIR (Perkin Elmer Spectrum One). Assessment included 32 scans from 4000 to 550 $cm^{-1}$ at a resolution of 4 $cm^{-1}$ and corrections for ATR, baseline and smoothing. Viscosity measurements were performed using a TA Instruments Discovery HR-2 hybrid rheometer. A flow sweep was performed at sheer rates from 0.1 1/1 1/s (7 points, 20° C.)

Bulk Degradation

To assess mass loss, materials (100 mg) were cast on the base of glass vials (20 mL) of known mass and incubated with 2.5 mL of deionized distilled water for indicated time points. At endpoint, supernatant was collected for mass spectroscopy assessment, then dried (48 hr, 75° C.) and weighted for final mass. Accelerated degradation was assessed under basic (1M NaOH) and solution containing lipase (*Thermomyces lanuginosus*, 5000 U $g^{-1}$ polymer) for indicated times using the same method. The degree of degradation was calculated by comparing the dry mass of the polymer film after degradation and the initial mass.

Mass Spectroscopy Assessment

Liquid chromatography-mass spectrometry (LC-MS) analysis was performed using a Dionex Ultimate 3000 UHPLC system and a Q-Exactive mass spectrometer equipped with a HESI source (all from Thermo Scientific) and controlled by Thermo XCalibur 4.1 software. LC separation was conducted on a Hypersil Gold C18 column (50 mm×2.1 mm, 1.9μ particle size, Thermo Scientific) equipped with a guard column. Solvent A was 5 mM ammonium acetate in water (pH 6), and solvent B was 5 mM ammonium acetate in methanol (pH 6). The column was run at a flow rate of 300 A μL/min and at a column temperature of 40° C. Autosampler temperature was maintained at 8° C., and injection volume was 10 μL. The gradient was 0-1 min: 2% B; 1-7 min: linear gradient to 98% B; 7-10 min: 98% B; 10-10.5 min: linear gradient to 2% B; 10.5-15 min: 2% B. Data collection was done in positive and negative ionization modes with a scan range m/z 100-1000, resolution 140 000 at 1 Hz, AGC target of 3e6 and a maximum injection time of 200 ms. Standard solutions of ITA ([M−H]−=129.0193), 1,6-HDO ([M+H]+=119.1067), 1,8-ODO ([M+H]+=147.1380), and DDO ([M+H]+=175.1693) were used for validation of retention time and m/z. Molecular release was interpreted as area under respective m/z peaks.

In Vitro *E. coli* Bacterial Growth Assessment

*Escherichia coli* (BL21) was expanded overnight in LB broth, then seeded (1:100) in fresh medium according to growth conditions. Experiments were carried out in modified M9 minimal medium supplemented with appropriate carbon source (Acetate: 1%, Glucose 0.4%) or LB broth (Lennox). Time course assessment of soluble small molecule inhibition was conducted in 96-well culture plates fitted with a breathable film to encourage aeration and cultured for indicated time with incremental optical density measurement (600 nm). Growth media containing solubilized acid was neutralized with sodium hydroxide (pH=7.0).

To determine polymer antimicrobial properties in solution, six well plates were cast with equal mass polymer samples and polymer free culture plate (polystyrene) controls. Plates were sealed with a plastic film to prevent media evaporation (3 mL/well) and cultured for four days (37° C., 100 rpm) in media conditions as described with daily growth assessment by extraction of (100 μL) to measure change in optical density (600 nm). Silver nanoparticles (10 nm) and PLLA (Mn=85-110 kDa, Sigma) were used as positive and negative controls respectively. Soluble assessment of DMI was conducted using the method described for polymer samples using a 12 well plate format (1.5 mL/well).

Bone Marrow-Derived Macrophage Culture

Macrophage cells were isolated from 6-12 week old C57BL/6 mice as described previously[39] and cultured in RPMI-1640 medium with L-glutamine supplemented with 10% heat inactivated fetal bovine serum, penicillin-streptomycin (100 U $mL^{-1}$) and MCSF (20 ng $mL^{-1}$) for seven days. For experiments, cells were seeded at 90 000 cells $cm^{-2}$ in 6 well culture plates. Cells were treated with ITA+DD, ITA+OD, ITA+HD, or PLGA (coated on glass coverslips; diameter=18 mm) in transwell inserts (8-μm pore size), soluble DMI (0.125 μM), or media only for 12 hr, then activated with LPS (*E. coli* O111:B4; 100 ng/mL), or LPS (100 ng $mL^{-1}$) and IFNγ (50 ng $mL^{-1}$) for 12 hr prior to assessment. Unstimulated cells treated with identical groups were used as a negative control.

Quantification of Cytokines and Nitric Oxide

Cytokine quantification was conducted on cell supernatants using a mouse 10-plex pro-inflammatory assay or an interferon beta single plex assay (Eve Technologies, Calgary, AB) and calculated using their standard curve. Nitrite content was determined using a Greiss Reagent Kit.

Animal Study Ethics

Experiments in this disclosure involving animals were conducted under the *Guide to the Care and Use of Experimental Animals* from the Canadian Council on Animal Care and Procedures approved by the Animal Care Committees of the University of Toronto and University Health Network (Toronto, Canada).

Peritoneal Material Implantation Study

An immune cell infiltration model in the peritoneal cavity was used to assess host response to implanted materials. Injected materials were prepared by sterilizing in 70% ethanol and washed in DPBS followed by drying under sterile vacuum conditions (3 days). Adult C57BL/6 mice (6-8 weeks old, Charles River Laboratories, USA) were injected (low dose: 50 μL, high dose: 150 μL) with ITA+OD, silicone, or saline (Sham) using a 18 G needle into the peritoneal cavity. Three or ten days post implantation, animals were euthanized and the peritoneal cavity was washed with DPBS (10 mL) to extract single cell infiltrates. Cells were concentrated, treated with ACK lysis buffer to remove red blood cells (1 mL, 5 min), washed with DPBS, then counted and assessed by flow cytometry.

Bacterial Survival Model

ITA+OD and silicone material was prepared as described for the peritoneal infiltration model, then adult C57BL/6 mice (6-8 weeks old, Charles River Laboratories, USA) were injected intraperitoneally (18 G needle) with ITA+OD, silicone, or saline (Sham). Three days post implantation, animals were administered an *E. coli* (BL21 strain) bacterial load (200 µL, 1×10$^9$ CFU per mouse) or saline (200 µL). Animals were monitored every two hours for 12 hours, then at 16, 24, and 48 hours for clinical signs of welfare. Clinical signs included respiration, physical appearance, behavior and body appearance, and a score greater then 21 (or greater then 3 in a respiratory category) indicated the humane endpoint as described elsewhere[40].

Flow Cytometry

Cells analyzed by flow cytometry were concentrated (2 million/100 uL), washed with DPBS and stained with Zombie Violet Fixable Viability Kit (1:500; RT, 20 min), blocked with anti-CD16/32 (RT, 10 min), and surface stained according to experimental protocol (4° C., 30 min). In vitro studies with BMDMs were stained with anti-F4/80 and CD11b, fixed in 4% formaldehyde, permeated (Permeabilization Buffer, eBioscience), and stained for anti-NOS2 (Santa Cruz Biotechnology). Cells were gated for viability and F480$^+$/CD11b$^+$ cells prior to assessment of mean fluorescence intensity (MFI) for NOS2 expression. Peritoneal single cell extracts were surface stained with a multi-colour immune cell panel (Gating: FIG. 10).

Compensation and positive staining were performed for each experimental run with UltraComp eBeads and ArC Amine Reactive Compensation Bead Kit. Flow cytometric assessment was conducted on a BD LSRII-OICR Cytometer (Flow and Mass Cytometry Facility, University Health Network, Toronto, ON). Data acquisition was done with BD FACS Diva software, analyzed with FlowJo (TreeStar) software. Immune cell number in peritoneal extracts was determine as relative abundance against a manual cell count conducted prior to staining.

Screening Fibroblast Cell Attachment and Viability to Polymer Sheet

To assess cell attachment and viability, ITA+OD was cast in 24-well plates (0.2 mL) to form a thin polymer sheet. Prior to cell seeding, wells were thoroughly rinsed with PBS and sterilized with 70% ethanol (30 min) followed by three washes in PBS. Dermal fibroblasts were seeded in coated wells or uncoated controls (tissue culture polystyrene) at 1.8×10$^4$ cells/cm$^2$, cultured in DMEM supplemented with 10% fetal bovine serum, Glutamax (1%) and Pen/Strep (100 U mL$^{-1}$). Two days post-seeding, cell viability was assessed using CFDA-SE (1:1000) and PI (1:200) in DPBS (30 min, 37° C.) followed by fixation in 4% paraformaldehyde (30 min). Cells were counter-stained with DAPI (1:1000) and imaged with an Olympus fluorescent microscope. Adhered viable cells were counted using the IMARIS 8 image analysis and compared between experimental groups.

Material Coating

To demonstrate material application, ITA+OD was combined with Sudan IV in ethyl acetate (0.8 mg/mL) and coated on the inner wall of silicone tubing with slow rotation during solvent evaporation. Coating of ITA+DD on metal alloy was done by dropwise solvent casting (0.8 mg/mL) dissolved in ethyl acetate.

Statistical Analysis

All data are presented as the average±standard deviation (s.d.) and differences with p<0.05 were considered significant. Sample sizes (n) indicate biological replicates or number of animals. Statistical analysis were conducted using Graphpad Prism 8. Normality and equality of variance were tested before a statistical test. One way ANOVA in conjunction with Tukey's Multiple comparisons test was used to determine the statistical significance in pairwise comparisons.

Two-Step, One-Pot Polycondensation Reaction Generating Tunable Elastic Materials Synthetic polyester elastomeric constructs have become increasingly important for a range of healthcare applications, due to tunable soft elastic properties that mimic those of human tissues. A number of these constructs require intricate mechanic design to achieve a tunable material with controllable curing. The present disclosure also relates to the synthesis and characterization of poly(itaconate-co-citrate-co-octanediol) (PICO), which exhibits tunable formation of elastomeric networks through radical crosslinking of itaconate in the polymer backbone of viscous polyester gels. Through variation of reaction times and monomer molar composition, we were able to generate materials with modulation of a wide range of elasticity (36-1476 kPa), indicating the tunability of materials to specific elastomeric constructs. This correlated with measured rapid and controllable gelation times. As a proof-of-principle, we developed scaffold support for cardiac tissue patches, which presented visible tissue organization and viability with appropriate elastomeric support from PICO materials. These formulations present potential application in a range of healthcare applications with requirement for elastomeric support with controllable, rapid gelation under mild conditions.

Popularity in application of synthetic polymer elastomers has stemmed from the ability to provide structural and mechanical stability while also mimicking the local dynamics of host tissue microenvironments[41]. Applications can range across biomedical technologies, serving both as mechanical supports for tissue regeneration with and without tissue engineered technologies, and as structures for in vitro organ-on-a-chip devices to better mimic the extracellular matrix (ECM) characteristics of native tissues. Examples of synthetic elastomers used in biomedical research include a diverse range of backbone structures such as polyurethanes[42], and polyesters[43], among others[44].

Use of polyester linkages has attracted attention based on the wide range application of polylactones, including poly (L-lactide) and poly(glycolide), in FDA approved applications[45]. Although these exhibit desirable compatibility, they are limited by their mechanical stiffness[46]. As such, effort has been made to develop soft biomaterial polyester elastomers including aliphatic based (e.g poly (lactide-co-caprolactone)[47], poly(glycolide-co-caprolactone)[48, 49], polyhydroalkanone based (e.g. poly(hydroxybutyrate)[50]), and polyol based (e.g. poly (glycerol-co-sebacate) (PGS)[51], poly (octanediol-co-citrate) (POC)[52]) material constructs.

While these polyester elastomers provide desired mechanical stiffness for soft material application, they are limited by thermoplastic properties that require prolonged heating and/or reduced pressure to generate a branched elastomeric structure. This motivates the inclusion of secondary crosslinking mechanisms in polyester structures to overcome the need for thermal processing. To achieve this goal, photopolymerization is an effective strategy. This has been accomplished previously[53], including post-polymerization acrylation of PGS[54, 55], citrate based materials[56], terminally acrylated star-polyesters[57, 58] and inclusion of unsaturated carbon bonds in the material backbone[59-63]. In our previous works, we have utilized tri-carboxylic acid and di-alcohol based polyesters which include maleic anhydride in their material backbones with great success in in vitro[64-66] and in vivo applications[67, 68].

Although successful, materials containing maleic anhydride as an unsaturated group require a relatively high crosslink energy to achieve gelation, motivating alteration of the material backbone to include an unsaturated moiety with greater reactivity to radical polymerization. Itaconic acid (ITA) is an unsaturated di-carboxylic acid used widely as a crosslinking agent given the high reactivity of its pendant alkene group[69]. Recently, Winkler et al. generated materials possessing unsaturated acrylate bonds available for further functionalization[21]. This provided us with a framework to incorporate this molecule into polyester resins to achieve a two-step elastomer polymerization process with precise control of crosslinking characteristics.

In this disclosure, there is disclosed the synthesis of a polyester elastomer combining citric acid, 1,8-octanediol, and ITA, designated poly(itaconate-co-citrate-co-octanediol), or PICO, to yield a novel polymer gel with the ability for secondary carbon-carbon polymerization through a radical mechanism. Given it is a viscous gel following initial polycondensation, this material can be formed into intricate shapes then cured rapidly to generate a functional elastomeric structure. Herein, the inventors have characterized this material under a number of reaction conditions to demonstrate its tunability of mechanical properties to application. As a functional example of biomaterial application, we demonstrate the successful formation of PICO scaffolded cardiac tissue engineered patches, which require mechanical support for repetitive beating cycles. Developed through a straightforward synthesis procedure, this family of ITA based polyester elastomers presents a wide range of material tunability, both in the context of gelation time and elasticity, yielding controllable gelation under mild curing conditions.

Results

Material Development

Using a two-step, one-pot polycondensation reaction, carboxylate and alcohol monomers were combined to generate molecular branched viscous polyester PICO gels with release of MeOH and ethanol (EtOH) by-products removed through boiling and nitrogen gas purge (FIG. 12). A two-step process was used to facilitate chain branching with tri-carboxylate TEC and OD, priming chains for reactivity with ITA molecules (DMI). This method maintained the unsaturated groups through condensation (avg: 103±1%), as verified by proton NMR ($^1$HNMR) (Table 1). A representative $^1$HNMR (FIG. 13A) and FTIR (FIG. 14D) present the integration of relevant monomer functional groups into the final purified polymer materials. A time course of OD esterification in the reaction of TEC with OD (1:1 molar ratio), quantified using $^1$HNMR, presents a plateau of reactivity at 2 hours, rationalizing the selection of this timing for pre-polymerization prior to DMI addition to polymer combinations (FIG. 13B). Given this finding, we generated a library of materials with variation in monomer feed ratio and reaction time post DMI addition (Table 2). Throughout, the molar feed ratio of OD to carboxylate content (moles of DMI+TEC) was held equal, with variation of citrate to ITA. Materials were generated with an acid feed ratio (DMI:TEC, mol:mol) of 1:1 (Polymer 1-3), 1:2 (Polymer 4-7) and 3:4 (Polymer 8-11). Reaction time post DMI addition was varied from 2 to 3.5 hours.

$^1$HNMR assessment and quantification was conducted for each material combination (Table 3). We analyzed the polymer content, amount of each carboxylate group (citrate and itaconate) in the polymer relative to OD; monomer incorporation yield, ratio of carboxylate polymer content (citrate or itaconate) to the monomer molar feed ratio (TEC or DMI) on the basis of OD; and the degree of polymer groups that were esterified, the disappearance of peaks corresponding to monomeric endgroups. Esterification of monomers was confirmed by the formation of esterified OD (B, 4.28-4.00 ppm) and disappearance of DMI monomeric end groups (C, 3.78-3.75; D, 3.70-3.67 ppm), TEC (I, 1.40-1.20 ppm), and OD (E, 3.66-3.59 ppm). Esterification of OD (66.8-76.9%, avg: 73±3%) remained relatively consistent across polymer groups, with no evident trend related to polymerization conditions. Increase in length of reaction time presented a trend in increased TEC (39.3-55.1% avg: 46±5%) esterification, but this was not consistent across polymerization groups.

With focus on this study on the incorporation of pendant unsaturated group on ITA for radical based post-polymerization, we highlight the incorporation and esterification of these groups. Degree of esterification was unrelated to reaction time in Polymers 1-3 (42.2-47.0%) and increased with reaction time with Pol 4-7 (31.8-46.1%) and Pol 8-11 (38.9-43.9%) (FIG. 13C). Esterification of ITA (disappearance of DMI end groups) was preferential to the end groups further from the pendant unsaturated group across all material groups (C: 29±5%, D: 50±7%) (Table 1).

Overall, ITA groups exhibited a low degree of esterification, suggesting they were mainly maintained as end groups on polymer chains. Yield of ITA incorporation increased with reaction time in the high DMI feed group (Pol 1-3) from Polymer 1 (59.9%) to Polymer 3 (101.0%) (FIG. 13D). This trend was inversed in groups with low (Pol 4-7, 100.1-76.9%), and medium (Pol 8-11, 85.9-67.6.9%) DMI feeds. The incorporation of TEC was greater than 100% across groups with no evident trend (102.7-142.5%, avg: 121±10%). This result is attributed to the 2 h pre-polymerization period and the excess of stoichiometric equivalence in reactive groups (3 acid groups—TEC, 2 alcohol reactive groups—OD) with the overall molar equality of acid to alcohol groups. Assessment of molecular weight by gel permeation chromatography presented low molecular weight materials (Mn <6000 Da) with a high dispersity (1.81-7.81) (Table 4). There was no strong correlation between polymerization conditions, but these outcomes further indicate the low degree of polymerization conversion of these materials.

Crosslinking Characteristics

The gelation time of bioelastomer prepolymers was measured using a rotational rheometer outfitted with a UV light apparatus to measure change in storage (G') and loss (G") modulus with illumination. Time traces of all samples present stability; G' and G" values were stable from the start of data collection measurement and remained constant (t≤100 s) before the crosslinking was induced by UV light (FIG. 15A-FIG. 15C).

Polymer gelation point was considered the point where G' exceeded G" as an indication of gel to solid material transition (FIG. 15D). Variation in crosslinking time was seen across groups, with the most rapid and consistent reactivity observed with high ITA content (Polymer 1-3) (FIG. 15A) (Polymer 1: 33.5 s, Polymer 2: 88.2 s, Polymer 3: 27.4 s). Materials with low DMI feed ratio demonstrated variation in reactivity, with no evident crosslinking in low reaction time materials (Polymer 4 and 5) and lack of consistent trend in Polymers 6 and 7 (Polymers 4, 5: —no gelation, 6: 21.5 s, 7: 94.2 s) (FIG. 15B). Moderate ITA content materials present a trend of decreasing crosslink time with increased reaction time (Polymer 8: no gelation, Polymer 9: 173.2 s, Polymer 10: 102.2 s, Polymer 11: 45.6 s) (FIG. 15C). Polymers that did not have evident gelation were assessed for 600 s of UV exposure.

Mechanical Properties

Figure 16B:
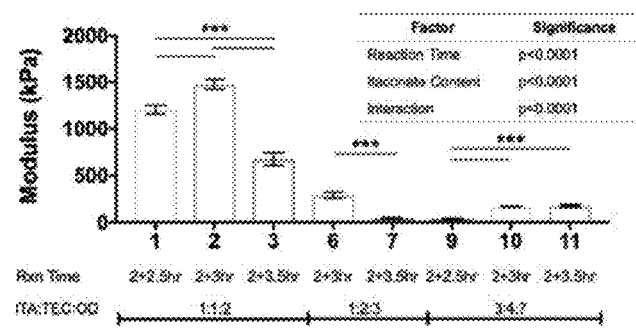

Tensile properties of all polymer groups were assessed using ASTM standard methods. Representative stress-strain curves (FIG. 16A) present modulation of elasticity with change in monomer feed ratios. Crosslinked with a consistent energy (800 mJ), the high DMI feed group (Polymer 1-3) presented a notably higher Young's modulus then the polymers with the low and moderate ITA feed. Young's modulus decreased with reaction time in the high DMI feed group (Polymer 1-3) from Polymer 1 (1204±46 kPa) to Polymer 3 (678±67 kPa) (Polymer 2: 1476±52 kPa) (FIG. 16B).

Figure 16C:
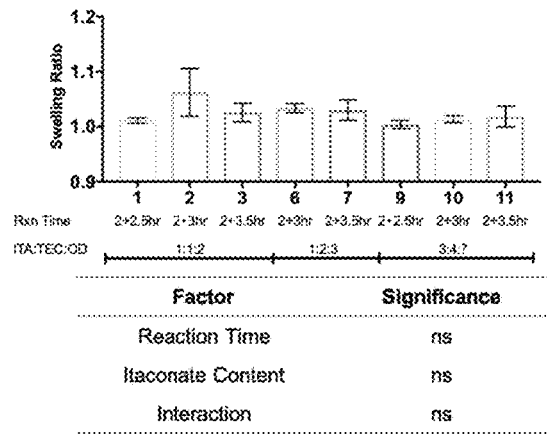

The trend was also observed in the low DMI feed group (Polymer 6: 290±31 kPa, Polymer 7: 41±6 kPa) but reversed in the medium DMI feed group (Polymer 9: 36±9 kPa, Polymer 10: 174±4 kPa Polymer 11: 177±11 kPa). A strong significance ($p<0.0001$) was calculated for the impact of reaction time and DMI feed content, as well as their interaction effect on elastic modulus. Cyclic loading of polymers 2, 6, and 10 confirmed elastomeric mechanical stability of PICO over time (1500 cycles, 10% strain) (FIG. 17). No significant swelling in water was observed in tested material groups (ratio ~1.0) (FIG. 16C).

Figure 16D:
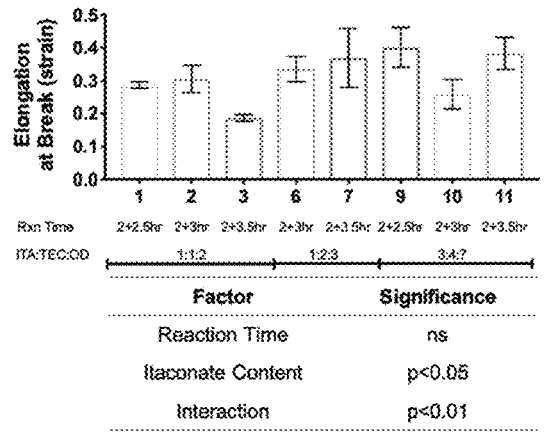
Figure 16E:
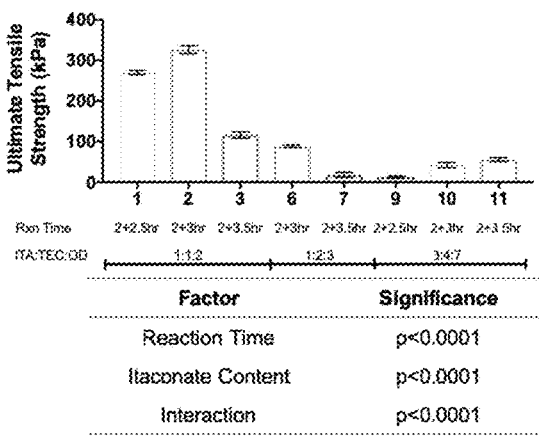

Longer immersion of a representative polymer (Polymer 10) over three days did not change the results of the swelling test indicating that overnight incubation was sufficient to approximate the swelling equilibrium (FIG. 18A). Material elongation at break was not largely impacted with reaction time (non-significant) but showed a slightly significant change with ITA content ($p<0.05$) and the interaction of this with reaction time ($p<0.01$), although the magnitude of elongation range between all materials was small (0.19-0.4) (FIG. 16D). Considering the relatively consistent elongation at break, ultimate tensile strength follows a trend directly related to that of modulus and impacted by reaction time and ITA feed ($p<0.0001$) (FIG. 16E). Elasticity of the polymer was demonstrated to be tunable with changes in crosslink energy, Young's modulus of Polymer 9 increased with crosslink energy from 36 kPa at 800 mJ UV exposure to 298 kPa at 1000 mJ and 717 kPa at 1500 mJ UV exposure (FIG. 18B).

Hydrolytic degradation behaviour of crosslinked PICO materials was assessed under basic conditions (0.25 M, 48 h, 37° C.) to differentiate impact of polymer composition on rate of dissolution. The high DMI feed group materials degraded at a lower rate over 48 h (Polymer 1: 31±3%, Polymer 2: 26±1%, Polymer 3: 44±5%) (FIG. 19A), when compared to low (Polymer 6: 66±8%, Polymer 7: 67±4%) (FIG. 19B) and moderate (Polymer 9: 83±8% Polymer 10: 71±4% Polymer 11: 82±6%) (FIG. 19C) feed groups. This trend was observed at 12- and 24-hour sample points as well, with an evident plateau in mass loss in high ITA content materials. Comparison of mass at 48 h of exposure highlights the significance of itaconate content ($p<0.0001$) and reaction time ($p<0.0001$), as well as their interaction effect ($p<0.05$) on hydrolytic degradability (FIG. 19D).

Cardiac Patch Generation and Cell Toxicity Assessment

Patches were generated using standard photolithography and microfabrication techniques. PDMS moulds of the desired scaffold shapes were fabricated, into which the polymer was perfused (FIG. 20A). Exposure to UV light was performed and the scaffold shape was retained following removal from the mould. Generation of polymeric scaffolds with roughly 150 µm wide struts containing narrow grooves was successful with this polymer, indicating its applicability in settings where control over features at the micron-scale is required such as in tissue engineering applications. Due to other relevant characteristics of this polymer for cardiac tissue applications, such as its elastomeric properties, evaluation of its use as a scaffold for CMs was undertaken.

CM-based patches were successfully generated and the crosslinked PICO polymer 10 provided a suitable scaffold for cell attachment and assembly (FIG. 20B). Neonatal rat CMs were able to wrap around the scaffold struts and compacted the hydrogel to form tissue patches (FIG. 20C). CMs on the patches demonstrated spontaneous contraction within two days of cultivation and maintained contraction over four days at which point cell culture was stopped. The polymer scaffold was compressed by the contracting tissue, demonstrating the suitability of this material for a cardiac patch application. Cell viability was observed though CFDA-SE and PI staining which reveals live and dead cells respectively (FIG. 20D to FIG. 20G). A very high proportion of live cells can be observed, indicating the compatibility of the polymer for use in this fashion (FIG. 21A to FIG. 21D). Regions of high cell density (FIG. 20F, FIG. 20G) and lower cell density (FIG. 20D, FIG. 20E) around the scaffold material can be observed.

Assessment of cell compatibility to polymer leachates and degradation products was conducted using a conditioned media method. Polymers 3, 6, and 10 were soaked in complete culture media (15 mg/mL, 24 h, 37° C.), that was then diluted (1×, 2×, 5×, 10×) and applied to the cardiac fibroblast monolayers (FIG. 20H). Quantification of cell death by lactate dehydrogenase (LDH) release presented no significant difference in all polymer groups for all dilutions when compared to non-conditioned control. In all groups the dilutions and control presented a significantly lower dead cell count then the positive control (10% Triton-X, 1 h).

Discussion

Through a one-pot polycondensation reaction, we have synthetized a polyester based elastomer, PICO, with a secondary radical polymerization functionality as a result of unsaturated pendant groups in the material backbone. Crosslinked polyester elastomers, including ring-opening[47-49, 57, 58, 70] and polycondensation[54, 71, 72] derived polymer derivatives, have demonstrated extensive efficacy in numerous biomedical applications[43, 53, 73]. Here, we have leveraged condensation techniques for the addition of ITA to a POC backbone to simplify the implementation of synthesized polyester gels as crosslinked bio-elastomers.

To understand the range of properties achievable with this chemistry, we selected diverse DMI feed ratios that would theoretically result in a high (1:1, DMI:TEC; Polymers 1-3) and low (1:2, DMI:TEC; Polymers 4-7) unsaturated content similar to the range observed elsewhere[54]. Given this work highlights PICO for the first time, we first developed material feeds with this wide range of DMI monomer feed ratios. With limitations observed in crosslinking characteristics in the low ITA group (Polymers 4-7), we then assessed the moderate DMI feed (3:4 DMI:TEC; Polymers 8-11) as a midpoint between the high and low groups to better understand the potential optimal material properties.

A two-step process facilitated chain branching with tri-carboxylate TEC and OD, priming chains for reactivity with ITA molecules (DMI). Use of methylated and ethylated carboxylic acids provided: a) liquid form monomers; b) ease of leaving group removal (boiling points: MeOH=64.7° C. EtOH=78.4° C.)[74], pushing the equilibrium condensation reaction forward; and c) lower required reaction temperature (T=120° C.). The use of carboxylic acid equivalents would have required higher reaction temperatures to achieve melt polymerization (melting points: ITA=162-164° C. citrate=153° C.)[74], and caused undesired side reactivity of the unsaturated pendant group imparted by ITA (data not shown), consistent with other studies[75]. With the technique described here, and the inclusion of an MEHQ radical inhibitor, we were able to maintain the unsaturated functionality across all groups.

Without being bound by any theory, the inventors contemplate that the achievement of elasticity is enhanced by the two-step condensation reaction we used here, allowing for generation of chain branching with combination of a di-alcohol with a tricarboxylic structure, a hallmark in elastomeric materials[60], in advance of forming longer polymer chains. With combination of DMI and TEC with OD at the start of the reaction, we suspect the less desirable ethanol leaving group (compared to methanol) and steric hindrance of TEC would limit its reactivity compared to DMI, preventing the development of an elastomeric polymer bulk. By pre-priming TEC with OD, we achieved greater spacing between stiff radical crosslinking bonds (generated by ITA polymer content), achieving increased chain mobility in final elastomeric structures.

In assessing the optimal properties and tunability of PICO synthesis, the inventors considered both the stoichiometric feed ratios of monomers and the reaction time following the addition of DMI to the reaction mixture. As expected, the inclusion of higher amounts of ITA (Polymers 1-3) lead to a decrease in gelation time, but overall the materials that demonstrated gelation did so in less than 100 s (excluding Polymer 9) under a low powered UV lamp. It was the inventors hypothesis that ITA incorporation into the polymer backbone, would increase with reaction time, in turn decreasing gelation time and they observed an increase in DMI monomer incorporation into the polymer bulk with reaction time in the high ITA content materials, but this trend was reversed with other groups. Rather, a trend of increasing degree of ITA esterification with reaction time was seen in the low (except for Polymer 6) and moderate ITA groups (FIG. 13C). This suggests that stability of ITA in the material backbone is important for crosslinking reactivity and explains the outcomes of this study; materials that exhibited the most rapid gelation (Polymers 3, 6, 11) presented high esterification percentages.

It is possible that this trend is more important with lower ITA content in the polymer material (Polymer 4-11), but with excess itaconate (Polymer 1-3) esterification is a less significant driving force to mechanical crosslinking stability in the context of elasticity. Overall, the esterification degree was low (<50%), suggesting active groups were largely prevalent on the end of polymer chains due to the pre-esterification of OD with TEC. Further, esterification was preferential to the end group further from the unsaturated group, consistent with selectivity observed elsewhere[76]. Given the high yield values observed in the monomeric incorporation of acid groups in comparison of OD content, coupled with the low degree of esterification, the materials generated here likely present a low degree of polymerization wherein the majority of endgroups are carboxylic acids.

This outcome is attributed to the excess in carboxylate reactive groups in stoichiometric comparison to alcohol groups used here, as has been done in the generation of condensation-based elastomers previously[51, 77]. Future optimization may suggest consideration of stoichiometric equivalence in reactive groups rather than acid:alcohol content.

Assessment of Young's modulus of crosslinked PICO elastomers highlights the wide-range tunability of this bioelastomer. Materials crosslinked at a consistent energy level present the strong correlation between ITA content and stiffness; high ITA PICO presented a much higher stiffness then those with lower ITA content. This correlates with the characteristics of gelation time, as these materials reached a gelation point faster than lower ITA content materials. With prolonged exposure times, the modulus of materials continues to increase (Polymer 9), inviting the concept of elastomer materials tunable to precise crosslinking characteristics according to application. Besides its advantage for fabrication processes, the polymer's property of rapid crosslinking upon UV exposure becomes even more useful when considering applications such as surgical adhesives or sealants with elastomeric properties, which can achieve function by rapid gelation initiated by UV light in vivo[78].

Applications of PICO constructs as tissue specific ECM and scaffolding that match native modulus could include cartilage[79] (~520 kPa), peripheral nerve[80] (~580 kPa), carotid artery[81] (701-965 kPa) and cardiac[82] (~372 kPa), among others. As a crosslinked polymer bulk, materials did not exhibit appreciable swelling, which may provide advantage in applications that necessitate structural integrity. Ester linkages in PICO provide advantageous hydrolytic degradability over time, suggesting the potential for material resorption in application. In considering tissue specific application, the demonstrated tunability of degradation rate adds an additional benefit to optimized properties.

As a proof of concept assessment of PICO in generating bio-relevant elastomeric constructs, we generated cardiac patch materials using methods we have described previously[68]. Cardiac tissue ECM undergoes cyclic loading in vivo, with a modulus that ranges from ~10 kPa in diastole to ~500 kPa in systole[83]. In previous work from our group, we demonstrated materials with modulus ~100 kPa to be advantageous for formation of mature cardiac tissue engineered constructs[60], and therefore selected Polymer 10 to form micro-scale patches. When seeded with neonatal cardiac tissue, we observed robust spontaneous tissue contraction and visible tissue viability (FIG. 20D). The tissue was able to remodel around the structure (FIG. 20B-C), a key feature of healthy cardiac constructs[84-86], and wrap around scaffold struts, suggesting material compatibility (FIG. 20E). The non-toxic behaviour was further supported with cardiac fibroblast culture in PICO conditioned media. Cardiac tissue constructs serve as a strong benchmark to relevance of a bioelastomer, as tissues subject the material to repetitive cyclic loading. The maintenance of material properties and appropriateness in cell interaction suggest PICO materials would be beneficial for applications in tissue and organ-on-a-chip engineering.

The described PICO materials should be useful in bio-applications that require highly tunable elasticity for soft material applications. Diverse needs for soft materials motivate the desire for precision and modulation of elastomeric properties, notably in the context of high precision physical and mechanical properties. Given the short gelation times, application in 3D printing of constructs could be relevant, allowing for generation of high throughput organ-on-a-chip devices or highly detailed implantable medical devices. Future work should focus on further optimization of the synthesis strategy, including the length of pre-polymerization without ITA monomer and the application of vacuum pressure to push the overall esterification forward. Further, inclusion of other carboxylic and diol molecules might broaden the range of material properties for application. The prevalence of pendant functionality of both free hydroxyl (citric acid) and unsaturated alkene bonds also opens possibility to functionalization of materials with other active groups, further emphasizing the potential of these polymer constructs[21, 87, 88]. Here, we focus on the understanding of material synthesis and properties of this family of polymers, but future consideration should investigate the in vivo behaviour to fully assess applicability. PICO material functionality provides interesting opportunities in application of synthetic bioelastomers.

EXPERIMENTAL SECTION

Materials

Dimethyl itaconate (DMI), 1,8-octanediol (OD), triethyl citrate (TEC), stannous octanoate, 4-methoxyphenol (MEHQ), chloroform-d (CDCl$_3$), 2-hydroxy-1-[4(hydroxy-ethoxy)-phenyl]-2-methyl-1 propanone (Irgacure 2959), medium M199x, PluronicF-127, and sodium bicarbonate were purchased from Sigma Aldrich (St. Louis, Mo.). Methanol (MeOH) and sodium hydroxide (NaOH) were purchased from BioShop Canada (Burlington, ON). Polydimethylsiloxane (PDMS, Sylgard 184) was purchased from Dow Chemical (Midland, Mich.). Dulbecco's modified Eagle's medium, Hank's buffered saline solution (HBSS), fetal bovine serum (FBS), penicillin-streptomycin, N-2-hydroxyethylpiperazine-N-2-ethane sulfonic acid (HEPES), GlutaMax supplement, Dulbecco's phosphate buffered saline (DPBS), (5-(and-6)-Carboxyfluorescein Diacetate, Succinimidyl Ester) (CFDA-SE), propidium iodide (PI), and formaldehyde were purchased from ThermoFisher Scientific (Waltham, Mass.). Neonatal Heart Dissociation Kit was purchased from Miltenyi Biotec (Bergisch Gladbach, Germany). Rat tail collagen type I (8.34 mg mL$^{-1}$) and GFR-Matrigel were purchased from Corning (Corning, N.Y.). All materials were used as received unless otherwise described.

Polymer Synthesis

Polymer groups were synthesized using a one-pot condensation reaction to generate a viscous gel material. A mixture of OD (10 g), TEC (as defined in Table 1), stannous octanoate (1% mol/mol ester bond), and MEHQ (0.5% wt to all reactants) were combined in a two necked round bottom flask (125 mL) fitted with a water condenser and collection flask. An overall molar ratio of acid (TEC+DMI) to alcohol (OD) of 1:1 was maintained in all reactions. This mixture was reacted at 120° C. for 2 hr with stirring (200 rpm) and nitrogen flow, followed by the addition of DMI (as defined in Table 1) with an additional reaction of 2 to 3.5 hr. The crude polymer was precipitated in ice cold methanol, decanted and dried for 48 hr before use. As needed, materials were prepared for radical crosslinking initiated by ultraviolet (UV) light by mixing with Irgacure 2959 (1% wt) at 60° C. and crosslinked with exposure to a specific amount of UV energy using a UVP Crosslinker CL-1000 L (Analytik Jena).

NMR Assessment

Purified polymer gels were dissolved in CDCl$_3$ (10 mg/mL) and analyzed by proton nuclear magnetic resonance spectroscopy ($^1$H NMR) with a 500 mHz spectrometer (Agilent, USA) and analyzed using MestReNova software. Specific material molecular properties were determined through peak integration according to the following equations, similar to work published elsewhere[89], with peak assignment according to the representative spectra seen in FIG. 13A. Peak integration range corresponding to each label is summarized in Table 1, and is further confirmed by the $^1$H NMR of each monomer (FIG. 14A-C) First, peak I was delineated into signal corresponding to TEC endgroups ($I_{TEC}$) and backbone OD ($I_{OD}$) as outlined in the supplemental methods. Given this, purified polymer percentage of acid content normalized to diol was determined for ITA (eqn. 1) and citrate (eqn. 2), and corresponding monomer incorporation yield calculations by comparison to monomer feed (eqn. 3). Esterification of monomers was determined through calculation of end groups present for citrate (eqn. 4), ITA (eqn. 5) and OD (eqn. 6) as a measure of degree of polymerization.

$$\text{ITA polymer content} = \frac{4F}{I_{OD}} \times 100\% \tag{1}$$

$$\text{Citrate polymer content} = \frac{2G}{I_{OD}} \times 100\% \tag{2}$$

$$\text{Monomer incorporation Yield} = \frac{\text{polymer content}}{\text{monomer feed}} \times 100\% \tag{3}$$

$$\%\text{Esterified}_{citrate} = \left(1 - \frac{4}{9}\frac{I_{TEC}}{G}\right) \times 100\% \tag{4}$$

$$\%\text{Esterified}_{ITA} = \left(1 - \frac{(C+D)}{3F}\right) \times 100\% \tag{5}$$

$$\%\text{Esterified}_{OD} = \left(1 - \frac{2E}{I_{OD}}\right) \times 100\% \tag{6}$$

Elastomeric Testing

Tensile properties were assessed using dog-bone samples according to ASTM D638-14 standard (width: 5 mm, thickness: 3 mm). Samples were prepared by first generating a PDMS negative from a 3D printed mould and capping it with a glass slide. Moulds were injected with polymer gels containing Irgacure 2959, then crosslinked with 800 mJ cm$^{-2}$ of energy unless otherwise specified. Samples were soaked overnight in DPBS before testing. Tensile testing was conducted to failure under wet conditions using an Electroforce 5200 Biodynamic Test Instrument (BOSE) with strain rate of 0.1 mm s$^{-1}$ and collection of force displacement data was completed using WinTest software. Bulk modulus was determined using data from the first 10% strain. Ultimate tensile strength and elongation at break were collected from the breaking point.

Swelling Measurement

Swelling of crosslinked polymer samples was quantified at 37° C. with samples that had been crosslinked as described for elastomeric property assessment. Dry polymer mass was recorded, then material was submerged in DPBS and incubated overnight (or for time described in multi-day assessment). Final mass was determined by carefully removing excess DPBS by blotting before collecting value. The swelling ratio was calculated by eqn. 7.

$$\text{Swelling ratio} = m_f/m_d \tag{7}$$

where $m_f$ is wet polymer mass and $m_d$ is dry polymer mass.

Polymer Gelation Properties

The gelation time of prepolymer gels was determined using viscoelastic rheology measurement techniques. Polymer gels with Irgacure 2959 were prepared as described and placed on the Peltier plate module (25 mm) of a TA Instruments rotational rheometer (TA Instruments, Discovery HR-2), customized to be fitted with a UV lamp (365 nm, Thorlab) under the plate holder (gap: 1 mm). To analyze gelation, a time sweep was used (Frequency: 1 Hz, Strain:

1%, 25° C.) with collection of storage (G') and loss (G") moduli. Samples were allowed to equilibrate in the instrument for 5 min, then data collection was initiated 100 s prior to UV lamp illumination. The moduli were plotted, and gelation time was reported as the time of curve crossover post-UV lamp exposure.

Polymer Degradation

Degradation of crosslinked polymer samples was quantified at 37° C. under accelerated conditions (0.25M sodium hydroxide) with samples that had been crosslinked as described for elastomeric property assessment. Initial dry polymer mass was recorded, then material was submerged in degradation solution (10 mL) and incubated for 12, 24 or 48 hr (37° C., 100 rpm). At endpoint, materials were removed, washed twice in deionized distilled water, then dried before measuring final mass. Mass loss was calculated by eqn. 8.

$$\text{Mass Loss} = (m_i - m_f)/m_i \tag{8}$$

where $m_f$ is final polymer mass and $m_i$ is initial polymer mass.

Neonatal Rat Heart Cell Isolation

Heart tissue from neonatal rats was isolated as described previously according to an approved protocol through the University of Toronto Animal Care Committee[60, 68]. Sprague-Dawley neonatal (1-2 days old) rats were euthanized and hearts collected in HBSS. Following the removal of the vena cava and aorta, the hearts were quartered and rinsed four times in HBSS. Digestion, including red blood cell lysis, was performed using GentleMACS Dissociator (Miltenyi Biotec) and Neonatal Heart Dissociation Kit according to the manufacturer's protocol. Cells were then incubated for 1 hour and cardiomyocyte (CM)-rich supernatant was collected. The culture of rat CMs was conducted in Dulbecco's modified Eagle's medium containing glucose (4.5 g $L^{-1}$) with 10% (v/v) FBS, 1% (v/v) penicillin-streptomycin (100 mg $mL^{-1}$), 1% (v/v) HEPES (100 U $mL^{-1}$), and 1% GlutaMax supplement.

Cardiac Patch Development

Polymer scaffolds were made according to previous work[90]. Briefly, PDMS moulds of scaffold patches were fabricated from SU-8 master moulds that were generated using standard microfabrication techniques, and subsequently capped onto glass slides. Polymer 10, selected on the basis of matching cardiac ECM elasticity, mixed with Irgacure 2959 as described, was perfused into the moulds and exposed to 800 mJ/cm² UV light. The PDMS cap was removed and scaffolds were soaked in DPBS for 1 hour, sterilized in 70% (v/v) ethanol overnight, and washed and soaked in DPBS for 3 hours. Scaffolds were coated with 0.2 wt % gelatin in PBS at 37° C. for 1 hour to improve cell attachment. A PDMS-based scaffold holder was also fabricated in a six well plate according to previous work[68], soaked with 5 wt % PluronicF-127 in DPBS to prevent cell adhesion and rinsed once with DPBS. Gelatin-coated scaffolds were placed onto the PDMS-based scaffold holders and pinned in place using 0.15 mm diameter minutien pins (Roboz Surgical) prior to cell seeding.

Pelleted CMs were suspended in a collagen-based gel at a density of 100 million cells per mL. The collagen-based gel was made as previously described[66], from rat tail collagen type I with a final collagen concentration of 3 mg/mL in deionized water with 10% (v/v) M199 (10×), 10% (v/v) sodium bicarbonate (2.2 g $L^{-1}$), and 15% (v/v) Matrigel. The gel was neutralized with 1 M NaOH. According to previous work[68], 25 μL cell suspension was pipetted onto the scaffold and incubated at 37° C. for 20 minutes to allow for gelation, after which an additional 25 μL cell suspension was pipetted onto the scaffold and incubated for 40 minutes. Pre-warmed cell culture media was then added to the scaffolds and placed in an incubator. Culture medium was changed every two days.

After four days, cells on the scaffolds were labeled with CFDA-SE (1:1000) and PI (1:75) in DPBS at 37° C. for 30 min. Patches were fixed overnight in 4% formaldehyde at 4° C. Before imaging, cells were stained with DAPI (1:500) in DPBS for 30 minutes at room temperature. Confocal images of the cardiac patch tissues were captured with a Nixon A1R+ laser scanning confocal microscope in the University Heath Network Advanced Optical Microscopy Facility.

Cytotoxicity Assessment

Assessment of the cell toxicity of PICO leachate and their degradation products was conducted using a conditioned media approach. Crosslinked polymer samples were prepared as described for elastomeric property assessment, then soaked in complete rat CM media (15 mg polymer/mL) for 24 hr at 37° C. to generate conditioned media. To assess toxicity, primary rat cardiac fibroblasts were seeded in 24 well plates ($10^4/cm^2$) and allowed to attach overnight. Cells were then treated with dilutions of conditioned media (1×, 2×, 5×, 10×) in complete rat CM media for 24 hr. Cell death was quantified and compared to an untreated and positive (1% Triton-X, 1 hr) control using a lactate dehydrogenase (LDH) Cytotoxicity Assay Kit (Cayman Chemical Company) per manufacturer's instructions. LDH presence in cell supernatants was correlated to cell number using a calibration curve of LDH release to cell death.

Statistical Analysis

Normality and equality of variance were tested using Graphpad Prism 8.0. Two-way ANOVA followed by pairwise comparisons with Tukey's multiple comparisons test method were used to determine the statistical significance and assess the interactive effects of factors in FIGS. 3 and 5. One-way ANOVA followed by Dunnett's multiple comparisons test were used to determine the statistical significance and pairwise comparisons of FIG. 6E.

Tables

TABLE 1

¹H NMR data for itaconate content in PICO materials. Esterification percentage compares the selectivity of acid end groups to esterification. Yield of unsaturated itaconate bond defines maintenance of pendant ITA unsaturated groups in polymerization

| | Monomer | | % Esterified | | | |
| --- | --- | --- | --- | --- | --- | --- |
| | Feed (%) | | Peak | Peak | | Unsaturated |
| Polymer | TEC | DMI | C | D | Overall | Yield (%) |
| 1 | 50.0 | 50.0 | 34.4 | 54.5 | 44.4 | 104.6 |
| 2 | 50.0 | 50.0 | 30.6 | 63.6 | 47.0 | 102.5 |
| 3 | 50.0 | 50.0 | 33.7 | 50.7 | 42.2 | 103.1 |
| 4 | 66.0 | 33.0 | 22.6 | 41.0 | 31.8 | 103.5 |
| 5 | 66.0 | 33.0 | 23.7 | 41.0 | 32.3 | 102.0 |
| 6 | 66.0 | 33.0 | 40.4 | 51.8 | 46.1 | 102.5 |
| 7 | 66.0 | 33.0 | 29.9 | 47.6 | 38.7 | 105.2 |
| 8 | 57.0 | 43.0 | 27.9 | 49.9 | 38.9 | 103.0 |
| 9 | 57.0 | 43.0 | 22.9 | 43.8 | 33.3 | 101.5 |
| 10 | 57.0 | 43.0 | 30.7 | 55.4 | 43.1 | 102.5 |
| 11 | 57.0 | 43.0 | 34.4 | 53.4 | 43.9 | 105.2 |

TABLE 2

Polymer reaction combinations with variation in monomer feed ratio and reaction time

| Polymer Code | Feed Ratio DMI:TEC:OD (mol:mol) | Reaction Time (hr) |
|---|---|---|
| 1 | 1:1:2 | 2 + 2.5 |
| 2 | High ITA | 2 + 3 |
| 3 |  | 2 + 3.5 |
| 4 | 1:2:3 | 2 + 2 |
| 5 | Low ITA | 2 + 2.5 |
| 6 |  | 2 + 3 |
| 7 |  | 2 + 3.5 |
| 8 | 3:4:7 | 2 + 2 |
| 9 | Moderate ITA | 2 + 2.5 |
| 10 |  | 2 + 3 |
| 11 |  | 2 + 3.5 |

TABLE 1

Summarized NMR analysis data indicating polymer composition and esterification

| Polymer | Monomer Feed (%) | | Polymer Content (%) | | % Esterified | | | Monomer Incorporation Yield (%) | |
|---|---|---|---|---|---|---|---|---|---|
|  | TEC | DMI | TEC | DMI | OD | TEC | DMI | TEC | DMI |
| 1 | 50.0 | 50.0 | 71.3 | 30.0 | 74.0 | 44.0 | 44.4 | 142.5 | 59.9 |
| 2 | 50.0 | 50.0 | 51.4 | 43.4 | 69.8 | 54.1 | 47.0 | 102.7 | 86.9 |
| 3 | 50.0 | 50.0 | 57.7 | 50.5 | 76.3 | 55.1 | 42.2 | 115.5 | 101.0 |
| 4 | 66.0 | 33.0 | 82.7 | 33.0 | 71.2 | 39.3 | 31.8 | 125.4 | 100.1 |
| 5 | 66.0 | 33.0 | 82.7 | 33.9 | 72.2 | 40.3 | 32.3 | 125.3 | 102.6 |
| 6 | 66.0 | 33.0 | 69.1 | 26.8 | 75.5 | 48.2 | 46.1 | 104.7 | 81.3 |
| 7 | 66.0 | 33.0 | 83.1 | 25.4 | 76.9 | 42.4 | 38.7 | 125.9 | 76.9 |
| 8 | 57.0 | 43.0 | 71.3 | 36.9 | 71.5 | 42.9 | 38.9 | 125.1 | 85.9 |
| 9 | 57.0 | 43.0 | 66.9 | 42.8 | 66.8 | 44.0 | 33.3 | 117.4 | 99.6 |
| 10 | 57.0 | 43.0 | 71.5 | 29.2 | 73.0 | 46.1 | 43.1 | 125.4 | 67.9 |
| 11 | 57.0 | 43.0 | 69.0 | 29.1 | 74.8 | 46.0 | 43.9 | 121.1 | 67.6 |

TABLE 4

GPC results for the molecular weight using triple detection, refractive index, light scattering (LS) at 90° and 15° and viscosity. Data are presented as average of duplicate runs.

| Polymer | Mn (Da) | Mw (Da) | Đ |
|---|---|---|---|
| 1 | 2845 | 18557 | 6.55 |
| 2 | 831 | 3593 | 4.40 |
| 3 | 1299 | 3825 | 2.94 |
| 4 | 2100 | 4308 | 2.05 |
| 5 | 1640 | 3305 | 2.10 |
| 6 | 5597 | 43858 | 7.89 |
| 7 | 2759 | 16763 | 6.08 |
| 8 | 1202 | * | * |
| 9 | 3102 | 5479 | 1.81 |
| 10 | 2411 | 12438 | 5.28 |
| 11 | 2456 | 19599 | 7.98 |

*Polymer 8 has a very low light scattering signal which prevented accurate calculation of the Mw.

TABLE 5

Spectral range for labelled $^1$H NMR peaks

| Label | Range |
|---|---|
| $A_1$ | 6.35-6.30 |
| $A_2$ | 5.73-5.68 |
| B | 4.28-4.00 |
| C | 3.78-3.75 |
| D | 3.70-3.67 |
| E | 3.66-3.59 |
| F | 3.36-3.31 |
| G | 2.92-2.75 |
| H | 1.72-1.50 |
| I | 1.40-1.20 |

Supplemental Methods

Derivation of $^1$H NMR Assessment Equations

To perform assessment of $^1$H NMR spectra for polymer content according to functional group and esterification, equations were developed to delineate peak overlap. Peaks are defined according to FIG. 2A. Peaks are further confirmed through spectra for each monomer, triethyl citrate (TEC) (FIG. 14A), dimethyl itaconate (DMI) (FIG. 14B), and 1,8-octanediol (OD) (FIG. 14C). Given the potential for water contamination at peak H (1.56 ppm in deuterated chloroform)[91], we used a system of equations to separate the contributions of peak I integration as a calculation basis. Overlap of peaks is seen between TEC endgroups and OD at peak B (TEC endgroups: $B_{TEC}$, and 1,8-octanediol: $B_{OD}$), and peak I (TEC endgroups: $I_{TEC}$, and 1,8-octanediol: $I_{OD}$). Therefore, a system of equations was developed using the relationship between these peaks to allow for assessment.

First, we defined the following:

$$I = I_{TEC} + I_{OD}$$

$$B = B_{TEC} + B_{OD}$$

The expected proton ratio of citrate content ($I_{TEC}$: 9 protons/molecule, $B_{TEC}$: 6 protons/molecule) and OD ($I_{OD}$: 8 protons/molecule, $B_{OD}$+E: 4 protons/molecule) gives the following, $$I_{OD} = 2(B_{OD} + E)$$

$$I_{TEC} = 3/2 B_{TEC}$$

Substituting, $$B_{OD} = B - 2/3 I_{TEC}$$

$$I_{OD} = 2(B - 2/3 I_{TEC} + E)$$

$$I_{TEC} = I - 2(B - 2/3 I_{TEC} + E)$$

giving the equation, $$I_{TEC} = 3[2(B+E) - I] \tag{7}$$

This allowed us to calculate $I_{OD}$:

$$I_{OD} = I - I_{TEC} \tag{8}$$

Using equations 7 and 8, we then had enough independent equations to use the I peak in calculations summarized in the manuscript. Here, we describe the derivation of each equation with as it corresponds to peaks identified in FIG. 13A.

Determination of Polymer Content

To assess the integrated acid monomer (TEC/DMI) content in the polymer (Citrate/ITA), we compared the peak integration values of respective backbone proton NMR peaks for ITA (Peak F, 2 protons/molecule) and citrate (Peak G, 4 protons/molecule) to a basis of the OD (Peak $I_{OD}$, 8 protons/molecule) content in the polymer. This allowed for the development of Equations 1 & 2 that describe the acid content by percentage of the overall alcohol content:

$$\text{ITA polymer content} = \frac{4F}{I_{OD}} \times 100\% \tag{1}$$

$$\text{Citrate polymer content} = \frac{2G}{I_{OD}} \times 100\% \tag{2}$$

To calculate the yield of monomer incorporation, we used the calculated polymer content in comparison to the respective feed ratio of DMI and TEC, $$\text{Monomer incorporation Yield} = \frac{\text{polymer content}}{\text{monomer feed}} \times 100\% \tag{3}$$

As an indicator of monomer incorporation in the polymer chain, we next looked to assess the esterification of monomer endgroups as a measure of polymerization through condensation of each monomer group into the polymer chain. First, we defined the percentage of free endgroups for each of the monomers:

For citrate, we compared the ratio of $I_{TEC}$ to G, which would theoretically be 9:4 protons if no end groups were esterified, $$\text{Endgroups}_{citrate} = \frac{4}{9} \frac{I_{TEC}}{G} \tag{9}$$

For ITA, we compared C+D to F, which would theoretically be 6:2 protons if no end groups were esterified, $$\text{Endgroups}_{ITA} = \frac{(C+D)}{3F} \tag{10}$$

For OD, we compared E to $I_{OD}$, which would theoretically be 4:8 protons if no end groups were esterified, $$\text{Endgroups}_{OD} = \frac{2E}{I_{OD}} \tag{11}$$

Then, to determine the degree of esterification, we subtracted the ratio of endgroups from 1 and determined a percentage of esterified endgroups for each moiety, $$\%\text{Esterified}_{citrate} = \left(1 - \frac{4}{9}\frac{I_{TEC}}{G}\right) \times 100\% \tag{4}$$

$$\%\text{Esterified}_{ITA} = \left(1 - \frac{(C+D)}{3F}\right) \times 100\% \tag{5}$$

$$\%\text{Esterified}_{OD} = \left(1 - \frac{2E}{I_{OD}}\right) \times 100\% \tag{6}$$

Finally, to confirm the maintenance of unsaturated pendant group on the itaconate functional groups in PICO materials equation 12 was used.

$$\text{Maintenance of ITA unsaturated group} = \frac{(A_1 + A_2)}{F} \tag{12}$$

We used this calculation method to develop the calculated values presented in Table 1, Table 3 and FIG. 13 in the main text.

FTIR Measurement

Polymers were characterized using ATR-FTIR (Perkin Elmer Spectrum One). 32 scans from 4000 to 550 cm$^{-1}$ were completed at a resolution of 4 cm$^{-1}$ and corrections for ATR, baseline and smoothing were performed (Spectrum, Perkin Elmer).

Molecular Weight Assessment

The molecular weight was determined by gel permeation chromatography with a Viscotek GPCmax, using a triple detection configuration with a VE 3580 RI Detector to measure the refractive index (RI) and Viscotek 270 Dual Detector for light scattering (LS) and viscosity measurements. The refractive index increment (dn/dc) was determined using a Wyatt OptiLab rEx. For dn/dc determination the polymer was dissolved in tetrahydrofuran (THF) at five concentrations ranging from 0.2 mg/mL to 15 mg/mL. The dn/dc values were measured for three polymers (2, 6, and 10) to ensure the change in monomer feed did not change the dn/dc value. The three values were in good agreement with an average of 0.0766±0.005 mL/g, which was used for the analysis of all the samples. Samples for GPC were prepared by dissolving the pre-polymer gels in THF (5 mg/mL).

Cyclic Elastomeric Material Properties

For assessment of long-term mechanical stability, cyclic tensile tests were performed using methods described elsewhere[92, 93]. Samples were generated and crosslinked as described for elastomeric tensile testing, then crosslinked polymer samples were cut into 15 mm by 4 mm rectangular strips and assembled into a mechanical tester (Bose, ElectroForce 5200 Biodynamic Test Instrument). A sample length between grips of 5 mm was maintained. Cyclic tensile tests were performed at a frequency of 1 Hz and a strain of 10% for 1500 cycles using a triangular waveform programmed into WinTest software. Cycling loading data was presented as stress and strain initialized to the start of the first cyclic loading cycle.

REFERENCES

1 Teo, A. J. T. et al. Polymeric Biomaterials for Medical Implants and Devices. *ACS Biomaterials Science & Engineering* 2, 454-472, doi:10.1021/acsbiomaterials.5b00429 (2016).

2 Schmalzried, T. P. & Callaghan, J. J. Current concepts review-wear in total hip and knee replacements. *JBJS* 81, 115-136 (1999).

3 Busscher, H. J. et al. Biomaterial-Associated Infection: Locating the Finish Line in the Race for the Surface. *Science translational medicine* 4, 153rv110, doi:10.1126/scitranslmed.3004528 (2012).

4 Higgins, D. M. et al. Localized immunosuppressive environment in the foreign body response to implanted biomaterials. *Am J Pathol* 175, 161-170, doi:10.2353/ajpath.2009.080962 (2009).

5 Luan, H. H. & Medzhitov, R. Food Fight: Role of Itaconate and Other Metabolites in Antimicrobial Defense. *Cell Metab* 24, 379-387, doi:10.1016/j.cmet.2016.08.013 (2016).

6. Strelko, C. L. et al. Itaconic acid is a mammalian metabolite induced during macrophage activation. *Journal of the American Chemical Society* 133, 16386-16389, doi:10.1021/ja2070889 (2011).
7. Shin, J. H. et al. (1)H NMR-based metabolomic profiling in mice infected with *Mycobacterium tuberculosis*. *J Proteome Res* 10, 2238-2247, doi:10.1021/pr101054m (2011).
8. Sugimoto, M. et al. Non-targeted metabolite profiling in activated macrophage secretion. *Metabolomics* 8, 624-633, doi:10.1007/s11306-011-0353-9 (2011).
9. Ryan, D. G. et al. Coupling Krebs cycle metabolites to signalling in immunity and cancer. *Nature Metabolism* 1, 16-33, doi:10.1038/s42255-018-0014-7 (2018).
10. McFadden, B. & Purohit, S. Itaconate, an isocitrate lyase-directed inhibitor in *Pseudomonas indigofera*. *Journal of bacteriology* 131, 136-144 (1977).
11. Rittenhouse, J. W. & McFadden, B. A. Inhibition of isocitrate lyase from *Pseudomonas indigofera* by itaconate. *Archives of biochemistry and biophysics* 163, 79-86 (1974).
12. Garaude, J. et al. Mitochondrial respiratory-chain adaptations in macrophages contribute to antibacterial host defense. *Nat Immunol* 17, 1037-1045, doi:10.1038/ni.3509 (2016).
13. Michelucci, A. et al. Immune-responsive gene 1 protein links metabolism to immunity by catalyzing itaconic acid production. *Proceedings of the National Academy of Sciences* 110, 7820-7825, doi:10.1073/pnas.1218599110 (2013).
14. Naujoks, J. et al. IFNs Modify the Proteome of *Legionella*-Containing Vacuoles and Restrict Infection Via IRG1-Derived Itaconic Acid. *PLoS Pathog* 12, e1005408, doi:10.1371/journal.ppat.1005408 (2016).
15. O'Neill, L. A. J. & Artyomov, M. N. Itaconate: the poster child of metabolic reprogramming in macrophage function. *Nat Rev Immunol*, doi:10.1038/s41577-019-0128-5 (2019).
16. Cordes, T. et al. Immunoresponsive Gene 1 and Itaconate Inhibit Succinate Dehydrogenase to Modulate Intracellular Succinate Levels. *The Journal of biological chemistry* 291, 14274-14284, doi:10.1074/jbc.M115.685792 (2016).
17. Lampropoulou, V. et al. Itaconate Links Inhibition of Succinate Dehydrogenase with Macrophage Metabolic Remodeling and Regulation of Inflammation. *Cell Metab* 24, 158-166, doi:10.1016/j.cmet.2016.06.004 (2016).
18. Mills, E. L. et al. Itaconate is an anti-inflammatory metabolite that activates Nrf2 via alkylation of KEAP1. *Nature*, doi:10.1038/nature25986 (2018).
19. Bambouskova, M. et al. Electrophilic properties of itaconate and derivatives regulate the IkappaBzeta-ATF3 inflammatory axis. *Nature*, doi:10.1038/s41586-018-0052-z (2018).
20. Hayes, J. D. & Dinkova-Kostova, A. T. The Nrf2 regulatory network provides an interface between redox and intermediary metabolism. *Trends Biochem Sci* 39, 199-218, doi:10.1016/j.tibs.2014.02.002 (2014).
21. Winkler, M., Lacerda, T. M., Mack, F. & Meier, M. A. R. Renewable Polymers from Itaconic Acid by Polycondensation and Ring-Opening-Metathesis Polymerization. *Macromolecules* 48, 1398-1403, doi:10.1021/acs.macromol.5b00052 (2015).
22. Hammerer, F., Chang, J. H., Duncan, D., Ruiz, A. C. & Auclair, K. Small molecule restores itaconate sensitivity in *Salmonella enterica*: a potential new approach to treat bacterial infections. *Chembiochem*, doi:10.1002/cbic.201600078 (2016).
23. Davies, L. C., Jenkins, S. J., Allen, J. E. & Taylor, P. R. Tissue-resident macrophages. *Nat Immunol* 14, 986-995, doi:10.1038/ni.2705 (2013).
24. Sadtler, K. et al. Design, clinical translation and immunological response of biomaterials in regenerative medicine. *Nature Reviews Materials* 1, doi:10.1038/natrevmats.2016.40 (2016).
25. Yang, S., Leong, K.-F., Du, Z. & Chua, C.-K. The design of scaffolds for use in tissue engineering. Part I. Traditional factors. *Tissue engineering* 7, 679-689 (2001).
26. Engelberg, I. & Kohn, J. Physico-mechanical properties of degradable polymers used in medical applications: a comparative study. *Biomaterials* 12, 292-304 (1991).
27. Pomerantseva, I. et al. Degradation behavior of poly (glycerol sebacate). *Journal of biomedical materials research. Part A* 91, 1038-1047, doi:10.1002/jbm.a.32327 (2009).
28. Hotaling, N. A., Tang, L., Irvine, D. J. & Babensee, J. E. Biomaterial Strategies for Immunomodulation. *Annu Rev Biomed Eng* 17, 317-349, doi:10.1146/annurev-bioeng-071813-104814 (2015).
29. Anderson, J. M., Rodriguez, A. & Chang, D. T. Foreign body reaction to biomaterials. *Seminars in immunology* 20, 86-100, doi:10.1016/j.smim.2007.11.004 (2008).
30. Sadtler, K. et al. Divergent immune responses to synthetic and biological scaffolds. *Biomaterials* 192, 405-415, doi:10.1016/j.biomaterials.2018.11.002 (2019).
31. Sasikaran, J., Ziemski, M., Zadora, P. K., Fleig, A. & Berg, I. A. Bacterial itaconate degradation promotes pathogenicity. *Nature chemical biology* 10, 371-377, doi:10.1038/nchembio.1482 (2014).
32. Ahn, S., Jung, J., Jang, I. A., Madsen, E. L. & Park, W. Role of Glyoxylate Shunt in Oxidative Stress Response. *The Journal of biological chemistry* 291, 11928-11938, doi:10.1074/jbc.M115.708149 (2016).
33. Bergman, J. M., Wrande, M. & Hughes, D. Acetate availability and utilization supports the growth of mutant sub-populations on aging bacterial colonies. *PLoS One* 9, e109255, doi:10.1371/journal.pone.0109255 (2014).
34. Dolan, S. K. & Welch, M. The Glyoxylate Shunt, 60 Years On. *Annual Review of Microbiology* 72, 309-330, doi:10.1146/annurev-micro-090817-062257 (2018).
35. Lindsey, T. L., Hagins, J. M., Sokol, P. A. & Silo-Suh, L. A. Virulence determinants from a cystic fibrosis isolate of *Pseudomonas aeruginosa* include isocitrate lyase. *Microbiology* 154, 1616-1627, doi:10.1099/mic.0.2007/014506-0 (2008).
36. ElAzzouny, M. et al. Dimethyl itaconate is not metabolized into itaconate intracellularly. *The Journal of biological chemistry*, doi:10.1074/jbc.C117.775270 (2017).
37. Chen, Z., Bozec, A., Ramming, A. & Schett, G. Anti-inflammatory and immune-regulatory cytokines in rheumatoid arthritis. *Nat Rev Rheumatol*, doi:10.1038/s41584-018-0109-2 (2018).
38. Booth, A. N., Taylor, J., Wilson, R. H. & DeEds, F. THE INHIBITORY EFFECTS OF ITACONIC ACID IN VITRO AND IN VIVO. *Journal of Biological Chemistry* 195, 697-702 (1952).
39. Marim, F. M., Silveira, T. N., Lima, D. S., Jr. & Zamboni, D. S. A method for generation of bone marrow-derived macrophages from cryopreserved mouse bone marrow cells. *PLoS One* 5, e15263, doi:10.1371/journal.pone.0015263 (2010).

40 Shrum, B. et al. A robust scoring system to evaluate sepsis severity in an animal model. *BMC research notes* 7, 233 (2014).

41 Huyer, L. D. et al. Biomaterial based cardiac tissue engineering and its applications. *Biomedical materials* 10, 034004, doi:10.1088/1748-6041/10/3/034004 (2015).

42 Lamba, N. K. *Polyurethanes in biomedical applications*. (Routledge, 2017).

43 Ye, H., Zhang, K., Kai, D., Li, Z. & Loh, X. J. Polyester elastomers for soft tissue engineering. *Chem Soc Rev* 47, 4545-4580, doi:10.1039/c8cs00161h (2018).

44 Li, Y., Thouas, G. A. & Chen, Q.-Z. Biodegradable soft elastomers: synthesis/properties of materials and fabrication of scaffolds. *RSC Advances* 2, 8229, doi:10.1039/c2ra20736b (2012).

45 Langer, R. & Tirrell, D. A. Designing materials for biology and medicine. *Nature* 428, 487-492, doi:http://www.nature.com/nature/journal/v428/n6982/suppinfo/nature02388 S1, html (2004).

46 Chan, B. P. & Leong, K. W. Scaffolding in tissue engineering: general approaches and tissue-specific considerations. *European spine journal: official publication of the European Spine Society, the European Spinal Deformity Society, and the European Section of the Cervical Spine Research Society* 17 Suppl 4, 467-479, doi: 10.1007/s00586-008-0745-3 (2008).

47 Cohn, D. & Salomon, A. H. Designing biodegradable multiblock PCL/PLA thermoplastic elastomers. *Biomaterials* 26, 2297-2305 (2005).

48 Jeong, S. I. et al. In vivo biocompatibility and degradation behavior of elastic poly (l-lactide-co-ε-caprolactone) scaffolds. *Biomaterials* 25, 5939-5946 (2004).

49 Wang, L. S., Chen, H. C., Xiong, Z. C., Pang, X. B. & Xiong, C. D. A Completely Biodegradable Poly [(l-lactide)-co-(ε-caprolactone)] Elastomer Reinforced by in situ Poly (glycolic acid) Fibrillation: Manufacturing and Shape-Memory Effects. *Macromolecular Materials and Engineering* 295, 381-385 (2010).

50 Martin, D. P. & Williams, S. F. Medical applications of poly-4-hydroxybutyrate: a strong flexible absorbable biomaterial. *Biochemical engineering journal* 16, 97-105 (2003).

51 Wang, Y., Ameer, G. A., Sheppard, B. J. & Langer, R. A tough biodegradable elastomer. *Nat Biotech* 20, 602-606, doi:http://www.nature.com/nbt/journal/v20/n6/suppinfo/nbt0602-602 S1.html (2002).

52 Yang, J., Webb, A. R., Pickerill, S. J., Hageman, G. & Ameer, G. A. Synthesis and evaluation of poly(diol citrate) biodegradable elastomers. *Biomaterials* 27, 1889-1898, doi:10.1016/j.biomaterials.2005.05.106 (2006).

53 Amsden, B. Curable, biodegradable elastomers: emerging biomaterials for drug delivery and tissue engineering. *Soft matter* 3, doi:10.1039/b707472g (2007).

54 Nijst, C. L. E. et al. Synthesis and Characterization of Photocurable Elastomers from Poly(glycerol-co-sebacate). *Biomacromolecules* 8, 3067-3073, doi:10.1021/bm070423u (2007).

55 Ifkovits, J. L., Padera, R. F. & Burdick, J. A. Biodegradable and radically polymerized elastomers with enhanced processing capabilities. *Biomedical materials* 3, 034104, doi:10.1088/1748-6041/3/3/034104 (2008).

56 Wang, Y., Kibbe, M. R. & Ameer, G. A. Photo-crosslinked Biodegradable Elastomers for Controlled Nitric Oxide Delivery. *Biomater Sci* 1, 625-632, doi:10.1039/C3BM00169E (2013).

57 Amsden, B. G., Misra, G., Gu, F. & Younes, H. M. Synthesis and characterization of a photo-cross-linked biodegradable elastomer. *Biomacromolecules* 5, 2479-2486 (2004).

58 Timbart, L. & Amsden, B. G. Functionalizable biodegradable photocrosslinked elastomers based on 2-oxepane-1,5-dione. *Journal of Polymer Science Part A: Polymer Chemistry* 46, 8191-8199, doi:10.1002/pola.23117 (2008).

59 Tran, R. T. et al. Synthesis and characterization of a biodegradable elastomer featuring a dual crosslinking mechanism. *Soft matter* 6, 2449-2461, doi:10.1039/C001605E (2010).

60 Davenport Huyer, L. et al. Highly Elastic and Moldable Polyester Biomaterial for Cardiac Tissue Engineering Applications. *ACS Biomaterials Science & Engineering*, doi:10.1021/acsbiomaterials.5b00525 (2016).

61 Gyawali, D., Tran, R. T., Guleserian, K. J., Tang, L. & Yang, J. Citric-acid-derived photo-cross-linked biodegradable elastomers. *Journal of biomaterials science. Polymer edition* 21, 1761-1782, doi:10.1163/092050609X12567178204169 (2010).

62 Zhao, H. & Ameer, G. A. Modulating the mechanical properties of poly(diol citrates) via the incorporation of a second type of crosslink network. *Journal of Applied Polymer Science* 114, 1464-1470, doi:10.1002/app.30735 (2009).

63 Jabbari, E. et al. Synthesis, material properties, and biocompatibility of a novel self-cross-linkable poly (caprolactone fumarate) as an injectable tissue engineering scaffold. *Biomacromolecules* 6, 2503-2511, doi: 10.1021/bm050206y (2005).

64 Zhang, B., Montgomery, M., Davenport-Huyer, L., Korolj, A. & Radisic, M. Platform technology for scalable assembly of instantaneously functional mosaic tissues. *Science Advances* 1, doi:10.1126/sciadv.1500423 (2015).

65 Lai, B. F. L. et al. InVADE: Integrated Vasculature for Assessing Dynamic Events. *Advanced Functional Materials* 27, doi:10.1002/adfm.201703524 (2017).

66 Zhao, Y. et al. A Platform for Generation of Chamber-Specific Cardiac Tissues and Disease Modeling. *Cell, doi:*10.1016/j.cell.2018.11.042.

67 Zhang, B. et al. Biodegradable scaffold with built-in vasculature for organ-on-a-chip engineering and direct surgical anastomosis. *Nature materials, doi:*10.1038/nmat4570 (2016).

68 Montgomery, M. et al. Flexible shape-memory scaffold for minimally invasive delivery of functional tissues. *Nature materials, doi:*10.1038/nmat4956 (2017).

69 Robert, T. & Friebel, S. Itaconic acid—a versatile building block for renewable polyesters with enhanced functionality. *Green Chem.* 18, 2922-2934, doi:10.1039/c6gc00605a (2016).

70 Pitt, C. G., Hendren, R. W., Schindler, A. & Woodward, S. C. The enzymatic surface erosion of aliphatic polyesters. *Journal of Controlled Release* 1, 3-14 (1984).

71 Rai, R., Tallawi, M., Grigore, A. & Boccaccini, A. R. Synthesis, properties and biomedical applications of poly (glycerol sebacate) (PGS): A review. *Progress in Polymer Science* 37, 1051-1078, doi:10.1016/j.progpolymsci.2012.02.001 (2012).

72 Tran, R. T., Yang, J. & Ameer, G. A. Citrate-Based Biomaterials and Their Applications in Regenerative Engineering. *Annual Review of Materials Research* 45, 277-310, doi:10.1146/annurev-matsci-070214-020815 (2015).

73 Serrano, M. C., Chung, E. J. & Ameer, G. A. Advances and Applications of Biodegradable Elastomers in Regenerative Medicine. *Advanced Functional Materials* 20, 192-208, doi:10.1002/adfm.200901040 (2010).

74 O'Neil, M. J. *The Merck index: an encyclopedia of chemicals, drugs, and biologicals.* (RSC Publishing, 2013).

75 Pellis, A., Hanson, P. A., Comerford, J. W., Clark, J. H. & Farmer, T. J. Enzymatic synthesis of unsaturated polyesters: functionalization and reversibility of the aza-Michael addition of pendants. *Polymer Chemistry, doi:* 10.1039/c8py01655k (2019).

76 Brännström, S., Finnveden, M., Johansson, M., Martinelle, M. & Malmström, E. Itaconate Based Polyesters: Selectivity and Performance of Esterification Catalysts. *European Polymer Journal, doi:*10.1016/j.eurpolymj.2018.04.017 (2018).

77 Yang, J., Webb, A. R. & Ameer, G. A. Novel Citric Acid-Based Biodegradable Elastomers for Tissue Engineering. *Advanced Materials* 16, 511-516, doi:10.1002/adma.200306264 (2004).

78 Lang, N. et al. A Blood-Resistant Surgical Glue for Minimally Invasive Repair of Vessels and Heart Defects. *Science translational medicine* 6, 218ra216, doi:10.1126/scitranslmed.3006557 (2014).

79 Hoenig, E. et al. Mechanical Properties of Native and Tissue-Engineered Cartilage Depend on Carrier Permeability: A Bioreactor Study. *Tissue Engineering Part A* 19, 1534-1542, doi:10.1089/ten.tea.2012.0538 (2013).

80 Borschel, G. H., Kia, K. F., Kuzon, W. M. & Dennis, R. G. Mechanical properties of acellular peripheral nerve. *Journal of Surgical Research* 114, 133-139, doi:10.1016/s0022-4804(03)00255-5 (2003).

81 Riley, W. A., Barnes, R. W., Evans, G. W. & Burke, G. L. Ultrasonic measurement of the elastic modulus of the common carotid artery. The Atherosclerosis Risk in Communities (ARIC) Study. *Stroke* 23, 952-956 (1992).

82 Verdonk, E. D., Wickline, S. A. & Miller, J. G. Anisotropy of ultrasonic velocity and elastic properties in normal human myocardium. *The Journal of the Acoustical Society of America* 92, 3039-3050 (1992).

83 Venugopal, J. R. et al. Biomaterial strategies for alleviation of myocardial infarction. *Journal of the Royal Society Interface* 9, 1-19 (2011).

84 Eder, A. et al. Effects of proarrhythmic drugs on relaxation time and beating pattern in rat engineered heart tissue. *Basic research in cardiology* 109, 436 (2014).

85 Zimmermann, W.-H. et al. Engineered heart tissue grafts improve systolic and diastolic function in infarcted rat hearts. *Nature medicine* 12, 452 (2006).

86 Nunes, S. S. et al. Biowire: a platform for maturation of human pluripotent stem cell-derived cardiomyocytes. *Nature methods* 10, 781-787, doi:10.1038/nmeth.2524 (2013).

87 Lv, A., Li, Z.-L., Du, F.-S. & Li, Z.-C. Synthesis, Functionalization, and Controlled Degradation of High Molecular Weight Polyester from Itaconic Acid via ADMET Polymerization. *Macromolecules* 47, 7707-7716, doi:10.1021/ma5020066 (2014).

88 Tian, H., Tang, Z., Zhuang, X., Chen, X. & Jing, X. Biodegradable synthetic polymers: Preparation, functionalization and biomedical application. *Progress in Polymer Science* 37, 237-280, doi:10.1016/j.progpolymsci.2011.06.004 (2012).

89 Watson, E., Tatara, A. M., Kontoyiannis, D. P. & Mikos, A. G. Inherently Antimicrobial Biodegradable Polymers in Tissue Engineering. *ACS Biomaterials Science & Engineering*, doi:10.1021/acsbiomaterials.6b00501 (2016).

90 Montgomery, M. et al. Method for the Fabrication of Elastomeric Polyester Scaffolds for Tissue Engineering and Minimally Invasive Delivery. *ACS Biomaterials Science & Engineering* 4, 3691-3703, doi:10.1021/acsbiomaterials.7b01017 (2018).

91 Gottlieb, H. E., Kotlyar, V. & Nudelman, A. NMR chemical shifts of common laboratory solvents as trace impurities. *The Journal of organic chemistry* 62, 7512-7515 (1997).

92 Lin, X. et al. A viscoelastic adhesive epicardial patch for treating myocardial infarction. *Nat Biomed Eng*, doi: 10.1038/s41551-019-0380-9 (2019).

93 Engelmayr, G. C., Jr. et al. Accordion-like honeycombs for tissue engineering of cardiac anisotropy. *Nature materials* 7, 1003-1010, doi:10.1038/nmat2316 (2008).

Therefore what is claimed is:

1. A biomaterial comprising poly(itaconate-co-citrate-co-octanediol).

2. The biomaterial of claim 1, wherein the biomaterial has hydrolytic degradability.

3. The biomaterial of claim 1, wherein the biomaterial has tunable elasticity in a range from about 0.05 to about 1.7 MPa.

4. The biomaterial of claim 1, wherein the biomaterial has ability to crosslink under ultraviolet light with radical polymerization.

5. The biomaterial of claim 1, wherein the biomaterial is in a form of a scaffold for a tissue patch.

6. The biomaterial of claim 5, wherein the tissue patch is a cardiac patch.

7. A method of treating an infection or an inflammation in a subject, the method comprising:
   providing a biomaterial comprising poly(itaconate-co-citrate-co-octanediol); and
   administering the biomaterial to the subject.

8. The method of claim 7, wherein administering the biomaterial comprises intraperitoneal injection of the biomaterial.

9. The method of claim 7, wherein the biomaterial is in a form of a scaffold for a tissue patch.

10. The method of claim 9, wherein the tissue patch is a cardiac patch.

11. A method of fabricating a biomaterial comprising poly(itaconate-co-citrate-co-octanediol), the method comprising:
    forming a polyester backbone including diol monomers and citrate monomers; and
    reacting the polyester backbone with itaconate monomers.

12. The method of claim 11, wherein the biomaterial is fabricated at atmospheric pressure at about 120° C.

13. The method of claim 11, further comprising:
    moulding the biomaterial into a scaffold for a tissue patch.

14. The method of claim 13, wherein the tissue patch is a cardiac patch.

* * * * *